US007763777B2

(12) United States Patent
da Costa e Silva et al.

(10) Patent No.: US 7,763,777 B2

(45) Date of Patent: Jul. 27, 2010

(54) PROTEIN PHOSPHATASE STRESS-RELATED POLYPEPTIDES AND METHODS OF USE IN PLANTS

(75) Inventors: Oswaldo da Costa e Silva, Neustadt (DE); Nocha Van Thielen, Durham, NC (US); Ruoying Chen, Duluth, GA (US); Hans Bohnert, Champaign, IL (US); Manabu Ishitani, Medley, FL (US)

(73) Assignee: BASF Plant Science GmbH (DE)

( * ) Notice: Subject to any disclaimer, the term of this patent is extended or adjusted under 35 U.S.C. 154(b) by 512 days.

(21) Appl. No.: 11/419,016

(22) Filed: May 18, 2006

(65) Prior Publication Data

US 2007/0028333 A1 Feb. 1, 2007

Related U.S. Application Data

(63) Continuation-in-part of application No. 10/236,699, filed on Sep. 5, 2002, now Pat. No. 7,091,402.

(60) Provisional application No. 60/317,305, filed on Sep. 5, 2001.

(51) Int. Cl.

| | |
|---|---|
| ***A01H 1/00*** | (2006.01) |
| *C07H 21/04* | (2006.01) |
| *C07K 14/415* | (2006.01) |
| *C12N 15/00* | (2006.01) |

(52) U.S. Cl. ........................... 800/295; 435/6; 435/468; 435/419; 435/320.1; 530/370; 536/23.1; 536/23.6; 800/278

(58) Field of Classification Search ..................... 435/6, 435/69.1, 468, 419, 320.1, 183; 536/23.2, 536/23.6; 800/278, 295; 530/370

See application file for complete search history.

(56) References Cited

U.S. PATENT DOCUMENTS

| | | | |
|---|---|---|---|
| 6,818,805 | B2 | 11/2004 | e Silva et al. |
| 7,271,316 | B2 | 9/2007 | e Silva et al. |

OTHER PUBLICATIONS

Kang et al., Database A_Geneseq_200808, Accession No. ABB83820, KR2001106331, Nov. 29, 2001, see Result 2.*

* cited by examiner

*Primary Examiner*—Phuong T Bui

(74) *Attorney, Agent, or Firm*—Patricia A. McDaniels

(57) ABSTRACT

A transgenic plant transformed by a Protein Phosphatase Stress-Related polypeptide (PPSRP) coding nucleic acid, wherein modifying expression of the nucleic acid sequence in the plant results in increased growth/yield under normal or stress conditions and/or increased tolerance to environmental stress as compared to a wild type variety of the plant also provided are agricultural products, including seeds, produced by the transgenic plants. Also provided are isolated PPSRPs, and isolated nucleic acid coding PPSRPs, and vectors and host cells containing the latter.

16 Claims, 11 Drawing Sheets pBPSJH001

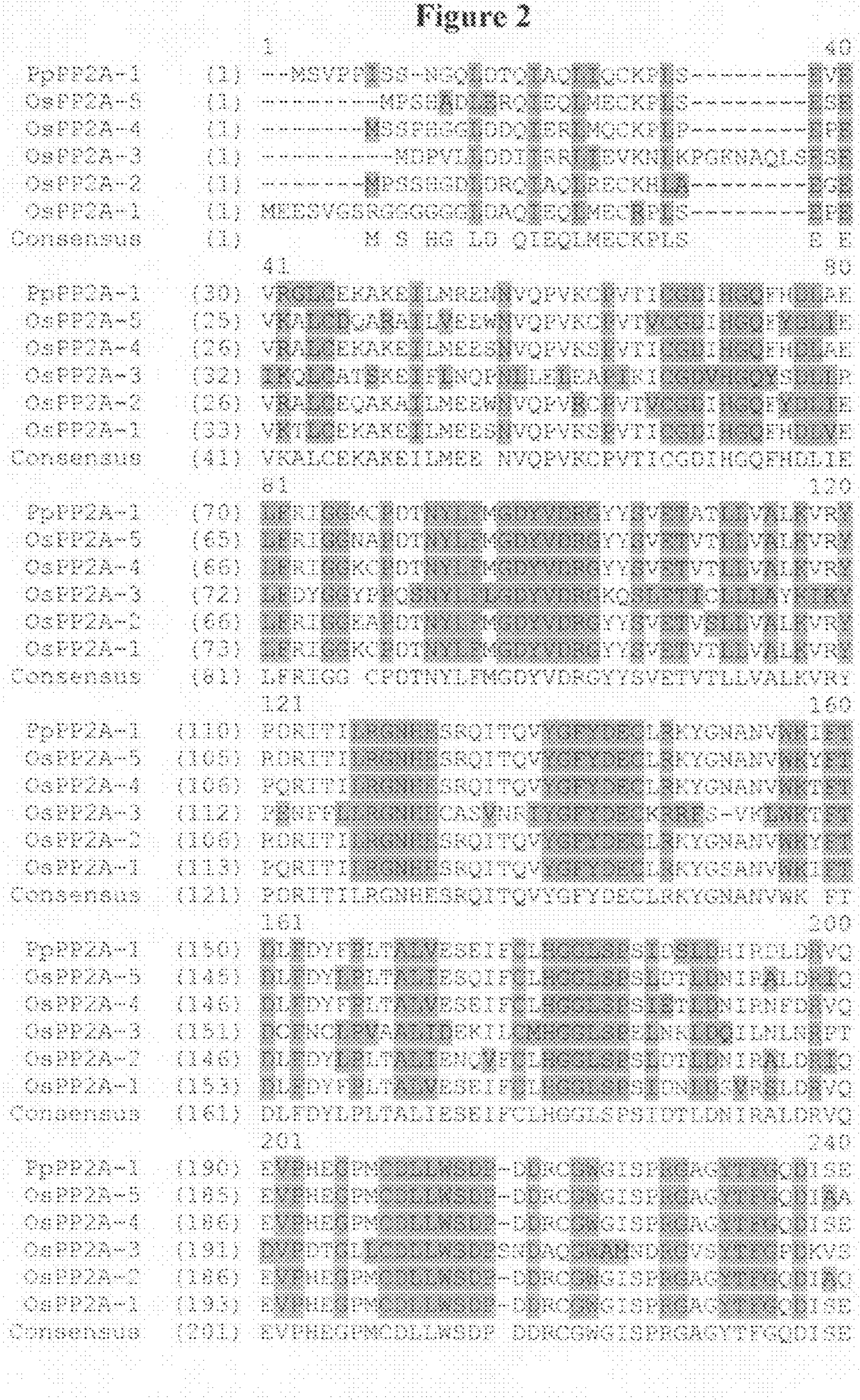

Figure 2

```
                   1                                        40
PpPP2A-1    (1)    --MSVPG SS-NSQ OTQ AQ  GCKP S--------  V
OsPP2A-5    (1)    ------- MPSHGD RQ EQ MECKP S--------  S
OsPP2A-4    (1)    ------- SSPHSG DDQ ER MQCKP P--------  P
OsPP2A-3    (1)    ---------MDPVL DDI RR EVKN KPGRNAQLS  S
OsPP2A-2    (1)    ------- PSSHGD DRQ AQ PECKH S--------  G
OsPP2A-1    (1)    MEESVGSRGGGGGG DAQ EQ MEC PS--------  P
Consensus   (1)             M S  BG LQ QIEQLMECKPLS       E E

                   41                                       80
PpPP2A-1    (30)   V   EKAKE LMREH VQPVKC VTI    I   FH   AE
OsPP2A-5    (25)   V   QASA LNEEW VQPVKC VT     I       E
OsPP2A-4    (26)   V   EKAKE LNEES VQPVKS VTI    I   FH   AE
OsPP2A-3    (32)    Q  AT KG F NQP  LE EA  KI              P
OsPP2A-2    (26)   V   EQAKA LMEEW VQPV C VT     I   F    E
OsPP2A-1    (33)   V T EKAKE LMEES VQPVKS VTI    I   FH   E
Consensus   (41)   VKALCEKAKEILMSE NVQPVKCPVTICGDIHGQFHDLIE

                   81                                      120
PpPP2A-1    (70)    RI  KC DT    M        YY V  AT  V L VR
OsPP2A-5    (65)    RI  NA DT    M        YY V  VT  V L VR
OsPP2A-4    (66)    RI  KC DT    M        YY V  VT  V L VR
OsPP2A-3    (72)    DY  YP CS             KQ    TC   AY   
OsPP2A-2    (66)    RI  EA DT    M        YY V  V   V L VR
OsPP2A-1    (73)    RI  KC DT    M        YY V  VT  V L VR
Consensus   (81)   LFRIGG CPQTNYLFMGDYVDRGYYSVETVTLLVALKVRY

                   121                                     160
PpPP2A-1    (110)  PQRITI        SSRQITQV        L KYGNANV  I
OsPP2A-5    (105)  RQRITI        SSRQITQV        L KYGNANV  Y
OsPP2A-4    (106)  PQRITI        SSRQITQV        L KYGNANV  T
OsPP2A-3    (112)   BFT          CASVNR          K  S-VK   T
OsPP2A-2    (106)  RQRITI        SSRQITQV        L KYGNANV  Y
OsPP2A-1    (113)  PQRITI        SSRQITQV        L KYGSANV  I
Consensus   (121)  PQRITILRGNEESSQITQVYGFYDECLRKYGNANVWK FT

                   161                                     200
PpPP2A-1    (150)   L DYF LT    ESEIF L         S D    HIRDLD VQ
OsPP2A-5    (145)   L DY  LT    ESQIF L         S DT   NIR LD  Q
OsPP2A-4    (146)   L DYF LT    ESEIF L         S ST   NIRNFD VQ
OsPP2A-3    (151)    C NC  A    EKTI            NA    ILNLS PT
OsPP2A-2    (146)   L DY  LT    ENQ F L         S DT   NIP LD  Q
OsPP2A-1    (153)   L DY  LT    ESEIF L         S DN   C R LD VQ
Consensus   (161)  DLFDYLPLTALIESEIFCLHGGLSPSTDTLDNIRALDRVQ

                   201                                     240
PpPP2A-1    (190)  E  HE PN       -D RC  GISP  AG    Q ISE
OsPP2A-5    (185)  E  HE PN       -D RC  GISP  AG    Q ISA
OsPP2A-4    (186)  E  HE PN       -D RC  GISP  AG    Q ISE
OsPP2A-3    (191)    DT L         SN AQ    GD  VS    F KVS
OsPP2A-2    (186)  E  HE PN       -D RC  GISP  AG    Q I K
OsPP2A-1    (193)  E  HE PN       -D RC  GISP  AG    Q ISE
Consensus   (201)  EVPHEGPNCDLLNSDP DDRCGWGISPRGAGYTFGQDISE
```

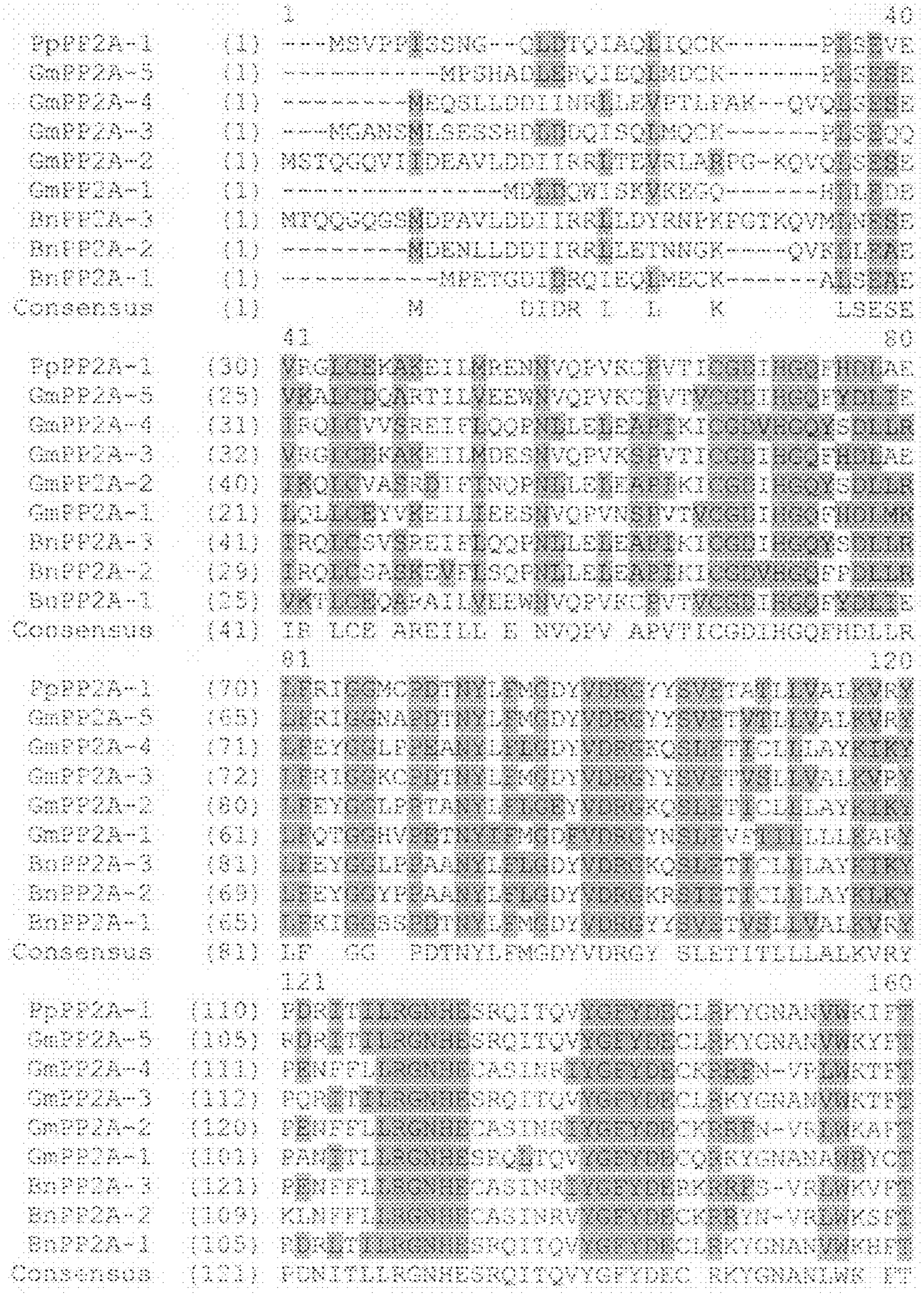

Figure 3

```
                1                                        40
PpPP2A-1   (1)  ----MSVPP SSNG--C  TQIAQ IQCK------P S VE
GmPP2A-5   (1)  ----------MPSHAQ  RQIEQ MDCK------  S  E
GmPP2A-4   (1)  --------- EQSLLDDIINR LE PTLPAK--QVQ    E
GmPP2A-3   (1)  ----MGANS LGESSHD DQISQ MQCK------ S QQ
GmPP2A-2   (1)  MSTQGQVI DEAVLDDIIRR TE RLA PG-KQVQ  S  E
GmPP2A-1   (1)  ----------MD QWISK KEGQ-------  L DE
BnPP2A-3   (1)  NTQQGQGS DPAVLDDIIRR LDYRNPKFGTKQVM N  E
BnPP2A-2   (1)  --------- DENLLDDIIRR LETNNGK-----QVS L  E
BnPP2A-1   (1)  ----------MPETGUI RQIEQ MECK------A S DE
Consensus  (1)           M     UIDR I L   K        LSESE
                41                                       80
PpPP2A-1   (30) RG   K  EIL REN VQPVK VT I   I  Q    AE
GmPP2A-5   (25)  AL  QQ RTIL EEW VQPVK VT    I       E
GmPP2A-4   (31) RQ  VV REI  QQP LE E   KI      Q S
GmPP2A-3   (32) RG   K  EIL DES VQPVK VT I   I        AE
GmPP2A-2   (40) RQ  VA    TF NQP LE E   KI      S
GmPP2A-1   (21) QL   YV EIL EES VQPVN VT    I    Q
BnPP2A-3   (41) RQ   SV REI  QQP LE E   KI      S
BnPP2A-2   (29) RQ   SA  E  F SQP LE E    KI      FP
BnPP2A-1   (35)  T  QQ AIL EEW VQPVE VT    I    F   E
Consensus  (41) IR LCE AREILL E NVQPV APVTICGDIHGQFHDLLR
                81                                       120
PpPP2A-1   (70)  RI MC T L M DY    YG  TA L AL  R
GmPP2A-5   (65)  RI NA T L M DY    YY  T L  AL  R
GmPP2A-4   (71)  EY LP A  L  DY   KQ  T CL LAY
GmPP2A-3   (72)  RI KC T L M DY    YY  T LI AL  P
GmPP2A-2   (80)  EY LP TA L  DY   KQ  T CL LAY
GmPP2A-1   (61)  QT HV T    D    YN   V   LLL AH
BnPP2A-3   (81)  EY LP AA    DY   KQ  T CL LAY
BnPP2A-2   (69)  EY YP AA    DY   KR  T CL LAY  K
BnPP2A-1   (65)  KI  SS T L M DY    YY  T L  AL  R
Consensus  (81) LP  GG   PDTNYLFMGDYVDRGY SLETITLLLALKVRY
                121                                      160
PpPP2A-1   (110) P R T    SRQITQV    CL YGNAN  KIF
GmPP2A-5   (105) S R T    SRQITQV    CL KYGNAN  KYE
GmPP2A-4   (111) P NFFL   CASINR     CK  N-VT   KTF
GmPP2A-3   (112) PQR T    SRQITQV    CL KYGNAN  KTF
GmPP2A-2   (120) P NFFL   CASINR     CK  N-VR   KAF
GmPP2A-1   (101) PAH TL   SRQ TQV    CQ RYGNAN  RYC
BnPP2A-3   (121) P NFFL   CASINR     PK  S-VS   KVF
BnPP2A-2   (109) K NFFI   CASINRV    CK  YN-VR  KSF
BnPP2A-1   (105) P R T    SRQITQV    CL KYGNAN  KHF
Consensus  (121) PENITLLRGNHESRQITQVYGFYDEC RKYGNANIWR FT
```

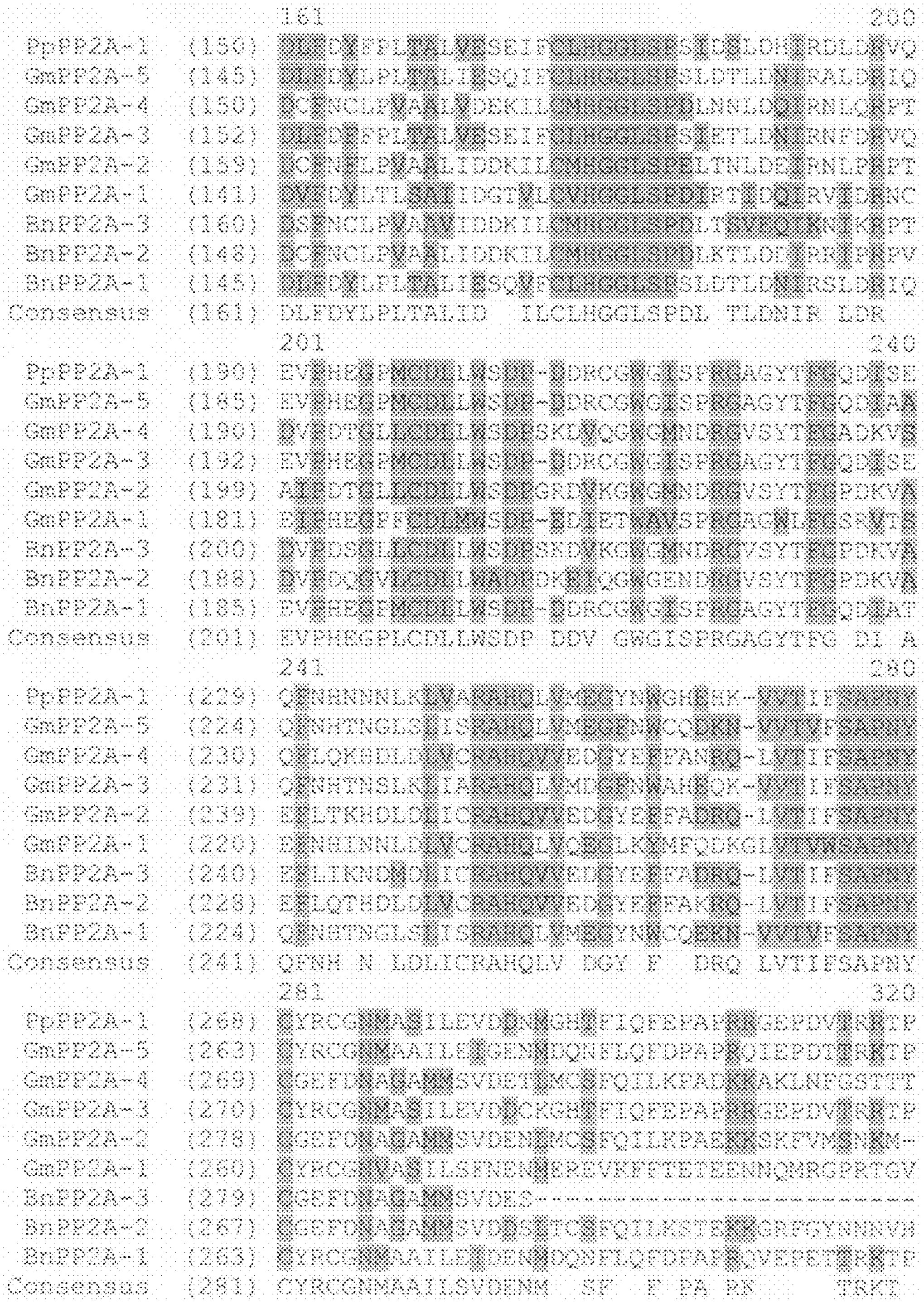

Figure 3 Continued

```
               161                                        200
PpPP2A-1 (150) ..D.FPL..L..SEI..........S.D.LDH.RDL..VQ
GmPP2A-5 (145) ..D.LPL..LI.SQIE.........SLDTLL..RALD.IQ
GmPP2A-4 (150) .CNCLP.A.I.DEKIL.........LNSLDD.RNLQ.PT
GmPP2A-3 (152) ..D.FPL..L..SEI..........S.ETLD..RNFD.VQ
GmPP2A-2 (159) .CN.LP.A.LIDDKIL.........LTNLDE.RNLP.PT
GmPP2A-1 (141) ..D.LTL...IDGT.L.........PT.D..RV.D.NC
BnPP2A-3 (160) .SNCLP.A..IDDKIL.........LT....SN.K.PT
BnPP2A-2 (148) .CNCLP.A.LIDDKIL.........LKTLD..RR.P.PV
BnPP2A-1 (145) ..D.LFL..LI.SQ.E.........SLDTLD..RSLD.IQ
Consensus (161) DLFDYLPLTALID  ILCLHGGLSPDL TLDNIR LDR
               201                                        240
PpPP2A-1 (190) EV.HE.P...L.S..-.DRCG.G.SF..AGYT..QD.SE
GmPP2A-5 (185) EV.HE.P...L.S..-.DRCG.G.SP..AGYT..QD.A.
GmPP2A-4 (190) .V.DT.L...L.S..SKD.QG.G.ND..VSYT..ADKV.
GmPP2A-3 (192) EV.HE.P...L.S..-.DRCG.G.SP..AGYT..QD.SE
GmPP2A-2 (199) A..DT.L...L.S..GRD.KG.G.ND..VSYT..PDKV.
GmPP2A-1 (181) E..HE.PF...S..-.D.ET..VSP..AG.L..SP.T.
BnPP2A-3 (200) .V.DS.L...L.S..SKD.KG.G.ND..VSYT..PDKV.
BnPP2A-2 (188) .V.D..V...L.S..DK..QG.G.END..VSYT..PDKV.
BnPP2A-1 (185) EV.HE.P...L.S..-.DRCG.G.SP..AGYT..QD.A.
Consensus (201) EVPHEGPLCDLLWSDP DDV GWGISPRGAGYTFG DI A
               241                                        280
PpPP2A-1 (229) Q.NHNNLK...A...L.M..YN.GH.HK-.V..IF....
GmPP2A-5 (224) Q.NHTNGLS..IS...L.M..Q.DN.CQ.K.-.V..F...
GmPP2A-4 (230) Q.LQKEDL..C.A...ED.YE.FAN.Q-L...IF.....
GmPP2A-3 (231) Q.NHTNSLK.IA...L.MD..NWAH.QK-.V..IF....
GmPP2A-2 (239) E.LTKHDLD..IC.....ED.YE.FA.KQ-L...IF....
GmPP2A-1 (220) E.NHIBNLD..VC...LI.Q.LK.MFQLKGL...V....
BnPP2A-3 (240) E.LIKND.D..IC.....EL.YE.FA...-L...IF....
BnPP2A-2 (228) E.LQTHDLD..IC.....ED.YE.FAK.Q-L...IF....
BnPP2A-1 (224) Q.N.TNGLS..IS...L.M..YN.CQ.K.-.V..F....
Consensus (241) QFNH N LDLICRAHQLV DGY F  DRQ LVTIFSAPNY
               281                                        320
PpPP2A-1 (268) .YRCG..A..ILEVD.N.GH.FIQFEPAP..GEPDV.R.TP
GmPP2A-5 (263) .YRCG..AAILE..GEN.DQNFLQFDPAP..QIEPDT.R.TP
GmPP2A-4 (269) .GEFD.A.A..SVDET.MC.FQILKPAD..AKLNFGSTTT
GmPP2A-3 (270) .YRCG..A..ILEVD.CKGH.FIQFEPAP..GEPDV.R.TP
GmPP2A-2 (278) .GEFD.A.A..SVDEN.MC.FQILKPAE..SKFVM.N.M-
GmPP2A-1 (260) .YRCG..A..ILSFNEN.EREVKFFTETEENN.QMRGPRTGV
BnPP2A-3 (279) .GEFD.A.A..SVDES-------
BnPP2A-2 (267) .GEFD.A.A..SVD.S.TC.FQILKSTE..GRFGYNNNV.
BnPP2A-1 (263) .YRCG..AAILE..DEN.DQNFLQFDPAP..QVEPET.R.TP
Consensus (281) CYRCGNMAAIISVOENM  SF  F  PA  RN       TRKT
```

Figure 3 Continued

```
                      321          336
PpPP2A-1     (308)  DYFL------------
GmPP2A-5     (303)  DYFL------------
GmPP2A-4     (309)  AKPGNSPAGVKVGRY-
GmPP2A-3     (310)  DYFL------------
GmPP2A-2     (317)  ----------------
GmPP2A-1     (300)  PYFL------------
BnPP2A-3     (295)  ----------------
BnPP2A-2     (307)  RPGTPPHKGGKGG---
BnPP2A-1     (303)  DYFL------------
Consensus    (321)   YFL
```

Figure 4

```
                       1                                      40
  PpPP2A-1    (1)  ---MSVPPISSNGQLDTQIAQLMQCKPLS---------EV
  OsPP2A-5    (1)  --------MPSHADLDRQIEQLMECKPLS---------ES
  OsPP2A-4    (1)  -------MSSPHGGLDDQIERLMQCKPLP---------EP
  OsPP2A-3    (1)  ---------MDPVLLDDIIRRLMEVKNLKPG-KNAQLSES
  OsPP2A-2    (1)  -------MPSSHGDLDRQIAQLRECKHLS---------EG
  OsPP2A-1    (1)  MEESVGSRGGGGGLDAQIEQLMECKPLS---------EP
  GmPP2A-5    (1)  --------MPSHADLDRQIEQLMDCKPLS---------ES
  GmPP2A-4    (1)  ---------MEQSLLDDIINRLLEVPTL-PA-KQVQLSES
  GmPP2A-3    (1)  -MGANSMLSESSHDLDDQISQLMQCKPLS---------EQ
  GmPP2A-2    (1)  -MSTQGQVIIDEAVLDDIIRRLTEVKLARPG-KQVQLSES
  GmPP2A-1    (1)  ------------MDLDQWISKLKEGQHLL---------ED
  BnPP2A-3    (1)  -MTQQGQGSMDPAVLDDIIRRLMDYKNPKPGTKQVMLNES
  BnPP2A-2    (1)  ---------MDENLLDDIIRRLMETNNG----KQVKLLEA
  BnPP2A-1    (1)  --------MPETGDLDRQIEQLMECKALS---------EA
  Consensus   (1)              G LDDQI QLMECK LS         ES
                   41                                     80
  PpPP2A-1   (29)  EVRGLCEKAKEILMPENNVQPVKCPVTICGDIHGQFHDLA
  OsPP2A-5   (24)  EVRALCDQARAILVEEWNVQPVKCPVTVCGDIHGQFYDLL
  OsPP2A-4   (25)  EVRALCEKAKEILMEESNVQPVKAPVTICGDIHGQFHDLA
  OsPP2A-3   (31)  EVRQLCATAKEIFMNQPNVLEVEAPVKICGDVHGQYSDLL
  OsPP2A-2   (25)  EVRALCEQAKAILMEEWNVQPVKCPVTVCGDIHGQFYDLL
  OsPP2A-1   (32)  EVKTLCEKAKEILMEESNVQPVKAPVTICGDIHGQFHDLV
  GmPP2A-5   (24)  EVKALCDQARTILVEEWNVQPVKCPVTVCGDIHGQFYDLL
  GmPP2A-4   (30)  EVRQLCVVSREIFLQQPNLLEVEAPVKICGDVHGQYSDLL
  GmPP2A-3   (31)  QVRGLCEKAKEILMDESNVQPVKAPVTICGDIHGQFHDLA
  GmPP2A-2   (39)  EVKQLCVASRDIFLNQPNLLEVEAPVKICGDIHGQYSDLL
  GmPP2A-1   (20)  EVQLLCEYVKEILMEESNVQPVNAPVTVCGDIHGQFHDLM
  BnPP2A-3   (40)  EVRQLCSVSREIFLQQPNLLEVEAPVKICGDIHGQYSDLL
  BnPP2A-2   (28)  EVRQLCSASKEVFLSQPNLLEVEAPVKICGDVHGQFPDLL
  BnPP2A-1   (24)  EVKTLCEQARAILVEEWNVQPVKCPVTVCGDIHGQFYDLL
  Consensus  (41)  EVR LCE AKEILMEE NVQPVKAPVTICGDIHGQFHDLL
                   81                                    120
  PpPP2A-1   (69)  ELFRIGGMCPDTNYLFMGDYVDRGYYSVETATLLVALKVR
  OsPP2A-5   (64)  ELFRIGGNAPDTNYLFMGDYVDRGYYSVETVTLLVALKVR
  OsPP2A-4   (65)  ELFRIGGKCPDTNYLFMGDYVDRGYYSVETVTLLVALKVR
  OsPP2A-3   (71)  RLFDYGGYPPQTNYLFMGDYVDRGKQSLETICLLLAYKIK
  OsPP2A-2   (65)  ELFRIGGEAPDTNYLFMGDYVDRGYYSVETVTLLVALKVR
  OsPP2A-1   (72)  ELFRIGGKCPDTNYLFMGDYVDRGYYSVETVTLLVALKVR
  GmPP2A-5   (64)  ELFRIGGNAPDTNYLFMGDYVDRGYYSVETVTLLVALKVR
  GmPP2A-4   (70)  RLFEYGGLPPEANYLFMGDYVDRGKQSLETICLLLAYKIK
  GmPP2A-3   (71)  ELFRIGGKCPDTNYLFMGDYVDRGYYSVETVTLLVALKVR
  GmPP2A-2   (79)  RLFEYGGLPPTANYLFMGDYVDRGKQSLETICLLLAYKIK
  GmPP2A-1   (60)  KLFQTGGHVPDTNYLFMGDYVDRGYNSLEVFTLLLLLLAR
  BnPP2A-3   (80)  RLFEYGGLPPAANYLFMGDYVDRGKQSLETICLLLAYKIK
  BnPP2A-2   (68)  RLFEYGGYPPAANYLFMGDYVDRGKRSLETICLLLAYKIK
  BnPP2A-1   (64)  ELFKIGGSSPDTNYLFMGDYVDRGYYSVETVSLLVALKVR
  Consensus  (81)  ELFRIGG  PDTNYLFMGDYVDRGYYSVETVTLLVALKVR
```

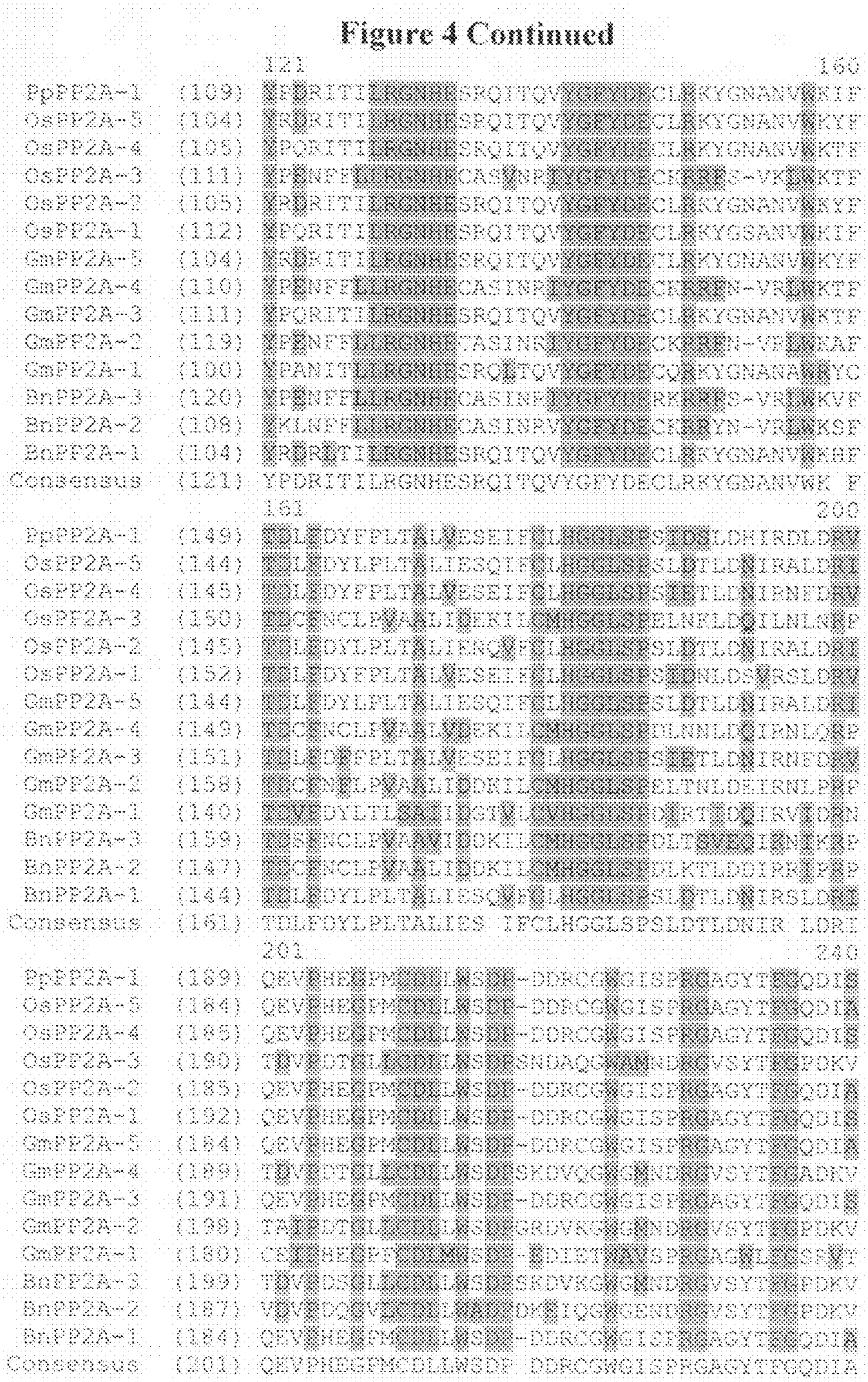

Figure 4 Continued

```
              121                                            160
PpPP2A-1 (109) PFRITIL......SRQITQV......CL.KYGNANV.RIF
OsPP2A-5 (104) R.RITIL......SRQITQV......CL.KYGNANV.KYF
OsPP2A-4 (105) PQRITIL......SRQITQV......IL.KYGNANV.KTF
OsPP2A-3 (111) PLNFF........CASINP.......CL...S-VR.KTF
OsPP2A-2 (105) P.RITIL......SRQITQV......CL.KYGNANV.KYF
OsPP2A-1 (112) PQRITIL......SRQITQV......CL.KYGSANV.RIF
GmPP2A-5 (104) R.RITIL......SRQITQV......IL.KYGNANV.KYF
GmPP2A-4 (110) PLNFF........CASINP.......CL...N-VR.KTF
GmPP2A-3 (111) PQRITIL......SRQITQV......CL.KYGNANV.KTF
GmPP2A-2 (119) PLNFF........TASING.......CK.R.N-VF.RAF
GmPP2A-1 (100) PANIT........SRQITQV......CQ.KYGNASA.YC
BnPP2A-3 (120) PLNFL........CASINP.......RK..S-VR.KVF
BnPP2A-2 (108) KLNFF........CASINRV......CL.YN-VR.KSF
BnPP2A-1 (104) R.RITIL......SRQITQV......CL.KYGNANV.KHF
Consensus(121) YPDRITILEGNHESRQITQVYGFYDECLRKYGNANVWK F

              161                                            200
PpPP2A-1 (149) .L.DYFPLT.L.ESEIF.L.......S.D.LDHIRDLD..
OsPP2A-5 (144) .L.DYLPLT.L.IESQIF.L.......SL.TLD.IRALD.
OsPP2A-4 (145) .L.DYFPLT.L.ESEIF.L.......S..TLD.IRNFD.
OsPP2A-3 (150) .C.NCLF.A.LI.EKIL.........ELNFLD.ILNLN..P
OsPP2A-2 (145) .L.DYLPLT.L.IENQ.F.L.......SL.TLD.IRALD.
OsPP2A-1 (152) .L.DYFPLT.L.ESEIF.L.......S.NLDS.RSLD..
GmPP2A-5 (144) .L.DYLPLT.L.IESQIF.L.......SL.TLD.IRALD.
GmPP2A-4 (149) .C.NCLF.A.LI.EKIL.........DLNNLL.IRNL..P
GmPP2A-3 (151) .L.FPLT.L.ESEIF.L.........S..TLD.IRNFD..
GmPP2A-2 (158) .C.NLP.A.LI.DKIL..........ELTNLDEHRNLP..P
GmPP2A-1 (140) .V.DYLTL.....GT.L.........QRT.Q.ERV.D.N
BnPP2A-3 (159) .S.NCLF.A.VI.DKEL.........DLT....IBN.K.P
BnPP2A-2 (147) .C.NCLF.A.LI.DKIL.........DLKTLDDIRF.P.P
BnPP2A-1 (144) .L.DYLPLT.L.IESQ.F.L.......SI.TLD.IRSLD..
Consensus(161) TDLFDYLPLTALICS IPCLHGGLSPSLDTLDWFR LDRE

              201                                            240
PpPP2A-1 (189) QEV.HE.PM...LLS..-DDRCG.GISP.AGYT.QDI.
OsPP2A-5 (184) QEV.HE.PM...LLS..-DDRCG.GISP.AGYT.QDI.
OsPP2A-4 (185) QEV.HE.PK...LLS..-DDRCG.GISP.AGYT.QDI.
OsPP2A-3 (190) T.V.DT.L....LLS..SNDAQG.....D.VSYT.PDKV
OsPP2A-2 (185) QEV.HE.PM...LLS..-DDRCG.GISP.AGYT.QDI.
OsPP2A-1 (192) QEV.HE.PM...LLS..-DDRCG.GISP.AGYT.QDI.
GmPP2A-5 (184) QEV.HE.PM...LLS..-DDRCG.GISP.AGYT.QDI.
GmPP2A-4 (189) T.V.PT.L....LLS..SKDVQG.GND.VSYT.ADKV
GmPP2A-3 (191) QEV.HE.PM...LLS..-DDRCG.GISP.AGYT.QDI.
GmPP2A-2 (198) TA..DT.L....LLS..GRDVKG.GND.VSYT.PDKV
GmPP2A-1 (180) C..HE.PF...LLS..-DIET..SP.AG.L..S..T
BnPP2A-3 (199) T.V.DS.L....LLS..SKDVKG.GND.VSYT.PDKV
BnPP2A-2 (187) V.V.DC.V....L...DF.IQG.SESI.VSYT.PDKV
BnPP2A-1 (184) QEV.HE.PM...LLS..-DDRCG.GISP.AGYT.QDI.
Consensus(201) QEVPHESPMCDLLWSDP DDRCGWGISPKGAGYTFGQDIA
```

Figure 4 Continued

```
                  241                                    280
PpPP2A-1   (228)  EQFNHNNNLKLVAHAHQLVMEGYNWGHDHK-VVTIFSAPN
OsPP2A-5   (223)  AQFNHTNGLSLISFAHQLVMEGFNWCQDRN-VVTVFSAPN
OsPP2A-4   (224)  EQFNHTNNLRLIAFAHQLVMEGFNWAHDQK-VVTIFSAPN
OsPP2A-3   (230)  AEFLEKHDLDLICRAHQVVEDGYEFFANRQ-LVTIFSAPN
OsPP2A-2   (224)  QQFNHTNGLSLISFAHQLVMEGFNWCQDRN-VVTVFSAPN
OsPP2A-1   (231)  EQFNHTNNLKLVAHAHQLVMEGYNWAHDQK-VVTIFSAPN
GmPP2A-5   (223)  AQFNHTNGLSLISFAHQLVMEGFNWCQDRN-VVTVFSAPN
GmPP2A-4   (229)  SQFLQKHDLDLVCRAHQVVEDGYEFFANRQ-LVTIFSAPN
GmPP2A-3   (230)  EQFNHTNSLKLIAFAHQLVMDGFNWAHDQK-VVTIFSAPN
GmPP2A-2   (238)  AEFLTKHDLDLICRAHQVVEDGYEFFADRQ-LVTIFSAPN
GmPP2A-1   (219)  SEFNHINNLDLVCRAHQLVQEGLEYMFQDKGLVTVWSAPN
BnPP2A-3   (239)  AEFLIKNDMDLICRAHQVVEDGYEFFADRQ-LVTIFSAPN
BnPP2A-2   (227)  AEFLQTHDLDLVCRAHQVVEDGYEFFAKRQ-LVTIFSAPN
BnPP2A-1   (223)  TQFNHTNGLSLISFAHQLVMEGYNWCQDRN-VVTVFSAPN
Consensus  (241)  AQFNHTN L LIAFAHQLVMEGYNW  DRQ VVTIFSAPN
                  281                                    320
PpPP2A-1   (267)  YCYRCGNMASILEVDENMGHSFIQFDFAPRRGEPDVTRKT
OsPP2A-5   (262)  YCYRCGNMAAILELGENMDQNFIQFDPAPRQIEPDTTRKT
OsPP2A-4   (263)  YCYRCGNMASILEVDECREHSFIQFEPAPRRGEPDVTRKT
OsPP2A-3   (269)  YCGEFDNAGAMMSVDETLMCSFQILKPARKMLGGSTNSKS
OsPP2A-2   (263)  YCYRCGNMAAILELGENMDQNFIQFDPAPRQIEPDTTRKT
OsPP2A-1   (270)  YCYRCGNMASILEVDECRNHSFIQFEPAPRRGEPDVTRKT
GmPP2A-5   (262)  YCYRCGNMAAILELGENMDQNFIQFDPAPRQIEPDTTRKT
GmPP2A-4   (268)  YCGEFLNAGAMMSVDETLMCSFQILKPADKKAKLNFGSTT
GmPP2A-3   (269)  YCYRCGNMASILEVDECKGHSFIQFEPAPRRGEPDVTPKT
GmPP2A-2   (277)  YCGEFINAGAMMSVDENLMCSFQILKPAEKKSKFVMSNKM
GmPP2A-1   (259)  YCYRCGNVASILSFNENMEREVKFFTETEENNQMRGPRTG
BnPP2A-3   (278)  YCGEFDNAGAMMSVDES-----------------------
BnPP2A-2   (266)  YCGEFLNAGAMMSVDESLTCSFQILKSTEKKGFFGYNNNV
BnPP2A-1   (262)  YCYRCGNMAAILEIDENMDQNFIQFDPAPRQVEPETTPKT
Consensus  (281)  YCYRCGNMAAILEVDENM  SFIQFDPAPRR EPD TRKT
                  321             337
PpPP2A-1   (307)  PDYFL------------
OsPP2A-5   (302)  PDYFL------------
OsPP2A-4   (303)  PDYFL------------
OsPP2A-3   (309)  GFKSLRGW---------
OsPP2A-2   (303)  PDYFL------------
OsPP2A-1   (310)  PDYFL------------
GmPP2A-5   (302)  PDYFL------------
GmPP2A-4   (308)  TAKPGNSPAGVKVGRY-
GmPP2A-3   (309)  PDYFL------------
GmPP2A-2   (317)  -----------------
GmPP2A-1   (299)  VPYFL------------
BnPP2A-3   (295)  -----------------
BnPP2A-2   (306)  HRPGTPPHKGGKGG---
BnPP2A-1   (302)  PDYFL------------
Consensus  (321)  PDYFL
```

Figure 5

| Gene Name | Former Identifier | Nucleic acid SEQ ID NO: | Protein SEQ ID NO: |
|---|---|---|---|
| PpPP2A-1 | EST4 | 1 & 2 | 3 |
| PpPP-1 | EST102 | 4 & 5 | 6 |
| BnPp2A-1 | BN48706417 | 7 | 8 |
| BnPP2A-2 | BN51288093 | 9 | 10 |
| BnPP2A-3 | BN51387173 | 11 | 12 |
| GmPp2A-1 | GM50770660 | 13 | 14 |
| GmPP2A-2 | GM48922444 | 15 | 16 |
| GmPP2A-3 | GM50131069 | 17 | 18 |
| GmPP2A-4 | GM47171610 | 19 | 20 |
| GmPP2A-5 | GM49671923 | 21 | 22 |
| OsPP2A-1 | OS41502678 | 23 | 24 |
| OsPP2A-2 | OS32806943 | 25 | 26 |
| OsPP2A-3 | OS35083313 | 27 | 28 |
| OsPP2A-4 | OS33003814 | 29 | 30 |
| OsPP2A-5 | OS34738749 | 31 | 32 |

Figure 6

| SEQ ID NO: | 8 | 10 | 12 | 6 | 3 | 20 | 16 | 22 | 18 | 14 | 26 | 30 | 32 | 28 | 24 |
|---|---|---|---|---|---|---|---|---|---|---|---|---|---|---|---|
| 8 | 100 | | | | | | | | | | | | | | |
| 10 | 41.1 | 100 | | | | | | | | | | | | | |
| 12 | 39.3 | 68.9 | 100 | | | | | | | | | | | | |
| 6 | 56 | 39.6 | 36.7 | 100 | | | | | | | | | | | |
| 3 | 77.5 | 42 | 39.3 | 53.8 | 100 | | | | | | | | | | |
| 20 | 42.5 | 75.5 | 73 | 37.5 | 42.8 | 100 | | | | | | | | | |
| 16 | 42.2 | 72.1 | 78.2 | 37.8 | 40.7 | 78 | 100 | | | | | | | | |
| 22 | 91.8 | 40.5 | 39.9 | 56.4 | 78.1 | 40.9 | 42.9 | 100 | | | | | | | |
| 18 | 76 | 42.1 | 40.2 | 52.5 | 87.5 | 42.2 | 41.3 | 77 | 100 | | | | | | |
| 14 | 55.7 | 39.6 | 37 | 91.4 | 55.1 | 37.5 | 37.5 | 56.4 | 53.8 | 100 | | | | | |
| 26 | 90.6 | 40.6 | 39 | 56.2 | 78.8 | 39.8 | 41 | 92.8 | 77 | 57.8 | 100 | | | | |
| 30 | 78.2 | 43.2 | 41 | 55.7 | 88.1 | 42.9 | 41.2 | 79.9 | 91.7 | 56.6 | 80.2 | 100 | | | |
| 32 | 92.5 | 40.8 | 39.6 | 56.4 | 78.1 | 41.2 | 42.9 | 99.3 | 77 | 56.7 | 93.5 | 79.9 | 100 | | |
| 28 | 42.3 | 73.6 | 72.9 | 38.1 | 42 | 81.2 | 78.1 | 42.3 | 41.9 | 37.7 | 41.3 | 42.9 | 42.3 | 100 | |
| 24 | 77.4 | 41.9 | 39.2 | 53.7 | 88.2 | 42.3 | 41.5 | 76.8 | 87.3 | 54.6 | 75.8 | 89.8 | 77.1 | 41.5 | 100 |

PROTEIN PHOSPHATASE STRESS-RELATED POLYPEPTIDES AND METHODS OF USE IN PLANTS

CROSS-REFERENCE TO RELATED APPLICATIONS

This application is a continuation-in-part application of U.S. Nonprovisional patent application Ser. No. 10/236,699 filed Sep. 5, 2002, and claims priority benefit of U.S. Provisional Patent Application No. 60/317,305 filed Sep. 5, 2001, both of which are hereby incorporated in their entirety.

BACKGROUND OF THE INVENTION

1. Field of the Invention

This invention relates generally to nucleic acid sequences encoding polypeptides that are associated with abiotic stress responses and abiotic stress tolerance in plants. In particular, this invention relates to nucleic acid sequences encoding polypeptides that confer upon a plant increased growth/yield under normal or water-limited conditions and/or increased tolerance under abiotic stress conditions.

2. Background Art

Abiotic environmental stresses, such as drought stress, salinity stress, heat stress, and cold stress, are major limiting factors of plant growth and productivity. Crop losses and crop yield losses of major crops such as soybean, rice, maize (corn), cotton, and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on development, growth, and yield of most crop plants are profound. Continuous exposure to drought conditions causes major alterations in the plant metabolism, which ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold and salt tolerance in model, drought- and/or salt-tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerance plants using biotechnological methods.

Drought and cold stresses, as well as salt stresses, have a common theme important for plant growth, and that is water availability. Plants are exposed during their entire life cycle to conditions of reduced environmental water content, and most plants have evolved strategies to protect themselves against these conditions of desiccation. However, if the severity and duration of the drought conditions are too great, the effects on plant development, growth and yield of most crop plants are profound. Furthermore, most of the crop plants are very susceptible to higher salt concentrations in the soil. Because high salt content in some soils results in less water being available for cell intake, high salt concentration has an effect on plants similar to the effect of drought on plants. Additionally, under freezing temperatures, plant cells lose water as a result of ice formation that starts in the apoplast and withdraws water from the symplast. A plant's molecular response mechanisms to each of these stress conditions are common, and protein phosphatases play an essential role in these molecular mechanisms.

Plant biomass is yield for forage crops like-alfalfa, silage corn, and hay. Many proxies for yield have been used in grain crops. Chief amongst these are estimates of plant size. Plant size can be measured in many ways depending on species and developmental stage, but include total plant dry weight, above-ground dry weight, above-ground fresh weight, leaf area, stem volume, plant height, rosette diameter, leaf length, root length, root mass, tiller number, and leaf number. Many species maintain a conservative ratio between the size of different parts of the plant at a given developmental stage. These allometric relationships are used to extrapolate from one of these measures of size to another (e.g. Tittonell et al 2005 Agric Ecosys & Environ 105: 213). Plant size at an early developmental stage will typically correlate with plant size later in development. A larger plant with a greater leaf area can typically absorb more light and carbon dioxide than a smaller plant and therefore will likely gain a greater weight during the same period (Fasoula & Tollenaar 2005 Maydica 50:39). This is in addition to the potential continuation of the micro-environmental or genetic advantage that the plant had to achieve the larger size initially. There is a strong genetic component to plant size and growth rate (e.g. ter Steege et al 2005 Plant Physiology 139:1078), and so for a range of diverse genotypes plant size under one environmental condition is likely to correlate with size under another (Hittalmani et al 2003 Theoretical Applied Genetics 107:679). In this way a standard environment is used as a proxy for the diverse and dynamic environments encountered at different locations and times by crops in the field.

Harvest index, the ratio of seed yield to above-ground dry weight, is relatively stable under many environmental conditions and so a robust correlation between plant size and grain yield can often be obtained (e.g. Rebetzke et al 2002 Crop Science 42:739). These processes are intrinsically linked because the majority of grain biomass is dependent on current or stored photosynthetic productivity by the leaves and stem of the plant (Gardener et al 1985 Physiology of Crop Plants. Iowa State University Press, pp 68-73) Therefore, selecting for plant size, even at early stages of development, has been used as an indicator for future potential yield (e.g. Tittonell et al 2005 Agric Ecosys & Environ 105: 213). When testing for the impact of genetic differences on stress tolerance, the ability to standardize soil properties, temperature, water, and nutrient availability and light intensity is an intrinsic advantage of greenhouse or plant growth chamber environments compared to the field. However, artificial limitations on yield due to poor pollination due to the absence of wind or insects, or insufficient space for mature root or canopy growth, can restrict the use of these controlled environments for testing yield differences. Therefore, measurements of plant size in early development, under standardized conditions in a growth chamber or greenhouse, are standard practices to provide indication of potential genetic yield advantages.

There is a fundamental physiochemically-constrained trade-off in all terrestrial, photosynthetic organisms, between carbon dioxide ($CO_2$) absorption and water loss (Taiz and Zeiger, 1991, Plant Physiology, Benjamin/Cummings Publishing Co., p. 94). $CO_2$ needs to be in aqueous solution for the action of $CO_2$ fixation enzymes such as Rubisco (Ribulose 1,5-bisphosphate Carboxylase/Oxygenase) and PEPC (Phosphoenolpyruvate carboxylase). As a wet cell surface is required for $CO_2$ diffusion, evaporation will inevitably occur when the humidity is below 100% (Taiz and Zeiger, 1991, p. 257). Plants have numerous physiological mechanisms to reduce water loss (e.g. waxy cuticles, stomatal closure, leaf hairs, sunken stomatal pits). As these barriers do not discriminate between water and $CO_2$ flux, these water conservation measures will also act to increase resistance to $CO_2$ uptake (Kramer, 1983, Water Relations of Plants, Academic Press p. 305). Photosynthetic $CO_2$ uptake is absolutely required for plant growth and biomass accumulation in photoautotrophic plants.

Water Use Efficiency (WUE) is a parameter frequently used to estimate the trade off between water consumption and $CO_2$ uptake/growth (Kramer, 1983, Water Relations of Plants, Academic Press p. 405). WUE has been defined and measured in multiple ways. One approach is to calculate the ratio of whole plant dry weight, to the weight of water consumed by the plant throughout its life (Chu et al., 1992, Oecologia 89:580). Another variation is to use a shorter time interval when biomass accumulation and water use are measured (Mian et al., 1998, Crop Sci. 38:390). Another approach is to utilize measurements from restricted parts of the plant, for example, measuring only aerial growth and water use (Nienhuis et al 1994 Amer J Bot 81:943). WUE also has been defined as the ratio of $CO_2$ uptake to water vapor loss from a leaf or portion of a leaf, often measured over a very short time period (e.g. seconds/minutes) (Kramer, 1983, p. 406). The ratio of $^{13}C/^{12}C$ fixed in plant tissue, and measured with an isotope ratio mass-spectrometer, also has been used to estimate WUE in plants using $C_3$ photosynthesis (Martin et al., 1999, Crop Sci. 1775).

An increase in WUE is informative about the relatively improved efficiency of growth and water consumption, but this information taken alone does not indicate whether one of these two processes has changed or both have changed. In selecting traits for improving crops, an increase in WUE due to a decrease in water use, without a change in growth would have particular merit in an irrigated agricultural system where the water input costs were high. An increase in WUE driven mainly by an increase in growth without a corresponding jump in water use would have applicability to all agricultural systems. In many agricultural systems where water supply is not limiting, an increase in growth, even if it came at the expense of an increased water use (i.e. no change in WUE), could also increase yield. Therefore new methods to increase both WUE and biomass accumulation are required to improve agricultural productivity. As WUE integrates many physiological processes relating to primary metabolism and water use, it is typically a highly polygenic trait with a large genotype by environment interaction (Richards et al., 2002, Crop Sci. 42:111). For these and other reasons, few attempts to select for WUE changes in traditional breeding programs have been successful.

Although some genes that are involved in stress responses and water use efficiency in plants have been characterized, the characterization and cloning of plant genes that confer stress tolerance and water use efficiency remains largely incomplete and fragmented. For example, certain studies have indicated that drought and salt stress in some plants may be due to additive gene effects, in contrast to other research that indicates specific genes are transcriptionally activated in vegetative tissue of plants under osmotic stress conditions. Although it is generally assumed that stress-induced proteins have a role in tolerance, direct evidence is still lacking, and the functions of many stress-responsive genes are unknown.

There is a need, therefore, to identify additional genes expressed in stress tolerant plants and plants that are efficient in water use that have the capacity to confer stress tolerance and/or increased water use efficiency to the host plant and to other plant species. Newly generated stress tolerant plants and plants with increased water use efficiency will have many advantages, such as an increased range in which the crop plants can be cultivated, by for example, decreasing the water requirements of a plant species. Other desirable advantages include increased resistance to lodging, the bending of shoots or stems in response to wind, rain, pests, or disease.

It is well recognized that reversible phosphorylation of proteins controls many cellular processes in plants and animals. The phosphorylation status of proteins is regulated by the opposing activities of protein kinases and protein phosphatases. Phosphorylation of eukaryotic proteins occurs predominantly on serine and threonine residues, and to a lesser extent, on tyrosine residues. In animals, protein phosphorylation plays well-known roles in diverse cellular processes such as glycogen metabolism, cell cycle control, and signal transduction (Smith, R. D. and Walker, J. C., 1996, Annu. Rev. Plant Physiol. Plant Mol. Biol. 47:101-125).

Protein phosphatase activities have been reported in most plant subcellular compartments, including mitochondria, chloroplast, nuclei, and the cytosol, and are associated with various membrane and particulate fractions. Some protein phosphatases are poorly characterized and may represent novel enzymes that are unique to plants. Others have biochemical properties that are very similar to well-known mammalian protein phosphatases, such as cytosolic protein serine/threonine phosphatases (MacKintosh C. and Cohen P. 1989 Biochem. J. 262:335-339). Two such plant serine/threonine phosphatases have been identified that function similar to mammalian type-1 (PP1) and type-2 (PP2) protein serine/threonine phosphatases. Biochemical and genetic studies in plants implicate PP1 and/or PP2 activity in signal transduction, hormonal regulation, mitosis, and control of carbon and nitrogen metabolism (Smith, R. D. and Walker, J. C., 1996, Annu. Rev. Plant Physiol. Plant Mol. Biol. 47:101-125).

Experimental evidence has implicated the involvement of protein phosphatases in the plant stress-signaling cascade, and more particularly, in stress perception and signal transduction linked to physiological mechanisms of adaptation in plants. For example, protein phosphatase 2C (PP2C) has been shown to be involved in stress responses in plants (Sheen, J. 1998 Proc. Natl. Acad. Sci. USA 95:975-980). It has also been demonstrated that, in yeast, the PP2B phosphatase calcineurin (CaN) is a focal component of a $Ca^{2+}$-dependent signal transduction pathway that mediates $Na^+$, $Li^-$, and $Mn^{2+}$ tolerance of *Saccharomyces cerevisiae* (Cunningham, K. W. and Fink, G. R. 1996 Mol. Cell. Biol. 16:2226-2237). CaN functions to limit intracellular $Na^+$ accumulation by regulating processes that restrict influx and enhance efflux of this cation across the plasma membrane. CaN also participates in cytosolic $Ca^{2+}$ homeostasis through the positive regulation of Golgi apparatus and vacuolar membrane-localized P-type ion pumps and negative control of a vacuolar $H^+/Ca^{2+}$ exchanger. Interestingly, overexpression of yeast CaN confers salt tolerance in plants, strongly indicating that modulation of stress signaling pathways by expression of an activated protein phosphatase substantially enhances plant stress tolerance (Pardo, J. M. et al. 1998 Proc. Natl. Acad. Sci. USA 95:9681-9686).

Although some genes that are involved in stress responses in plants have been characterized, the characterization and cloning of plant genes that confer stress tolerance remains largely incomplete and fragmented. For example, certain studies have indicated that drought and salt stress in some plants may be due to additive gene effects, in contrast to other research that indicates specific genes are transcriptionally activated in vegetative tissue of plants under osmotic stress conditions. Although it is generally assumed that stress-induced proteins have a role in tolerance, direct evidence is still lacking, and the functions of many stress-responsive genes are unknown.

There is a need, therefore, to identify genes expressed in stress tolerant plants that have the capacity to confer stress resistance to its host plant and to other plant species. Newly generated stress tolerant plants will have many advantages, such as increasing the range in which crop plants can be cultivated by, for example, decreasing the water requirements of a plant species.

SUMMARY OF THE INVENTION

This invention fulfills in part the need to identify new, unique protein phosphatases capable of conferring stress tolerance and/or increased growth/yield under normal or stress conditions to plants upon modifying expression of genes. The present invention describes a novel genus of Protein Phosphatase Stress-Related Polypeptides (PPSRPs) and PPSRP coding nucleic acids that are important for modulating a plant's growth or response to an environmental stress. More particularly, modifying expression of these PPSRP coding nucleic acids in a plant results in the plant's increased growth/yield under normal or stress conditions and/or increased tolerance to an environmental stress.

Therefore, the present invention includes an isolated plant cell comprising a PPSRP coding nucleic acid, wherein expression of the nucleic acid sequence in the plant cell results in increased growth/yield under normal or stress conditions and/or increased tolerance to environmental stress as compared to a wild type variety of the plant cell. Namely, described herein are Protein Phosphatase 2A-1 (PP2A-1) and Protein Phosphatase-1 (PP-1) from *Physcomitrella patens; Brassica napus* Protein Phosphatase PP2A-1 (BnPP2A-1), BnPP2A-2, and BnPP2A-3 from *Brassica napus; Glycine max* Protein Phosphatase PP2A-1 (GmPP2A-1), GmPP2A-2, GmPP2A-3, GmPP2A-4, and GmPP2A-5 from *Glycine max*; and *Oryza sativa Protein Phosphatase PP*2A-1 (OsPP2A-1), OsPP2A-2, OsPP2A-3, OsPP2A-4, and OsPP2A-5 from *Oryza sativa.*

The invention provides in some embodiments that the PPSRP and coding nucleic acid are those that are found in members of the genuses *Physcomitrella, Brassica, Glycine*, or *Oryza*. In another preferred embodiment, the nucleic acid and polypeptide are from a *Physcomitrella patens*, a *Brassica napus*, a *Glycine max*, or an *Oryza sativa*. The invention provides that the environmental stress can be salinity, drought, nitrogen, temperature, metal, chemical, pathogenic and oxidative stresses, or combinations thereof In preferred embodiments, the environmental stress can be drought, high salt or cold temperature.

The invention further provides a seed produced by a transgenic plant transformed by a PPSRP coding nucleic acid, wherein the plant is true breeding for increased growth/yield under normal or stress conditions and/or increased tolerance to environmental stress as compared to a wild type variety of the plant. The invention further provides a seed produced by a transgenic plant expressing a PPSRP, wherein the plant is true breeding for increased growth/yield under normal or stress conditions and/or increased tolerance to environmental stress as compared to a wild type variety of the plant.

The invention further provides an agricultural product produced by any of the below-described transgenic plants, plant parts, or seeds. The invention further provides an isolated PPSRP as described below. The invention further provides an isolated PPSRP coding nucleic acid, wherein the PPSRP coding nucleic acid codes for a PPSRP as described below.

The invention further provides an isolated recombinant expression vector comprising a PPSRP coding nucleic acid as described below, wherein modifying expression of the vector in a host cell results in increased growth/yield under normal or stress conditions and/or increased tolerance to environmental stress as compared to a wild type variety of the host cell. The invention further provides a host cell containing the vector and a plant containing the host cell.

The invention further provides a method of producing a transgenic plant with a PPSRP coding nucleic acid, wherein expression of the nucleic acid in the plant results in increased growth/yield under normal or stress conditions and/or increased tolerance to environmental stress as compared to a wild type variety of the plant comprising: (a) transforming a plant cell with an expression vector comprising a PPSRP coding nucleic acid, and (b) generating from the plant cell a transgenic plant with an increased tolerance to environmental stress as compared to a wild type variety of the plant. In preferred embodiments, the PPSRP and PPSRP coding nucleic acid are as described below.

The present invention further provides a method of identifying a novel PPSRP, comprising (a) raising a specific antibody response to a PPSRP, or fragment thereof, as described below; (b) screening putative PPSRP material with the antibody, wherein specific binding of the antibody to the material indicates the presence of a potentially novel PPSRP; and (c) identifying from the bound material a novel PPSRP in comparison to known PPSRP. Alternatively, hybridization with nucleic acid probes as described below can be used to identify novel PPSRP nucleic acids.

The present invention also provides methods of modifying stress tolerance of a plant comprising, modifying the expression of a PPSRP nucleic acid in the plant, wherein the PPSRP is as described below. The invention provides that this method can be performed such that the growth under normal or stress conditions and/or stress tolerance is either increased or decreased. Preferably, growth under normal or stress conditions and/or stress tolerance is increased in a plant via increasing expression of a PPSRP nucleic acid.

BRIEF DESCRIPTION OF THE DRAWINGS

FIG. 3 shows an alignment of the deduced amino acid sequence of PP2A-1 (SEQ ID NO:3) from *Physcomitrella patens* with deduced amino acid sequences of GmPP2A-1

Figure 1:
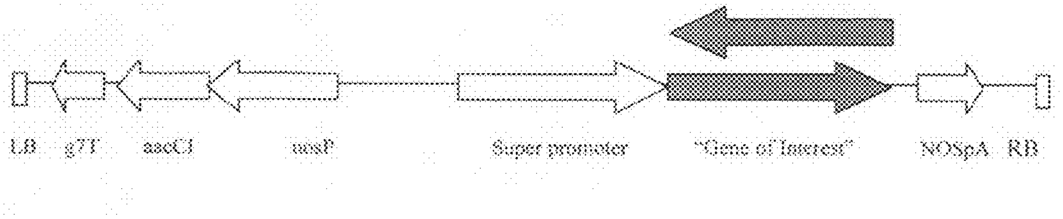
FIG. 1 shows a diagram of the plant expression vector pBPSJH001 containing the super promoter driving the expression of a PPSRP coding nucleic acid ("Gene of Interest"). The components are: aacCI gentamycin resistance gene (Hajdukiewicz et al., Plant Molec. Biol. 25: 989-94, 1994), NOS promoter (Becker et al., Plant Molec. Biol. 20: 1195-97 1992), g7T terminator (Becker et al., 1992), NOSpA terminator (Jefferson et al., EMBO J. 6:3901-7 1987).
Figure 2:
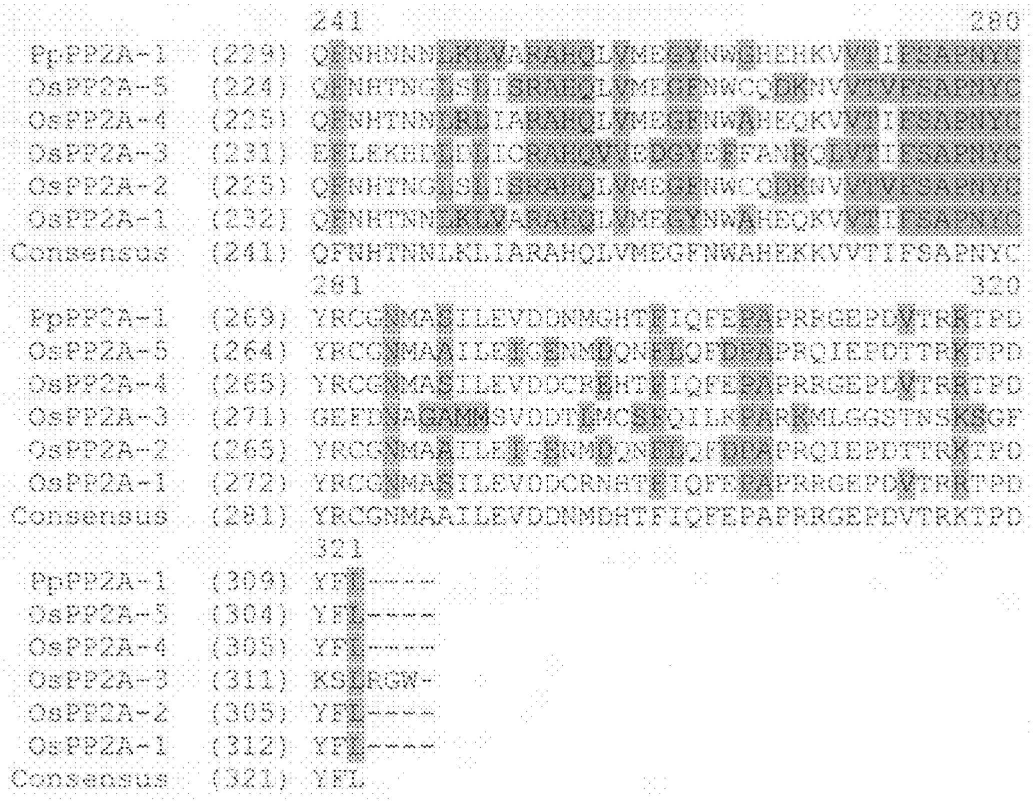
FIG. 2 shows an alignment of the deduced amino acid sequence of PP2A-1 (SEQ ID NO:3) from *Physcomitrella patens* with deduced amino acid sequences of OsPP2A-1 (SEQ ID NO:24), OsPP2A-2 (SEQ ID NO:26), OsPP2A-3 (SEQ ID NO:28), OsPP2A-4 (SEQ ID NO:30), and OsPP2A-5 (SEQ ID NO:32) from *Oryza sativa.*

(SEQ ID NO:14), GmPP2A-2 (SEQ ID NO:16), GmPP2A-3 (SEQ ID NO:18), GmPP2A-4 (SEQ ID NO:20), and GmPP2A-5 (SEQ ID NO:22) from *Glycine max*; and BnPP2A-1 (SEQ ID NO:8), BnPP2A-2 (SEQ ID NO:10), and BnPP2A-3 (SEQ ED NO:12) from *Brassica napus.*

FIG. 4 shows an alignment of the deduced amino acid sequence of PP2A-1 (SEQ ID NO:3) from *Physcomitrella patents* with deduced amino acid sequences of OsPP2A-1 (SEQ ID NO:24), OsPP2A-2 (SEQ ID NO:26), OsPP2A-3 (SEQ ID NO:28), OsPP2A-4 (SEQ ID NO:30), and OsPP2A-5 (SEQ ID NO:32) from *Oryza sativa*. The alignment also includes GmPP2A-1 (SEQ ID NO:14), GmPP2A-2 (SEQ ID NO:16), GmPP2A-3 (SEQ ID NO:18), GmPP2A-4 (SEQ ID NO:20), and GmPP2A-5 (SEQ ID NO:22) from *Glycine max*; and BnPP2A-1 (SEQ ID NO:8), BnPP2A-2 (SEQ ID NO:10), and BnPP2A-3 (SEQ ID NO:12) from *Brassica napus.*

FIG. 5 shows the correlation between the gene name and the SEQ ID NO in the sequence listing.

FIG. 6 shows the degree of amino acid identity and similarity of PpPP2A-1 (SEQ ID NO:3), PpPP-1 (SEQ ID NO:6), BnPp2A-1 (SEQ ID NO:8), BnPP2A-2 (SEQ ID NO:10), BnPP2A-3 (SEQ ID NO:12), GmPp2A-1 (SEQ ED NO:14), GmPP2A-2 (SEQ ID NO:16), GmPP2A-3 (SEQ ID NO:18), GmPP2A-4 (SEQ ID NO:20), GmPP2A-5 (SEQ ID NO:22), OsPP2A-1 (SEQ ID NO:24), OsPP2A-2 (SEQ ID NO:26), OsPP2A-3 (SEQ ID NO:28), OsPP2A-4 (SEQ ID NO:30), and OsPP2A-5 (SEQ ID NO:32). (Pairwise Comparison was used: gap penalty: 10; gap extension penalty: 0.1; score matrix: blosum 62)

DETAILED DESCRIPTION OF THE INVENTION

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as polypeptide "Protein Phosphatase Stress-Related Polypeptides" (PPSRPs), in no way limits the functionality of those sequences.

The present invention describes a novel genus of Protein Phosphatase Stress-Related Polypeptides (PPSRPs) and PPSRP coding nucleic acids that are important for modulating a plant's response to an environmental stress. More particularly, over-expression of these PPSRP coding nucleic acids in a plant results in the plant's increased growth/yield under normal or stress conditions and/or increased tolerance to an environmental stress. Representative members of the PPSRP genus include, but are not limited to, PP2A-1, PP2A-2, PP2A-3, PP2A-4, PP-1, BnPP2A-1, BnPP2A-2, BnPP2A-3, GmPP2A-1, GmPP2A-2, GmPP2A-3, GmPP2A-4, GmPP2A-5, OsPP2A-1, OsPP2A-2, OsPP2A-3, OsPP2A-4, and OsPP2A-5. In a preferred embodiment, all members of the genus are biologically active protein phosphatases. The PP2A-2, PP2A-3, and PP2A-4 polypeptides are described in U.S. patent application Ser. No. 09/828,302, the entire contents of which are hereby incorporated by reference, while PP2A-1, PP-1, BnPP2A-1, BnPP2A-2, BnPP2A-3, GmPP2A-1, GmPP2A-2, GmPP2A-3, GmPP2A-4, GmPP2A-5, OsPP2A-1, OsPP2A-2, OsPP2A-3, OsPP2A-4, and OsPP2A-5 are described herein.

The present invention provides a transgenic plant cell transformed by a PPSRP coding nucleic acid, wherein expression of the nucleic acid sequence in the plant cell results in increased growth/yield under normal or stress conditions and/or increased tolerance to environmental stress as compared to a wild type variety of the plant cell. The invention further provides transgenic plant parts and transgenic plants containing the plant cells described herein. Plant parts include, but are not limited to, stems, roots, ovules, stamens, leaves, embryos, meristematic regions, callus tissue, gametophytes, sporophytes, pollen, microspores and the like. In one embodiment, the transgenic plant is male sterile. Also provided is a plant seed produced by a transgenic plant transformed by a PPSRP coding nucleic acid, wherein the seed contains the PPSRP coding nucleic acid, and wherein the plant is true breeding for increased growth/yield under normal or stress conditions and/or increased tolerance to environmental stress as compared to a wild type variety of the plant. The invention further provides a seed produced by a transgenic plant expressing a PPSRP, wherein the seed contains the PPSRP, and wherein the plant is true breeding for increased growth/yield under normal or stress conditions and/or increased tolerance to environmental stress as compared to a wild type variety of the plant. The invention also provides an agricultural product produced by any of the below-described transgenic plants, plant parts, and plant seeds. Agricultural products include, but are not limited to, plant extracts, proteins, amino acids, carbohydrates, fats, oils, polymers, vitamins, and the like.

As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

The present invention describes for the first time that the *Physcomitrella patens* PPSRPs, PP2A-1 and PP-1; *Brassica napus* PPSRPs, BnPP2A-1, BnPP2A-2, and BnPP2A-3; *Glycine max* PPSRPs, GmPP2A-1, GmPP2A-2, GmPP2A-3, GmPP2A-4, and GmPP2A-5; and *Oryza sativa* PPSRPs, OsPP2A-1, OsPP2A-2, OsPP2A-3, OsPP2A-4, and OsPP2A-5; are useful for increasing a plant's growth/yield under normal or stress conditions and/or tolerance to environmental stress. As used herein, the term polypeptide refers to a chain of at least four amino acids joined by peptide bonds. The chain may be linear, branched, circular or combinations thereof. Accordingly, the present invention provides isolated PPSRPs selected from the group consisting of PP2A-1, PP-1, BnPP2A-1, BnPP2A-2, BnPP2A-3, GmPP2A-1, GmPP2A-2, GmPP2A-3, GmPP2A-4, GmPP2A-5, OsPP2A-1, OsPP2A-2, OsPP2A-3, OsPP2A-4, and OsPP2A-5, and homologs thereof. In preferred embodiments, the PPSRP is selected from: 1) Protein phosphatase 2A-1 (PP2A-1) polypeptide as defined in SEQ ID NO:3; 2) Protein phosphatase-1 (PP-1) polypeptide as defined in SEQ ID NO:6; 3)

*Brassica napus* Protein Phosphatase PP2A-1 (BnPP2A-1) polypeptide as defined in SEQ ID NO:8; 4) BnPP2A-2 polypeptide as defined in SEQ ID NO:10; 5) BnPP2A-3 polypeptide as defined in SEQ ID NO:12; 6) *Glycine max* Protein Phosphatase PP2A-1 (GmPP2A-1) polypeptide as defined in SEQ ID NO:14; 7) GmPP2A-2 polypeptide as defined in SEQ ID NO:16; 8) GmPP2A-3 polypeptide as defined in SEQ ID NO:18; 9) GmPP2A-4 polypeptide as defined in SEQ ID NO:20; 10) GmPP2A-5 polypeptide as defined in SEQ ID NO:22; 11) *Oryza sativa* Protein phosphatase 2A-1 (OsPP2A-1) polypeptide as defined in SEQ ID NO:24; 12) OsPP2A-2 polypeptide as defined in SEQ ID NO:26; 13) OsPP2A-3 polypeptide as defined in SEQ ID NO:28; 14) OsPP2A-4 polypeptide as defined in SEQ ID NO:30; 15) OsPP2A-5 polypeptide as defined in SEQ ID NO:32; and homologs and orthologs thereof. Homologs and orthologs of the amino acid sequences are defined below.

The PPSRPs of the present invention are preferably produced by recombinant DNA techniques. For example, a nucleic acid molecule encoding the polypeptide is cloned into an expression vector (as described below), the expression vector is introduced into a host cell (as described below), and the PPSRP is expressed in the host cell. The PPSRP can then be isolated from the cells by an appropriate purification scheme using standard polypeptide purification techniques. For the purposes of the invention, the term "recombinant polynucleotide" refers to a polynucleotide that has been altered, rearranged, or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. Alternative to recombinant expression, a PPSRP, or peptide can be synthesized chemically using standard peptide synthesis techniques. Moreover, native PPSRP can be isolated from cells (e.g., *Physcomitrella patens, Brassica napus, Glycine max*, or *Oryza sativa*), for example using an anti-PPSRP antibody, which can be produced by standard techniques utilizing a PPSRP or fragment thereof.

The invention further provides an isolated PPSRP coding nucleic acid. The present invention includes PPSRP coding nucleic acids that encode PPSRPs as described herein. In preferred embodiments, the PPSRP coding nucleic acid is selected from: 1) Protein phosphatase 2A-1 (PP2A-1) nucleic acid as defined in SEQ ID NO:2; 2) Protein phosphatase-1 (PP-1) nucleic acid as defined in SEQ ID NO:5; 3) *Brassica napus* Protein Phosphatase PP2A-1 (BnPP2A-1) nucleic acid as defined in SEQ ID NO:7; 4) BnPP2A-2 nucleic acid as defined in SEQ ID NO:9; 5) BnPP2A-3 nucleic acid as defined in SEQ ID NO:11; 6) *Glycine max* Protein Phosphatase PP2A-1 (GmPP2A-1) nucleic acid as defined in SEQ ID NO:13; 7) GmPP2A-2 nucleic acid as defined in SEQ ID NO:15; 8) GmPP2A-3 nucleic acid as defined in SEQ ID NO:17; 9) GmPP2A-4 nucleic acid as defined in SEQ ID NO:19; 10) GmPP2A-5 nucleic acid as defined in SEQ ID NO:21; 11) *Oryza sativa* Protein phosphatase 2A-1 (OsPP2A-1) nucleic acid as defined in SEQ ID NO:23; 12) OsPP2A-2 nucleic acid as defined in SEQ ID NO:25; 13) OsPP2A-3 nucleic acid as defined in SEQ ID NO:27; 14) OsPP2A-4 nucleic acid as defined in SEQ ID NO:29; 15) OsPP2A-5 nucleic acid as defined in SEQ ID NO:31; and homologs and orthologs thereof. Homologs and orthologs of the nucleotide sequences are defined below. In one preferred embodiment, the nucleic acid and polypeptide are isolated from the plant genus *Physcomitrella, Brassica, Glycine*, or *Oryza*. In another preferred embodiment, the nucleic acid and polypeptide are from a *Physcomitrella patens* (*P. patens*) plant, a *Brassica napus* plant, a *Glycine max* plant, or an *Oryza sativa* plant.

As used herein, the term "environmental stress" refers to any sub-optimal growing condition and includes, but is not limited to, sub-optimal conditions associated with salinity, drought, nitrogen, temperature, metal, chemical, pathogenic and oxidative stresses, or combinations thereof. In preferred embodiments, the environmental stress can be salinity, drought, or temperature, or combinations thereof, and in particular, can be high salinity, low water content or low temperature. It is also to be understood that as used in the specification and in the claims, "a" or "an" can mean one or more, depending upon the context in which it is used. Thus, for example, reference to "a cell" can mean that at least one cell can be utilized.

As also used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR and in vitro or in vivo transcription.

An "isolated" nucleic acid molecule is one that is substantially separated from other nucleic acid molecules that are present in the natural source of the nucleic acid (i.e., sequences encoding other polypeptides). Preferably, an "isolated" nucleic acid is free of some of the sequences that naturally flank the nucleic acid (i.e., sequences located at the 5' and 3' ends of the nucleic acid) in its naturally occurring replicon. For example, a cloned nucleic acid is considered isolated. In various embodiments, the isolated PPSRP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Physcomitrella patens*, a *Brassica napus*, a *Glycine max*, or an *Oryza sativa* cell). A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparations or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule having a nucleotide sequence of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, or a portion thereof, can be isolated using standard molecular biology techniques and the sequence information provided herein. For example, a *P. patens* PPSRP cDNA can be isolated from a *P. patens* library using all or portion of one of the sequences of SEQ ID NO:1 and SEQ ID NO:4. Moreover, a nucleic acid molecule encompassing all or a portion of one of the sequences of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979 Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:2, SEQ ID NO:5. SEQ ID NO:7, SEQ ID NO:9, SEQ ID NO:11, SEQ ID NO:13, SEQ ID NO:15, SEQ ED NO:17, SEQ ID NO:19, SEQ ID NO:21, SEQ ID NO:23, SEQ ID NO:25, SEQ ID NO:27, SEQ ID NO:29, or SEQ ID NO:31. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a PPSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:2, SEQ ID NO:5, SEQ ID NO:7, SEQ ID NO:9, SEQ ED NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31. These cDNAs comprise sequences encoding the PPSRPs, (i.e., the "coding region"), as well as 5' untranslated sequences and 3' untranslated sequences. It is to be understood that SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31 may comprise both coding regions and 5' and 3' untranslated regions. Alternatively, the nucleic acid molecules of the present invention can comprise only the coding region of any of the sequences in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, or can contain whole genomic fragments isolated from genomic DNA. The present invention also includes PPSRP coding nucleic acids that encode PPSRPs as described herein. Preferred is a PPSRP coding nucleic acid that encodes a PPSRP selected from the group consisting of PP2A-1 (SEQ ID NO:3), PP-1 (SEQ ID NO:6), BnPP2A-1 (SEQ ID NO:8), BnPP2A-2 (SEQ ID NO:10), BnPP2A-3 (SEQ ID NO:12), GmPP2A-1 (SEQ ID NO:14), GmPP2A-2 (SEQ ID NO:16), GmPP2A-3 (SEQ ID NO:18), GmPP2A-4 (SEQ ID NO:20), GmPP2A-4 (SEQ ID NO:22), OsPP2A-1 (SEQ ID NO:24), OsPP2A-2 (SEQ ID NO:26), OsPP2A-3 (SEQ ID NO:28), OsPP2A-4 (SEQ ED NO:30), and OsPP2A-5 (SEQ ID NO:32).

Moreover, the nucleic acid molecule of the invention can comprise only a portion of the coding region of one of the sequences in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, for example, a fragment that can be used as a probe or primer or a fragment encoding a biologically active portion of a PPSRP. The nucleotide sequences determined from the cloning of the PPSRP genes from *P. patens, B. napus, G. max*, and *O. sativa* allow for the generation of probes and primers designed for use in identifying and/or cloning PPSRP homologs in other cell types and organisms, as well as PPSRP homologs from other mosses and related species. The portion of the coding region can also encode a biologically active fragment of a PPSRP.

As used herein, the term "biologically active portion of" a PPSRP is intended to include a portion, e.g., a domain/motif, of a PPSRP that participates in modulation of stress tolerance in a plant, and more preferably, drought tolerance or salt tolerance. For the purposes of the present invention, modulation of stress tolerance refers to at least a 10% increase or decrease in the stress tolerance of a transgenic plant comprising a PPSRP expression cassette (or expression vector) as compared to the stress tolerance of a non-transgenic control plant. Methods for quantitating stress tolerance are provided at least in Example 7 below. In a preferred embodiment, the biologically active portion of a PPSRP increases a plant's tolerance to an environmental stress.

Biologically active portions of a PPSRP include peptides comprising amino acid sequences derived from the amino acid sequence of a PPSRP (e.g., an amino acid sequence of SEQ ID NO:3, SEQ ED NO:6, SEQ ID NO:8, SEQ ID NO:10, SEQ ID NO:12, SEQ ED NO:14, SEQ ID NO:16, SEQ ED NO:18, SEQ ID NO:20, SEQ ID NO:22, SEQ ID NO:24, SEQ ID NO:26, SEQ ID NO:28, SEQ ID NO:30, and SEQ ID NO:32) or the amino acid sequence of a polypeptide identical to a PPSRP, which include fewer amino acids than a full length PPSRP or the full length polypeptide which is identical to a PPSRP, and exhibit at least one activity of a PPSRP. Typically, biologically active portions (e.g., peptides which are, for example, 5, 10, 15, 20, 30, 35, 36, 37, 38, 39, 40, 50, 100 or more amino acids in length) comprise a domain or motif with at least one activity of a PPSRP. Moreover, other biologically active portions in which other regions of the polypeptide are deleted, can be prepared by recombinant techniques and evaluated for one or more of the activities described herein. Preferably, the biologically active portions of a PPSRP include one or more selected domains/motifs or portions thereof having biological activity.

The invention also provides PPSRP chimeric or fusion polypeptides. As used herein, a PPSRP "chimeric polypeptide" or "fusion polypeptide" comprises a PPSRP operatively linked to a non-PPSRP. A PPSRP refers to a polypeptide having an amino acid sequence corresponding to a PPSRP, whereas a non-PPSRP refers to a polypeptide having an amino acid sequence corresponding to a polypeptide which is not substantially identical to the PPSRP, e.g., a polypeptide that is different from the PPSRP and is derived from the same or a different organism. Within the fusion polypeptide, the term "operatively linked" is intended to indicate that the PPSRP and the non-PPSRP are fused to each other so that both sequences fulfill the proposed function attributed to the sequence used. The non-PPSRP can be fused to the N-terminus or C-terminus of the PPSRP. For example, in one embodiment, the fusion polypeptide is a GST-PPSRP fusion polypeptide in which the PPSRP sequences are fused to the C-terminus of the GST sequences. Such fusion polypeptides can facilitate the purification of recombinant PPSRPs. In another embodiment, the fusion polypeptide is a PPSRP containing a heterologous signal sequence at its N-terminus. In certain host cells (e.g., mammalian host cells), expression and/or secretion of a PPSRP can be increased through use of a heterologous signal sequence.

Preferably, a PPSRP chimeric or fusion polypeptide of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Current Protocols in Molecular Biology, Eds. Ausubel et al. John Wiley & Sons: 1992). Moreover, many expression vectors are commercially available that already encode a fusion moiety (e.g., a GST polypeptide). A PPSRP encoding nucleic acid can be cloned into such an expression vector such that the fusion moiety is linked in-frame to the PPSRP.

In addition to fragments and fusion polypeptides of the PPSRPs described herein, the present invention includes homologs and analogs of naturally occurring PPSRPs and PPSRP encoding nucleic acids in a plant. "Homologs" are defined herein as two nucleic acids or polypeptides that have similar, or "identical," nucleotide or amino acid sequences, respectively. Homologs include allelic variants, orthologs, paralogs, agonists, and antagonists of PPSRPs as defined hereafter. The term "homolog" further encompasses nucleic acid molecules that differ from one of the nucleotide sequences shown in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31 (and portions thereof) due to degeneracy of the genetic code and thus encode the same PPSRP as that encoded by the nucleotide sequences shown in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ED NO:19, SEQ ID NO:21, SEQ ID NO:23, SEQ ID NO:25, SEQ ID NO:27, SEQ ID NO:29, and SEQ ID NO:31. As used herein a "naturally occurring" PPSRP refers to a PPSRP amino acid sequence that occurs in nature. Preferably, a naturally occurring PPSRP comprises an amino acid sequence selected from the group consisting of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32.

An agonist of the PPSRP can retain substantially the same, or a subset, of the biological activities of the PPSRP. An antagonist of the PPSRP can inhibit one or more of the activities of the naturally occurring form of the PPSRP. For example, the PPSRP antagonist can competitively bind to a downstream or upstream member of the cell membrane component metabolic cascade that includes the PPSRP, or bind to a PPSRP that mediates transport of compounds across such membranes, thereby preventing translocation from taking place.

Nucleic acid molecules corresponding to natural allelic variants and analogs, orthologs, and paralogs of a PPSRP cDNA can be isolated based on their identity to the *Physcomitrella patens, Brassica napus, Glycine max*, or *Oryza sativa* PPSRP nucleic acids described herein using PPSRP cDNAs, or a portion thereof, as a hybridization probe according to standard hybridization techniques under stringent hybridization conditions. In an alternative embodiment, homologs of the PPSRP can be identified by screening combinatorial libraries of mutants, e.g., truncation mutants, of the PPSRP for PPSRP agonist or antagonist activity. In one embodiment, a variegated library of PPSRP variants is generated by combinatorial mutagenesis at the nucleic acid level and is encoded by a variegated gene library. A variegated library of PPSRP variants can be produced by, for example, enzymatically ligating a mixture of synthetic oligonucleotides into gene sequences such that a degenerate set of potential PPSRP sequences is expressible as individual polypeptides, or alternatively, as a set of larger fusion polypeptides (e.g., for phage display) containing the set of PPSRP sequences therein. There are a variety of methods that can be used to produce libraries of potential PPSRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential PPSRP sequences. Methods for synthesizing degenerate oligonucleotides are known in the art (see, e.g., Narang, S. A., 1983 Tetrahedron 39:3; Itakura et al., 1984 Annu. Rev. Biochem. 53:323; Itakura et al., 1984 Science 198:1056; Ike et al., 1983 Nucleic Acid Res. 11:477).

In addition, libraries of fragments of the PPSRP coding regions can be used to generate a variegated population of PPSRP fragments for screening and subsequent selection of homologs of a PPSRP. In one embodiment, a library of coding sequence fragments can be generated by treating a double stranded PCR fragment of a PPSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PPSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PPSRP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify PPSRP homologs (Arkin and Yourvan, 1992 PNAS 89:7811-1815; Delgrave et al., 1993 Polypeptide Engineering 6(3):327-331). In another embodiment, cell based assays can be exploited to analyze a variegated PPSRP library, using methods well known in the art. The present invention further provides a method of identifying a novel PPSRP, comprising (a) raising a specific antibody response to a PPSRP, or a fragment thereof, as described herein; (b) screening putative PPSRP material with the antibody, wherein specific binding of the antibody to the material indicates the presence of a potentially novel PPSRP; and (c) analyzing the bound material in comparison to a known PPSRP, to determine its novelty.

As stated above, the present invention includes PPSRPs and homologs thereof. To determine the percent sequence identity of two amino acid sequences (e.g., one of the sequences of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32, and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., one of the sequences of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32) is occupied by the same amino acid residue as the corresponding position in the other sequence (e.g., a mutant form of the sequence selected from the polypeptide of SEQ ID NO:3, SEQ ID NO:6, SEQ ED NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32), then the molecules are identical at that position. The same type of comparison can be made between two nucleic acid sequences.

The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90% or 90-95%, and most preferably at least about 96%, 97%, 98%, 99% or more identical to an entire amino acid sequence shown in SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ED NO:28, SEQ ID NO:30, and SEQ ID NO:32. In yet another embodiment, the isolated amino acid homologs included in the present invention are at least about 50-60%, preferably at least about 60-70%, and more preferably at least about 70-75%, 75-80%, 80-85%, 85-90% or 90-95%, and most preferably at least about 96%, 97%, 98%, 99% or more identical to an entire amino acid sequence encoded by a nucleic acid sequence shown in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. In other embodiments, the PPSRP amino acid homologs have sequence identity over at least 15 contiguous amino acid residues, more preferably at least 25 contiguous amino acid residues, and most preferably at least 35 contiguous amino acid residues of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32.

In another preferred embodiment, an isolated nucleic acid homolog of the invention comprises a nucleotide sequence which is at least about 50-60%, preferably at least about 60-70%, more preferably at least about 70-75%, 75-80%, 80-85%, 85-90% or 95-95%, and even more preferably at least about 95%, 96%, 97%, 98%, 99% or more identical to a nucleotide sequence shown in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, or to a portion comprising at least 60 consecutive nucleotides thereof. The preferable length of sequence comparison for nucleic acids is at least 75 nucleotides, more preferably at least 100 nucleotides and most preferably the entire length of the coding region.

It is further preferred that the isolated nucleic acid homolog of the invention encodes a PPSRP, or portion thereof, that is at least 70% identical to an amino acid sequence of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32, and that functions as a modulator of an environmental stress response in a plant. In a more preferred embodiment, overexpression of the nucleic acid homolog in a plant increases the tolerance of the plant to an environmental stress. In a further preferred embodiment, the nucleic acid homolog encodes a PPSRP that functions as a protein phosphatase.

For the purposes of the invention, the percent sequence identity between two nucleic acid or polypeptide sequences is determined using the Vector NTI 9.0 (PC) software package (Invitrogen, 1600 Faraday Ave., Carlsbad, Calif. 92008). A gap-opening penalty of 15 and a gap extension penalty of 6.66 are used for determining the percent identity of two nucleic acids. A gap-opening penalty of 10 and a gap extension penalty of 0.1 are used for determining the percent identity of two polypeptides. All other parameters are set at the default settings. For purposes of a multiple alignment (Clustal W algorithm), the gap-opening penalty is 10, and the gap extension penalty is 0.05 with blosum 62 matrix. It is to be understood that for the purposes of determining sequence identity when comparing a DNA sequence to an RNA sequence, a thymidine nucleotide is equivalent to a uracil nucleotide.

In another aspect, the invention provides an isolated nucleic acid comprising a polynucleotide that hybridizes to the polynucleotide of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 under stringent conditions. More particularly, an isolated nucleic acid molecule of the invention is at least 15 nucleotides in length and hybridizes under stringent conditions to the nucleic acid molecule comprising a nucleotide sequence of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. In other embodiments, the nucleic acid is at least 30, 50, 100, 250 or more nucleotides in length. Preferably, an isolated nucleic acid homolog of the invention comprises a nucleotide sequence which hybridizes under highly stringent conditions to the nucleotide sequence shown in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 and functions as a modulator of stress tolerance in a plant. In a further preferred embodiment, over expression of the isolated nucleic acid homolog in a plant increases a plant's tolerance to an environmental stress. In an even further preferred embodiment, the isolated nucleic acid homolog encodes a PPSRP that functions as a protein phosphatase.

As used herein with regard to hybridization for DNA to DNA blot, the term "stringent conditions" refers to hybridization overnight at 60° C. in 10× Denhart's solution, 6×SSC, 0.5% SDS and 100 μg/ml denatured salmon sperm DNA. Blots are washed sequentially at 62° C. for 30 minutes each time in 3×SSC/0.1% SDS, followed by 1×SSC/0.1% SDS and finally 0.1×SSC/0.1%SDS. As also used herein, "highly stringent conditions" refers to hybridization overnight at 65° C. in 10× Denhart's solution, 6×SSC, 0.5% SDS and 100 μg/ml denatured salmon sperm DNA. Blots are washed sequentially at 65° C. for 30 minutes each time in 3×SSC/0.1% SDS, followed by 10×SSC/0.1% SDS and finally 0.1×SSC/0.1% SDS. Methods for nucleic acid hybridizations are described in Meinkoth and Wahl (1984) Anal. Biochem. 138: 267-284; Current Protocols in Molecular Biology, Chapter 2, Ausubel et al. Eds., Greene Publishing and Wiley-Interscience, New York, 1995; and Tijssen, Laboratory Techniques in Biochemistry and Molecular Biology: Hybridization with Nucleic Acid Probes, Part I, Chapter 2, Elsevier, New York, 1993. Preferably, an isolated nucleic acid molecule of the invention that hybridizes under stringent or highly stringent conditions to a sequence of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 corresponds to a naturally occurring nucleic acid molecule. As used herein, a "naturally occurring" nucleic acid molecule refers to an RNA or DNA molecule having a nucleotide sequence that occurs in nature (e.g., encodes a natural polypeptide). In one embodiment, the nucleic acid encodes a naturally occurring *Physcomitrella patens* PPSRP, *Brassica napus* PPSRP, *Glycine max* PPSRP, or *Oryza sativa* PPSRP.

Using the above-described methods, and others known to those of skill in the art, one of ordinary skill in the art can isolate homologs of the PPSRPs comprising amino acid sequences shown in SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. One subset of these homologs is allelic variants. As used herein, the term "allelic variant" refers to a nucleotide sequence containing polymorphisms that lead to changes in the amino acid sequences of a PPSRP and that exist within a natural population (e.g., a plant species or variety). Such natural allelic variations can typically result in 1-5% variance in a PPSRP nucleic acid. Allelic variants can be identified by sequencing the nucleic acid sequence of interest in a number of different plants, which can be readily carried out by using hybridization probes to identify the same PPSRP genetic locus in those plants. Any and all such nucleic acid variations and resulting amino acid polymorphisms or variations in a PPSRP that are the result of natural allelic variation and that do not alter the functional activity of a PPSRP, are intended to be within the scope of the invention.

Moreover, nucleic acid molecules encoding PPSRPs from the same or other species, such as PPSRP analogs, orthologs, and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by specification. Normally, orthologs encode polypeptides having the same or similar functions. As also used herein, the term "paralogs" refers to two nucleic acids that are related by duplication within a genome. Paralogs usually have different functions, but these functions may be related (Tatusov, R. L. et al. 1997 Science 278(5338):631-637). Analogs, orthologs, and paralogs of a naturally occurring PPSRP can differ from the naturally occurring PPSRP by post-translational modifications, by amino acid sequence differences, or by both. Post-translational modifications include ill vivo and ill vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably, 85-90% or 90-95%, and most preferably 95%, 96%, 97%, 98% or even 99% identity or sequence identity with all or part of a naturally occurring PPSRP amino acid sequence and will exhibit a function similar to a PPSRP. Preferably, a PPSRP ortholog of the present invention functions as a modulator of an environmental stress response in a plant and/or functions as a protein phosphatase. More preferably, a PPSRP ortholog increases the stress tolerance of a plant. In one embodiment, the PPSRP orthologs maintain the ability to participate in the metabolism of compounds necessary for the constriction of cellular membranes in a plant, or in the transport of molecules across these membranes.

In addition to naturally-occurring variants of a PPSRP sequence that may exist in the population, the skilled artisan will further appreciate that changes can be introduced by mutation into a nucleotide sequence of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32, thereby leading to changes in the amino acid sequence of the encoded PPSRP, without altering the functional activity of the PPSRP. For example, nucleotide substitutions leading to amino acid substitutions at "non-essential" amino acid residues can be made in a sequence of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. A "non-essential" amino acid residue is a residue that can be altered from the wild-type sequence of one of the PPSRPs without altering the activity of said PPSRP, whereas an "essential" amino acid residue is required for PPSRP activity. Other amino acid residues, however, (e.g., those that are not conserved or only semi-conserved in the domain having PPSRP activity) may not be essential for activity and thus are likely to be amenable to alteration without altering PPSRP activity.

Accordingly, another aspect of the invention pertains to nucleic acid molecules encoding PPSRPs that contain changes in amino acid residues that are not essential for PPSRP activity. Such PPSRPs differ in amino acid sequence from a sequence contained in SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32, yet retain at least one of the PPSRP activities described herein. In one embodiment, the isolated nucleic acid molecule comprises a nucleotide sequence encoding a polypeptide, wherein the polypeptide comprises an amino acid sequence at least about 50% identical to an amino acid sequence of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. Preferably, the polypeptide encoded by the nucleic acid molecule is at least about 50-60% identical to one of the sequences of SEQ ID NO:3, SEQ ID NO:6, SEQ ED NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32; more preferably at least about 60-70% identical to one of the sequences of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32; even more preferably at least about 70-75%, 75-80%, 80-85%, 85-90%, 90-95% identical to one of the sequences of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32; and most preferably at least about 96%, 97%, 98%, or 99% identical to one of the sequences of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32. The preferred PPSRP homologs of the present invention preferably participate in the a stress tolerance response in a plant, or more particularly, participate in the transcription of a polypeptide involved in a stress tolerance response in a plant, and/or function as a protein phosphatase.

An isolated nucleic acid molecule encoding a PPSRP having sequence identity with a polypeptide sequence of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32 can be created by introducing one or more nucleotide substitutions, additions or deletions into a nucleotide sequence of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, respectively, such that one or more amino acid substitutions, additions or deletions are introduced into the encoded polypeptide. Mutations can be introduced into one of the sequences of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PPSRP is preferably replaced with another amino acid residue from the same side chain family. Alternatively, in another embodiment, mutations can be introduced randomly along all or part of a PPSRP coding sequence, such as by saturation mutagenesis, and the resultant mutants can be screened for a PPSRP activity described herein to identify mutants that retain PPSRP activity. Following mutagenesis of one of the sequences of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, the encoded polypeptide can be expressed recombinantly and the activity of the polypeptide can be determined by analyzing the stress tolerance of a plant expressing the polypeptide as described in Example 7.

Additionally, optimized PPSRP nucleic acids can be created. Preferably, an optimized PPSRP nucleic acid encodes a PPSRP that binds to a phosphate group and/or modulates a plant's growth/yield under normal or stress conditions and/or tolerance to an environmental stress, and more preferably increases a plant's growth/yield under normal or stress conditions and/or tolerance to an environmental stress upon its over-expression in the plant. As used herein, "optimized" refers to a nucleic acid that is genetically engineered to increase its expression in a given plant or animal. To provide plant optimized PPSRP nucleic acids, the DNA sequence of the gene can be modified to 1) comprise codons preferred by highly expressed plant genes; 2) comprise an A+T content in nucleotide base composition to that substantially found in plants; 3) form a plant initiation sequence, 4) to eliminate sequences that cause destabilization, inappropriate polyadenylation, degradation and termination of RNA, or that form secondary structure hairpins or RNA splice sites. Increased expression of PPSRP nucleic acids in plants can be achieved by utilizing the distribution frequency of codon usage in plants in general or a particular plant. Methods for optimizing nucleic acid expression in plants can be found in EPA 0359472; EPA 0385962; WO 91/16432; U.S. Pat. Nos. 5,380,831; 5,436,391; Perlack et al. (1991) Proc. Natl. Acad. Sci. USA 88:3324-3328; and Murray et al. (1989) Nucleic Acids Res. 17:477-498.

A PPSRP nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized PPSRP nucleic acids of this invention also preferably have CG and TA doublet avoidance indices closely approximating those of the chosen host plant (i.e., *Physcomitrella patens, Brassica napus, Glycine max*, or *Oryza sativa*). More preferably these indices deviate from that of the host by no more than about 10-15%.

In addition to the nucleic acid molecules encoding the PPSRPs described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32.

The antisense nucleic acid can be complementary to an entire PPSRP coding strand, or to only a portion thereof. In one embodiment, an antisense nucleic acid molecule is antisense to a "coding region" of the coding strand of a nucleotide sequence encoding a PPSRP. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding a PPSRP. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of PPSRP mRNA, but more preferably is an oligonucleotide that is antisense to only a portion of the coding or noncoding region of PPSRP mRNA. For example, the antisense oligonucleotide can be complementary to the region surrounding the translation start site of PPSRP mRNA. An antisense oligonucleotide can be, for example, about 5, 10, 15, 20, 25, 30, 35, 40, 45 or 50 nucleotides in length. Typically, the antisense molecules of the present invention comprise an RNA having 60-100% sequence identity with at least 14 consecutive nucleotides of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31; or a polynucleotide encoding a polypeptide of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. Preferably, the sequence identity will be at least 70%, more preferably at least 75%, 80%, 85%, 90%, 95%, 98% and most preferably 99%.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987 Nucleic Acids. Res. 15:6625-6641). The antisense nucleic acid molecule can also comprise a 2'-o-methylribonucleotide (Inoue et al., 1987 Nucleic Acids Res. 15:6131-6148) or a chimeric RNA-DNA analogue (Inoue et al., 1987 FEBS Lett. 215:327-330).

The antisense nucleic acid molecules of the invention are typically administered to a cell or generated in situ such that they hybridize with or bind to cellular mRNA and/or genomic DNA encoding a PPSRP to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides or double stranded RNA (dsRNA) can be used to reduce expression of a PPSRP polypeptide. By "ribozyme" is meant a catalytic RNA-based enzyme with ribonuclease activity, which is capable of cleaving a single-stranded nucleic acid, such as an mRNA, to which it has a complementary region. Ribozymes (e.g., hammerhead ribozymes described in Haselhoff and Gerlach, 1988 Nature 334:585-591) can be used to catalytically cleave PPSRP mRNA transcripts to thereby inhibit translation of PPSRP mRNA. A ribozyme having specificity for a PPSRP-encoding nucleic acid can be designed based upon the nucleotide sequence of a PPSRP cDNA, as disclosed herein (i.e., SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31), or on the basis of a heterologous sequence to be isolated according to methods taught in this invention. For example, a derivative of a *Tetrahymena* L-19 IVS RNA can be constructed in which the nucleotide sequence of the active site is complementary to the nucleotide sequence to be cleaved in a PPSRP-encoding mRNA. See, e.g., Cech et al. U.S. Pat. No. 4,987,071 and Cech et al. U.S. Pat. No. 5,116,742. Alternatively, PPSRP mRNA can be used to select a catalytic RNA having a specific ribonuclease activity from a pool of RNA molecules. See, e.g., Bartel, D. and Szostak, J. W., 1993 Science 261:1411-1418. In preferred embodiments, the ribozyme will contain a portion having at least 7, 8, 9, 10, 12, 14, 16, 18 or 20 nucleotides, and more preferably 7 or 8 nucleotides, that have 100% complementarity to a portion of the target RNA. Methods for making ribozymes are known to those skilled in the art. See, for example, U.S. Pat. Nos. 6,025,167; 5,773,260 and 5,496,698.

The term "dsRNA," as used herein, refers to RNA hybrids comprising two strands of RNA. The dsRNAs can be linear or circular in structure. In a preferred embodiment, dsRNA is specific for a polynucleotide encoding either the polypeptide of SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32; or a polypeptide having at least 80% sequence identity with SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. The hybridizing RNAs may be substantially or completely complementary. By "substantially complementary," is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3' ends and no gaps. However, dsRNAs having 5' or 3' overhangs of up to 100 nucleotides may be used in the methods of the invention.

The dsRNA may comprise ribonucleotides or ribonucleotide analogs, such as 2'-O-methyl ribosyl residues or combinations thereof. See U.S. Pat. Nos. 4,130,641 and 4,024,222. A dsRNA polyriboinosinic acid:polyribocytidylic acid is described in U.S. Pat. No. 4,283,393. Methods for making and using dsRNA are known in the art. One method comprises the simultaneous transcription of two complementary DNA strands, either in vivo, or in a single in vitro reaction mixture. See, for example, U.S. Pat. No. 5,795,715. dsRNA can be introduced into a plant or plant cell directly by standard transformation procedures. Alternatively, dsRNA can be expressed in a plant cell by transcribing two complementary RNAs.

Other methods for the inhibition of endogenous gene expression, such as triple helix formation (Moser et. al (1987) *Science* 238:645-650 and Cooney et al. (1988) *Science* 241:456-459) and cosuppression (Napoli et al. (1990) *The Plant Cell* 2:279-289) are known in the art. Partial and full-length cDNAs have been used for the cosuppression of endogenous plant genes. See, for example, U.S. Pat. Nos. 4,801,340, 5,034,323, 5,231,020 and 5,283,184, Van der Kroll et al. (1990) *The Plant Cell* 2:29.1-299, Smith et al. (1990) *Mol Gen Genetics* 224:477-481 and Napoli et al. (1990) *The Plant Cell* 2:279-289.

For sense suppression, it is believed that introduction of a sense polynucleotide blocks transcription of the corresponding target gene. The sense polynucleotide will have at least 65% sequence identity with the target plant gene or RNA. Preferably, the percent identity is at least 80%, 90%, 95% or more. The introduced sense polynucleotide need not be full length relative to the target gene or transcript. Preferably, the sense polynucleotide will have at least 65% sequence identity with at least 100 consecutive nucleotides of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. The regions of identity can comprise introns and and/or exons and untranslated regions. The introduced sense polynucleotide may be present in the plant cell transiently, or may be stably integrated into a plant chromosome or extrachromosomal replicon.

Alternatively, PPSRP gene expression can be inhibited by targeting nucleotide sequences complementary to the regulatory region of a PPSRP nucleotide sequence (e.g., a PPSRP promoter and/or enhancer) to form triple helical structures that prevent transcription of a PPSRP gene in target cells. See generally, Helene, C., 1991 Anticancer Drug Des. 6(6):569-84; Helene, C. et al., 1992 Ann. N.Y. Acad. Sci. 660:27-36; and Maher, L. J., 1992 Bioassays 14(12):807-15.

In addition to the PPSRP nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the sequences set forth in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31; an anti-sense sequence of one of the sequences set forth in SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31; or naturally occurring mutants thereof. Primers based on a nucleotide sequence of SEQ ID NO:2, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 can be used in PCR reactions to clone PPSRP homologs. Probes based on the PPSRP nucleotide sequences can be used to detect transcripts or genomic sequences encoding the same or substantially identical polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a PPSRP, such as by measuring a level of a PPSRP-encoding nucleic acid, in a sample of cells, e.g., detecting PPSRP mRNA levels or determining whether a genomic PPSRP gene has been mutated or deleted.

In particular, a useful method to ascertain the level of transcription of the gene (an indicator of the amount of mRNA available for translation to the gene product) is to perform a Northern blot (for reference see, for example, Ausubel et al., 1988 Current Protocols in Molecular Biology, Wiley: New York). This information at least partially demonstrates the degree of transcription of the transformed gene. Total cellular RNA can be prepared from cells, tissues or organs by several methods, all well-known in the art, such as that described in Bormann, E. R. et al., 1992 Mol. Microbiol. 6:317-326. To assess the presence or relative quantity of polypeptide translated from this mRNA, standard techniques, such as a Western blot, may be employed. These techniques are well known to one of ordinary skill in the art. (See, for example, Ausubel et al., 1988 Current Protocols in Molecular Biology, Wiley: New York).

The invention further provides an isolated recombinant expression vector comprising a PPSRP nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., PPSRPs, mutant forms of PPSRPs, fusion polypeptides, etc.).

The recombinant expression vectors of the invention can be designed for expression of PPSRPs in prokaryotic or eukaryotic cells. For example, PPSRP genes can be expressed in bacterial cells such as *C. glutamicum*, insect cells (using baculovirus expression vectors), yeast and other fungal cells (see Romanos, M. A. et al., 1992 Foreign gene expression in yeast: a review, Yeast 8:423-488; van den Hondel, C. A. M. J. J. et al., 1991 Heterologous gene expression in filamentous fungi, in: More Gene Manipulations in Fungi, J. W. Bennet & L. L. Lasure, eds., p. 396-428: Academic Press: San Diego; and van den Hondel, C. A. M. J. J. & Punt, P. J., 1991 Gene transfer systems and vector development for filamentous fungi, in: Applied Molecular Genetics of Fungi, Peberdy, J. F. et al., eds., p. 1-28, Cambridge University Press: Cambridge), algae (Falciatore et al., 1999 Marine Biotechnology 1(3):239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella*, and *Stylonychia*, especially of the genus *Stylonychia lemnae* with vectors following a transformation method as described in PCT Application No. WO 98/01572 and multicellular plant cells (see Schmidt, R. and Willmitzer, L., 1988 High efficiency *Agrobacterium tumefaciens*-mediated transformation of *Arabidopsis thaliana* leaf and cotyledon explants, Plant Cell Rep. 583-586; Plant Molecular Biology and Biotechnology, C Press, Boca Raton, Fla., chapter 6/7, S.71-1.19 (1993); F. F. White, B. Jenes et al., Techniques for Gene Transfer, in: Transgenic Plants, Vol. 1, Engineering and Utilization, eds. Kung und R. Wu, 128-43, Academic Press: 1993; Potrykus, 1991 Annu. Rev. Plant Physiol. Plant Molec. Biol. 42:205-225 and references cited therein) or mammalian cells. Suitable host cells are discussed further in Goeddel, *Genie Expression Technology: Methods in Enzymology* 185, Academic Press: San Diego, Calif. (1990). Alternatively, the recombinant expression vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion vectors typically serve three purposes: 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin, and enterokinase.

Typical fusion expression vectors include pGEX (Pharmacia Biotech Inc; Smith, D. B. and Johnson, K. S., 1988 Gene 67:31-40), pMAL (New England Biolabs, Beverly, Mass.) and pRIT5 (Pharmacia, Piscataway, N.J.) which fuse glutathione S-transferase (GST), maltose E binding polypeptide, or polypeptide A, respectively, to the target recombinant polypeptide. In one embodiment, the coding sequence of the PPSRP is cloned into a pGEX expression vector to create a vector encoding a fusion polypeptide comprising, from the N-terminus to the C-terminus, GST-thrombin cleavage site-X polypeptide. The fusion polypeptide can be purified by affinity chromatography using glutathione-agarose resin. Recombinant PPSRP unfused to GST can be recovered by cleavage of the fusion polypeptide with thrombin.

Examples of suitable inducible non-fusion *E. coli* expression vectors include pTrc (Amann et al., 1988 Gene 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant polypeptide expression is to express the polypeptide in a host bacteria with an impaired capacity to proteolytically cleave the recombinant polypeptide (Gottesman, S., *Gene Expression Technology: Methods in Enzymology* 185, Academic Press, San Diego, Calif. (1990) 119-128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992 Nucleic Acids Res. 20:2111-2118). Such alteration of nucleic acid sequences of the invention can be carried out by standard DNA synthesis techniques.

In another embodiment, the PPSRP expression vector is a yeast expression vector. Examples of vectors for expression in yeast *S. cerevisaie* include pYepSec1 (Baldari, et al., 1987 EMBO J. 6:229-234), pMFa (Kurdan and Herskowitz, 1982 Cell 30:933-943), pJRY88 (Schultz et al., 1987 Gene 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi," in: Applied Molecular Genetics of Fungi, J. F. Peberdy, et al., eds., p. 1-28, Cambridge University Press: Cambridge.

In a preferred embodiment of the present invention, the PPSRPs are expressed in plants and plants cells such as unicellular plant cells (such as algae) (see Falciatore et al., 1999 Marine Biotechnology 1(3):239-251 and references therein) and plant cells from higher plants (e.g., the spermatophytes, such as crop plants). A PPSRP may be "introduced" into a plant cell by any means, including transfection, transformation or transduction, electroporation, particle bombardment, agroinfection and the like.

Suitable methods for transforming or transfecting host cells including plant cells can be found in Sambrook, et al. (Molecular Cloning: A Laboratory Manual. latest ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses and forage crops, these crop plants are also preferred target plants for a genetic engineering as one further embodiment of the present invention. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of a PPSRP into a plant is achieved by *Agrobacterium* mediated gene transfer. *Agrobacterium* mediated plant transformation can be performed using for example the GV3101 (pMP90)

(Koncz and Schell, 1986 Mol. Gen. Genet. 204:383-396) or LBA4404 (Clontech) *Agrobacterium tumefaciens* strain. Transformation can be performed by standard transformation and regeneration techniques (Deblaere et al., 1994 Nucl. Acids. Res. 13:4777-4788; Gelvin, Stanton B. and Schilperoort, Robert A, Plant Molecular Biology Manual, $2^{nd}$ Ed.—Dordrecht: Kluwer Academic Publ., 1995.—in Sect., Ringbuc Zentrale Signatur: BT11-P ISBN 0-7923-2731-4; Glick, Bernard R.; Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989 Plant cell Report 8:238-242; De Block et al., 1989 Plant Physiol. 91:694-701). Use of antibiotics for *Agrobacterium* and plant selection depends on the binary vector and the *Agrobacterium* strain used for transformation. *Agrobacterium* mediated gene transfer to flax can be performed using, for example, a technique described by Mlynarova et al., 1994 Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543 or 5,169,770. Transformation of maize can be achieved by particle bombardment, polyethylene glycol mediated DNA uptake or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387 and a specific example of wheat transformation can be found in PCT Application No. WO 93/07256.

According to the present invention, the introduced PPSRP may be maintained in the plant cell stably if it is incorporated into a non-chromosomal autonomous replicon or integrated into the plant chromosomes. Alternatively, the introduced PPSRP may be present on an extra-chromosomal non-replicating vector and be transiently expressed or transiently active.

In one embodiment, a homologous recombinant microorganism can be created wherein the PPSRP is integrated into a chromosome, a vector is prepared which contains at least a portion of a PPSRP gene into which a deletion, addition or substitution has been introduced to thereby alter, e.g., functionally disrupt, the PPSRP gene. Preferably, the PPSRP gene is a *Physcomitrella patens, Brassica napus, Glycine max*, or *Oryza sativa* PPSRP gene, but it can be a homolog from a related plant or even from a mammalian, yeast, or insect source. In a preferred embodiment, the vector is designed such that, upon homologous recombination, the endogenous PPSRP gene is functionally disrupted (i.e., no longer encodes a functional polypeptide; also referred to as a knock-out vector). Alternatively, the vector can be designed such that, upon homologous recombination, the endogenous PPSRP gene is mutated or otherwise altered but still encodes a functional polypeptide (e.g., the upstream regulatory region can be altered to thereby alter the expression of the endogenous PPSRP). To create a point mutation via homologous recombination, DNA-RNA hybrids can be used in a technique known as chimeraplasty (Cole-Strauss et al., 1999 Nucleic Acids Research 27(5):1323-1330 and Kmiec, 1999 Gene therapy American Scientist. 87(3):240-247). Homologous recombination procedures in *Physcomitrella patens* are also well known in the art and are contemplated for use herein.

Whereas in the homologous recombination vector, the altered portion of the PPSRP gene is flanked at its 5' and 3' ends by an additional nucleic acid molecule of the PPSRP gene to allow for homologous recombination to occur between the exogenous PPSRP gene carried by the vector and an endogenous PPSRP gene, in a microorganism or plant. The additional flanking PPSRP nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987 Cell 51:503 for a description of homologous recombination vectors or Strepp et al., 1998 PNAS, 95 (8):4368-4373 for cDNA based recombination in *Physcomitrella patens*). The vector is introduced into a microorganism or plant cell (e.g., via polyethylene glycol mediated DNA), and cells in which the introduced PPSRP gene has homologously recombined with the endogenous PPSRP gene are selected using art-known techniques.

In another embodiment, recombinant microorganisms can be produced that contain selected systems that allow for regulated expression of the introduced gene. For example, inclusion of a PPSRP gene on a vector placing it under control of the lac operon permits expression of the PPSRP gene only in the presence of IPTG. Such regulatory systems are well known in the art.

Whether present in an extra-chromosomal non-replicating vector or a vector that is integrated into a chromosome, the PPSRP polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984 EMBO J. 3:835) or functional equivalents thereof but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987 Nucl. Acids Research 15:8693-8711). Examples of plant expression vectors include those detailed in: Becker, D., Kemper, E., Schell, J. and Masterson, R., 1992 New plant binary vectors with selectable markers located proximal to the left border, Plant Mol. Biol. 20: 1195-1197; and Bevan, M. W., 1984 Binary *Agrobacterium* vectors for plant transformation, Nucl. Acid. Res. 12:8711-8721; Vectors for Gene Transfer in Higher Plants; in: Transgenic Plants, Vol. 1, Engineering and Utilization, eds.: Kung and R. Wu, Academic Press, 1993, S. 15-38.

Plant gene expression should be operatively linked to an appropriate promoter conferring gene expression in a timely, cell or tissue specific manner. Promoters useful in the expression cassettes of the invention include any promoter that is capable of initiating transcription in a plant cell. Such promoters include, but are not limited to those that can be obtained from plants, plant viruses, and bacteria that contain genes that are expressed in plants, such as *Agrobacterium* and *Rhizobium*.

The promoter may be constitutive, inducible, developmental stage-preferred, cell type-preferred, tissue-preferred or organ-preferred. Constitutive promoters are active under most conditions. Examples of constitutive promoters include the CaMV 19S and 35 S promoters (Odell et al. (1985) Nature 313:810-812), the sX CaMV 35S promoter (Kay et al. (1987) Science 236:1299-1302) the Sep1 promoter, the rice actin promoter (McElroy et al. (1990) Plant Cell 2:163-171), the

*Arabidopsis* actin promoter, the ubiquitan promoter (Christensen et al. (1989) Plant Molec Biol 18:675-689); pEmu (Last et al. (1991) Theor Appl Genet 81:581-588), the figwort mosaic virus 35S promoter, the Smas promoter (Velten et al. (1984) EMBO J 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) prompter, and the like.

Inducible promoters are active under certain environmental conditions, such as the presence or absence of a nutrient or metabolite, heat or cold, light, pathogen attack, anaerobic conditions, and the like. For example, the hsp80 promoter from *Brassica* is induced by heat shock, the PPDK promoter is induced by light, the PR-1 promoter from tobacco, *Arabidopsis* and maize are inducible by infection with a pathogen, and the Adh1 promoter is induced by hypoxia and cold stress. Plant gene expression can also be facilitated via an inducible promoter (for review see Gatz, 1997 Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992 Plant J. 2:397-404) and an ethanol inducible promoter (PCT Application No. WO 93/21334). Also, suitable promoters responding to biotic or abiotic stress conditions are those such as the pathogen inducible PRPI-gene promoter (Ward et al., 1993 Plant. Mol. Biol. 22:361-366), the heat inducible hsp80-promoter from tomato (U.S. Pat. No. 5,187,267), cold inducible alpha-amylase promoter from potato (PCT Application No. WO 96/12814) or the wound-inducible pinII-promoter (European Patent No. 375091). For other examples of drought, cold, and salt-inducible promoters, such as the RD29A promoter, see Yamaguchi-Shinozalei et al. (1993 Mol. Gen. Genet. 236:331-340).

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters and the like. Seed preferred promoters are preferentially expressed during seed development and/or germination. For example, seed preferred promoters can be embryo-preferred, endosperm preferred and seed coat-preferred. See Thompson et al. (1989) BioEssays 10:108. Examples of seed preferred promoters include, but are not limited to cellulose synthase (celA), Cim1, gamma-zein, globulin-1, maize 19 kD zein (cZ19B1) and the like.

Other suitable tissue-preferred or organ-preferred promoters include the napin-gene promoter from rapeseed (U.S. Pat. No. 5,608,152), the USP-promoter from *Vicia faba* (Baeumlein et al., 1991 Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980) or the legumin B4 promoter (LeB4; Baeumlein et al., 1992 Plant Journal, 2(2): 233-9) as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soy bean lectin promoter, the maize 15 kD zein promoter, the 22 kD zein promoter, the 27 kD zein promoter, the g-zein promoter, the waxy, shrunken 1, shrunken 2 and bronze promoters, the Zm13 promoter (U.S. Pat. No. 5,086,169), the maize polygalacturonase promoters (PG) (U.S. Pat. Nos. 5,412,085 and 5,545,546) and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). Some examples of such heterologous DNA binding domains include the LexA and GAL4 DNA binding domains, Schwechheimer et al. (1998) Plant Mol Biol 36:195-204. The LexA DNA-binding domain is part of the repressor protein LexA from *Escherichia coli* (*E. coli*) (Brent and Ptashne, Cell 43:729-736 (1985)).

The invention further provides a recombinant expression vector comprising a PPSRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a PPSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific or cell type specific expression of antisense RNA. The antisense expression vector can be in the form of a recombinant plasmid, phagemid, or attenuated virus wherein antisense nucleic acids are produced under the control of a high efficiency regulatory region. The activity of the regulatory region can be determined by the cell type, into which the vector is introduced. For a discussion of the regulation of gene expression using antisense genes, see Weintraub, H. et al., Antisense RNA as a molecular tool for genetic analysis, Reviews—Trends in Genetics, Vol. 1(1) 1986 and Mol et al., 1990 FEBS Letters 268:427-430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a PPSRP can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

A host cell of the invention, such as a prokaryotic or eukaryotic host cell in culture, can be used to produce (i.e., express) a PPSRP. Accordingly, the invention further provides methods for producing PPSRPs using the host cells of the invention. In one embodiment, the method comprises culturing the host cell of invention (into which a recombinant expression vector encoding a PPSRP has been introduced, or into which genome has been introduced a gene encoding a wild-type or altered PPSRP) in a suitable medium until PPSRP is produced. In another embodiment, the method further comprises isolating PPSRPs from the medium or the host cell.

Another aspect of the invention pertains to isolated PPSRPs, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of PPSRP in which the polypeptide is separated from some of the cellular components of the cells in which it is naturally or recombinantly produced. In one embodiment, the language "substantially free of cellular material" includes preparations of a PPSRP having less than about 30% (by dry weight) of non-PPSRP material (also referred to herein as a "contaminating polypeptide"), more preferably less than about 20% of non-PPSRP material, still more preferably less than about 10% of non-PPSRP material, and most preferably less than about 5% non-PPSRP material.

When the PPSRP or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of PPSRP in which the polypeptide is separated from chemical precursors or other chemicals that are involved in the synthesis of the polypeptide. In one embodiment, the language "substantially free of chemical precursors or other chemicals" includes preparations of a PPSRP having less than about 30% (by dry weight) of chemical precursors or non-PPSRP chemicals, more preferably less than about 20% chemical precursors or non-PPSRP chemicals, still more preferably less than about 10% chemical precursors or non-PPSRP chemicals, and most preferably less than about 5% chemical precursors or non-PPSRP chemicals. In preferred embodiments, isolated polypeptides, or biologically active portions thereof, lack contaminating polypeptides from the same organism from which the PPSRP is derived. Typically, such polypeptides are produced by recombinant expression of, for example, a *Physcomitrella patens* PPSRP in plants other than *Physcomitrella patens* or microorganisms such as *C. glutamicum*, ciliates, algae or fungi.

The nucleic acid molecules, polypeptides, polypeptide homologs, fusion polypeptides, primers, vectors, and host cells described herein can be used in one or more of the following methods: identification of *Physcomitrella patens, Brassican napus, Glycine max, Oryza sativa*, and related organisms; mapping of genomes of organisms related to *Physcomitrella patens, Brassican napus, Glycine max*, or *Oryza sativa*; identification and localization of *Physcomitrella patens, Brassican napus, Glycine max*, or *Oryza sativa* sequences of interest; evolutionary studies; determination of PPSRP regions required for function; modulation of a PPSRP activity; modulation of the metabolism of one or more cell functions; modulation of the transmembrane transport of one or more compounds; and modulation of stress resistance.

The moss *Physcomitrella patens* represents one member of the mosses. It is related to other mosses such as *Ceratodon purpureus*, which is capable of growth in the absence of light. Mosses like *Ceratodon* and *Physcomitrella* share a high degree of sequence identity on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The PPSRP nucleic acid molecules of the invention have a variety of uses. Most importantly, the nucleic acid and amino acid sequences of the present invention can be used to transform plants, thereby inducing tolerance to stresses such as drought, high salinity and cold. The present invention therefore provides a transgenic plant transformed by a PPSRP nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass, and forage crops, for example.

In particular, the present invention describes using the expression of PP2A-1 and PP-1 of *Physcomitrella patens*; BnPP2A-1, BnPP2A-2, and BnPP2A-3 of *Brassica napus*; GmPP2A-1, GmPP2A-2, GmPP2A-3, GmPP2A-4, and GmPP2A-5 of *Glycine max*; and OsPP2A-1, OsPP2A-2, OsPP2A-3, OsPP2A-4, and OsPP2A-5 of *Oryza sativa* to engineer drought-tolerant, salt-tolerant and/or cold-tolerant plants. This strategy has herein been demonstrated for *Arabidopsis thaliana*, Rapeseed/Canola, soybeans, corn, and wheat, but its application is not restricted to these plants. Accordingly, the invention provides a transgenic plant containing a PPSRP such as PP2A-1 (SEQ ID NO:3), PP-1 (SEQ ID NO:6), BnPP2A-1 (SEQ ID NO:8), BnPP2A-2 (SEQ ID NO:10), BnPP2A-3 (SEQ ID NO:12), GmPP2A-1 (SEQ ID NO:14), GmPP2A-2 (SEQ ID NO:16), GmPP2A-3 (SEQ ID NO:18), GmPP2A-4 (SEQ ID NO:20), GmPP2A-5 (SEQ ID NO:22), OsPP2A-1 (SEQ ID NO:24), OsPP2A-2 (SEQ ID NO:26), OsPP2A-3 (SEQ ID NO:28), OsPP2A-4 (SEQ ID NO:30), and OsPP2A-5 (SEQ ID NO:32), wherein the plant has an increased tolerance to an environmental stress selected from drought, increased or decreased salinity, and decreased or increased temperature. In preferred embodiments, the environmental stress is drought or increased salinity.

Accordingly, the invention provides a method of producing a transgenic plant with a PPSRP coding nucleic acid, wherein expression of the nucleic acid(s) in the plant results in increased growth/yield under normal or stress conditions and/or increased tolerance to environmental stress as compared to a wild type variety of the plant comprising: (a) introducing into a plant cell an expression vector comprising a PPSRP nucleic acid, and (b) generating from the plant cell a transgenic plant with an increased growth/yield under normal or stress conditions and/or increased tolerance to environmental stress as compared to a wild type variety of the plant. The plant cell includes, but is not limited to, a protoplast, gamete producing cell, and a cell that regenerates into a whole plant. As used herein, the term "transgenic" refers to any plant, plant cell, callus, plant tissue or plant part, that contains all or part of at least one recombinant polynucleotide. In many cases, all or part of the recombinant polynucleotide is stably integrated into a chromosome or stable extra-chromosomal element, so that it is passed on to successive generations. The parameters that can be used to measure a plant's growth/yield include, but are not limited to, (a) total seed weight per plant, (b) number of filled seeds per plant, (c) number of flowers per plant, (d) number of flower clusters, (e) filling rate for the seed, (f) thousand kernel weight, (g) seed size, (h) time to flower, (i) maximal above-ground plant biomass, (j) above-ground plant biomass at young stage, (k) harvest index (ratio of total seed weight per plant over maximal above-ground plant biomass), (l) maximal root biomass, (m) root-shoot index (ratio of root biomass over above-ground plant biomass), (n) any parameter derived from any of the foregoing parameters, or any parameter derived from any of the foregoing parameters.

The present invention also provides a method of modulating a plant's tolerance to an environmental stress comprising, modifying the expression of a PPSRP coding nucleic acid in the plant. The plant's tolerance to the environmental stress can be increased or decreased as achieved by increasing or decreasing the expression of a PPSRP, respectively. Preferably, the plant's tolerance to the environmental stress is increased by increasing expression of a PPSRP. Expression of a PPSRP can be modified by any method known to those of skill in the art. The methods of increasing expression of PPSRPs can be used wherein the plant is either transgenic or not transgenic. In cases when the plant is transgenic, the plant can be transformed with a vector containing any of the above described PPSRP coding nucleic acids, or the plant can be transformed with a promoter that directs expression of native PPSRP in the plant, for example. The invention provides that such a promoter can be tissue specific. Furthermore, such a promoter can be developmentally regulated. Alternatively, non-transgenic plants can have native PPSRP expression modified by inducing a native promoter. The expression of PP2A-1 (SEQ ID NO:2), PP-1 (SEQ ID NO:5), BnPP2A-1 (SEQ ID NO:7), BnPP2A-2 (SEQ ID NO:9), BnPP2A-5 (SEQ ID NO:11), GmPP2A-1 (SEQ ID NO:13), GmPP2A-2 (SEQ ID NO:15), GmPP2A-3 (SEQ ID NO:17), GmPP2A-4 (SEQ ID NO:19), GmPP2A-5 (SEQ ID NO:21), OsPP2A-1 (SEQ ID NO:23), OsPP2A-2 (SEQ ID NO:25), OsPP2A-3 (SEQ ID NO:27), OsPP2A-4 (SEQ ID NO:29), or OsPP2A-5 (SEQ ID NO:31) in target plants can be accomplished by, but is not limited to, one of the following examples: (a) constitutive promoter, (b) stress-inducible promoter, (c) chemical-induced promoter, and (d) engineered promoter over-expression with for example zinc-finger derived transcription factors (Greisman and Pabo, 1997 Science 275:657).

In a preferred embodiment, transcription of the PPSRP is modulated using zinc-finger derived transcription factors (ZFPs) as described in Greisman and Pabo, 1997 Science 275:657 and manufactured by Sangamo Biosciences, Inc. These ZFPs comprise both a DNA recognition domain and a functional domain that causes activation or repression of a target nucleic acid such as a PPSRP nucleic acid. Therefore, activating and repressing ZFPs can be created that specifically recognize the PPSRP promoters described above and used to increase or decrease PPSRP expression in a plant, thereby modulating the stress tolerance of the plant. The present invention also includes identification of the PP2A-1 (SEQ ID NO:2), PP-1 (SEQ ID NO:5), BnPP2A-1 (SEQ ID NO:7), BnPP2A-2 (SEQ ID NO:9), BnPP2A-5 (SEQ ID NO:11), GmPP2A-1 (SEQ ID NO:13), GmPP2A-2 (SEQ ID NO:15), GmPP2A-3 (SEQ ID NO:17), GmPP2A-4 (SEQ ID NO:19), GmPP2A-5 (SEQ ID NO:21), OsPP2A-1 (SEQ ID NO:23), OsPP2A-2 (SEQ ID. NO:25), OsPP2A-3 (SEQ ID NO:27), OsPP2A-4 (SEQ ID NO:29), and OsPP2A-5 (SEQ ID NO:31) homologs in a target plant as well as the homolog's promoter. The invention also provides a method of increasing expression of a gene of interest within a host cell as compared to a wild type variety of the host cell, wherein the gene of interest is transcribed in response to a PPSRP, comprising: (a) transforming the host cell with an expression vector comprising a PPSRP coding nucleic acid, and (b) expressing the PPSRP within the host cell, thereby increasing the expression of the gene transcribed in response to the PPSRP, as compared to a wild type variety of the host cell.

In addition to introducing the PPSRP nucleic acid sequences into transgenic plants, these sequences can also be used to identify an organism as being *Physcomitrella patens, Brassican napus, Glycine max, Oryza sativa* or a close relative thereof. Also, they may be used to identify the presence of *Physcomitrella patens, Brassican napus, Glycine max, Oryza sativa* or a relative thereof in a mixed population of microorganisms. The invention provides the nucleic acid sequences of a number of *Physcomitrella patens, Brassican napus, Glycine max*, and *Oryza sativa* genes; by probing the extracted genomic DNA of a culture of a unique or mixed population of microorganisms under stringent conditions with a probe spanning a region of a gene, which is unique to this organism, one can ascertain whether this organism is present.

Further, the nucleic acid and polypeptide molecules of the invention may serve as markers for specific regions of the genome. This has utility not only in the mapping of the genome, but also in functional studies of *Physcomitrella patens, Brassican napus, Glycine max*, or *Oryza sativa* polypeptides. For example, to identify the region of the genome to which a particular *Physcomitrella patens* DNA-binding polypeptide binds, the *Physcomitrella patens* genome could be digested, and the fragments incubated with the DNA-binding polypeptide. Those fragments that bind the polypeptide may be additionally probed with the nucleic acid molecules of the invention, preferably with readily detectable labels. Binding of such a nucleic acid molecule to the genome fragment enables the localization of the fragment to the genome map of *Physcomitrella patens*, and, when performed multiple times with different enzymes, facilitates a rapid determination of the nucleic acid sequence to which the polypeptide binds. Further, the nucleic acid molecules of the invention may be sufficiently identical to the sequences of related species such that these nucleic acid molecules may serve as markers for the construction of a genomic map in related mosses.

The PPSRP nucleic acid molecules of the invention are also useful for evolutionary and polypeptide structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the polypeptide that are essential for the functioning of the enzyme. This type of determination is of value for polypeptide engineering studies and may give an indication of what the polypeptide can tolerate in terms of mutagenesis without losing function.

Manipulation of the PPSRP nucleic acid molecules of the invention may result in the production of PPSRPs having functional differences from the wild-type PPSRPs. These polypeptides may be improved in efficiency or activity, may be present in greater numbers in the cell than is usual, or may be decreased in efficiency or activity.

There are a number of mechanisms by which the alteration of a PPSRP of the invention may directly affect stress response and/or stress tolerance. In the case of plants expressing PPSRPs, increased transport can lead to improved salt and/or solute partitioning within the plant tissue and organs. By either increasing the number or the activity of transporter molecules that export ionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, polypeptide synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469-714, VCH: Weinheim; Belter, P. A. et al., 1988 Bioseparations: downstream processing for biotechnology, John Wiley and Sons; Kennedy, J. F. and Cabral, J. M. S., 1992 Recovery processes for biological materials, John Wiley and Sons; Shaeiwitz, J. A. and Henry, J. D., 1988 Biochemical separations, in: Ulmann's Encyclopedia of Industrial Chemistry, vol. B3, Chapter 11, page 1-27, VCH: Weinheim; and Dechow, F. J. (1989) Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stress. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived there from can then be assayed for fail or alteration of their tolerance to drought, salt, and temperature stress.

The engineering of one or more PPSRP genes of the invention may also result in PPSRPs having altered activities which indirectly impact the stress response and/or stress tolerance of algae, plants, ciliates or fungi or other microorganisms like *C. glutamicum*. For example, the normal biochemical processes of metabolism result in the production of a variety of products (e.g., hydrogen peroxide and other reactive oxygen species) which may actively interfere with these same metabolic processes (for example, peroxynitrite is known to nitrate tyrosine side chains, thereby inactivating some enzymes having tyrosine in the active site (Groves, J. T., 1999 Curr. Opin. Chem. Biol. 3(2):226-235). While these products are typically excreted, cells can be genetically altered to transport more products than is typical for a wild-type cell. By optimizing the activity of one or more PPSRPs of the invention that are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells (Girke, T., 1998 The Plant Journal 15:39-48). The resultant knockout cells can then be evaluated for their ability or capacity to tolerate various stress conditions, their response to various stress conditions, and the effect on the phenotype and/or genotype of the mutation. For other methods of gene inactivation see U.S. Pat. No. 6,004,804 "Non-Chimeric Mutational Vectors" and Puttaraju et al., 1999 Spliceosome-mediated RNA trans-splicing as a tool for gene therapy Nature Biotechnology 17:246-252.

The aforementioned mutagenesis strategies for PPSRPs resulting in increased stress resistance are not meant to be limiting; variations on these strategies will be readily apparent to one skilled in the art. Using such strategies, and incorporating the mechanisms disclosed herein, the nucleic acid and polypeptide molecules of the invention may be utilized to generate algae, ciliates, plants, fungi or other microorganisms like *C. glutamicum* expressing mutated PPSRP nucleic acid and polypeptide molecules such that the stress tolerance is improved.

The present invention also provides antibodies that specifically bind to a PPSRP, or a portion thereof, as encoded by a nucleic acid described herein. Antibodies can be made by many well-known methods (See, e.g. Harlow and Lane, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992 Bio/Technology 10:163-167; Bebbington et al., 1992 Bio/Technology 10:169-175).

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See *Harlow and Lane* "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif, Fourth Edition) and references cited therein, and in Harlow and Lane ("Antibodies, A Laboratory Manual" Cold Spring Harbor Publications, New York, 1988).

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of *Physcomitrella patens* Cultures

For this study, plants of the species *Physcomitrella patens* (Hedw.) B.S.G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55, 438-446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromols$^{-1}$m$^{-2}$ (white light; Philips TL 65W/25 fluorescent tube) and a light/dark change of 16/8 hours. The moss was either modified in liquid culture using Knop medium according to Reski and Abel (1985, Planta 165:354-358) or cultured on Knop solid medium-using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 μl of N-laurylsarcosine buffer, 20 μl of β-mercaptoethanol and 10 μl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 μl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 μl of $H_2O$+RNAse (50 mg/ml final concentration). The DNA was dissolved overnight at 4° C. and the RNAse digestion was subsequently carried out at 37° C. for 1 hour. Storage of the DNA took place at 4° C.

Example 3

Isolation of Total RNA and Poly-(A)+ RNA and cDNA Library Construction from *Physcomitrella patens*

For the investigation of transcripts, both total RNA and poly-(A)$^+$ RNA were isolated. The total RNA was obtained from wild-type 9 day old protonemata following the GTC-method (Reski et al. 1994, Mol. Gen. Genet., 244:352-359). The Poly(A)+ RNA was isolated using Dyna Beads$^R$ (Dynal, Oslo, Norway) following the instructions of the manufacturer's protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase 1, Klenow enzyme and RNAseH digestion at 12° C. (2 hours), 16° C. (1 hour), and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (see Sambrook et al. 1989. Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

```
5'-CAGGAAACAGCTATGACC-3'        SEQ ID NO:33

5'-CTAAAGGGAACAAAAGCTG-3'       SEQ ID NO:34

5'-TGTAAAACGACGGCCAGT-3'        SEQ ID NO:35
```

Sequences were processed and annotated using the software package EST-MAX commercially provided by BioMax (Munich, Germany). The program incorporates practically all bioinformatics methods important for functional and structural characterization of protein sequences. The most important algorithms incorporated in EST-MAX are: FASTA (Very sensitive sequence database searches with estimates of statistical significance; Pearson W. R. (1990) Rapid and sensitive sequence comparison with FASTP and FASTA. Methods Enzymol. 183:63-98); BLAST (Very sensitive sequence database searches with estimates of statistical significance. Altschul S. F., Gish W., Miller W., Myers E. W., and Lipman D. J. Basic local alignment search tool. Journal of Molecular Biology 215:403-10); PREDATOR (High-accuracy secondary structure prediction from single and multiple sequences. Frishman, D. and Argos, P. (1997) 75% accuracy in protein secondary structure prediction. Proteins, 27:329-335); CLUSTAL W: Multiple sequence alignment. Thompson, J. D., Higgins, D. G. and Gibson, T. J. (1994) CLUSTAL W (improving the sensitivity of progressive multiple sequence alignment through sequence weighting, positions-specific gap penalties and weight matrix choice. Nucleic Acids Research, 22:4673-4680); TMAP (Transmembrane region prediction from multiply aligned sequences. Persson, B. and Argos, P. (1994) Prediction of transmembrane segments in proteins utilizing multiple sequence alignments. J. Mol. Biol. 237:182-192); ALOM2 (Transmembrane region prediction from single sequences. Klein, P., Kanehisa, M., and DeLisi, C. Prediction of protein function from sequence properties: A discriminate analysis of a database. Biochim. Biophys. Acta 787:221-226 (1984). Version 2 by Dr. K. Nakai); PROSEARCH (Detection of PROSITE protein sequence patterns. Kolakowski L. F. Jr., Leunissen J. A. M., Smith J. E. (1992) ProSearch: fast searching of protein sequences with regular expression patterns related to protein structure and function. Biotechniques 13, 919-921); BLIMPS (Similarity searches against a database of ungapped blocks. J. C. Wallace and Henikoff S., (1992)); PATMAT (A searching and extraction program for sequence, pattern and block queries and databases, CABIOS 8:249-254. Written by Bill Alford.).

Example 5

Identification of *Physcomitrella patens* ORFs Corresponding to PpPP2A-1 and PpPP-1

The *Physcomitrella patens* partial cDNAs (ESTs) for PpPP2A-1 (SEQ ID NO:1) and PpPP-1 (SEQ ID NO:4) were identified in the *Physcomitrella patens* EST sequencing program using the program EST-MAX through BLAST analysis. These particular clones, which were found to encode for protein phosphatases, were chosen for further analyses (see Tables 1-3 below).

TABLE 1

Identification of Open Reading Frames

| Name | Vector | Total Nucleotides in Clone | ORF position | Total Amino Acids in ORF |
|---|---|---|---|---|
| PP2A-1 | PCR2.1 | 1279 | 123–1057 | 311 |
| PP-1 | PCR2.1 | 1014 | 39–950 | 303 |

TABLE 2

Degree of amino acid identity and similarity of PpPP2A-1 and other homologous proteins (Pairwise Comparison was used: gap penalty: 10; gap extension penalty: 0.1; score matrix: blosum 62)

| | Swiss-Prot # | | | | |
|---|---|---|---|---|---|
| | Q9XGH7 | Q07100 | Q9SBW3 | P48578 | Q9XF94 |
| Protein name | Serine/ Threonine Protein Phosphatase PP2A Catalytic Subunit | Serine/ Threonine Protein Phosphatase PP2A-3 Catalytic Subunit | Serine/ Threonine Protein Phosphatase PP2A-4 Catalytic Subunit | Serine/ Threonine Protein Phosphatase PP2A-4 Catalytic Subunit | Serine/ Threonine Protein Phosphatase PP2A-2 Catalytic Subunit |
| species | Nicotiana tabacum (Common tobacco) | Arabidopsis thaliana (Mouse-ear cress) | Oryza sativa (Rice) | Arabidopsis thaliana (Mouse-ear cress) | Oryza sativa (Rice) |
| Identity % | 89% | 88% | 88% | 88% | 88% |
| Similarity % | 92% | 91% | 89% | 91% | 90% |

TABLE 3

| Degree of amino acid identity and similarity of PpPP-1 and other homologous proteins (Pairwise Comparison was used: gap penalty: 10; gap extension penalty: 0.1; score matrix: blosum 62) | | | | | |
|---|---|---|---|---|---|
| | Swiss-Prot # | | | | |
| | Q42912 | Q9LHE7 | Q9SX52 | Q9U9A3 | O00743 |
| Protein name | Serine/threonine protein phosphatase | Phospho-protein Phosphatase | F1413.5 protein | Protein Phosphatase 6 Catalytic Subunit | Serine/Threonine Protein Phosphatase 6 |
| species | Malus domestica (Apple) (Malus sylvestris) | Arabidopsis thaliana (Mouse-ear cress) | Arabidopsis thaliana (Mouse-ear cress) | Dictyostelium discoideum (Slime mold). | Homo sapiens (Human) |
| Identity % | 91% | 90% | 90% | 72% | 68% |
| Similarity % | 95% | 95% | 95% | 81% | 80% |

Example 6

Cloning of Full-Length *Physcomitrella patens* cDNA Encoding for PpPP2A-1 and PpPP-1

To isolate full-length PpPP2A-1 (SEQ ID NO:2) and PpPP-1 (SEQ ID NO:5) from *Physcomitrella patens*, PCR was performed (as described below in Full-Length Amplification) using the original ESTs described in Example 5 as template since they were full-length. The primers used for amplification are listed below in Table 4.

Full-Length Amplification

Full-length clones corresponding PpPP2A-1 (SEQ ID NO: 2) and PpPP-1 (SEQ ID NO: 5) were obtained by performing polymerase chain reaction (PCR) with gene-specific primers (see Table 4) and the original EST as the template. The conditions for the reaction were standard conditions with PWO DNA polymerase (Roche). PCR was performed according to standard conditions and to manufacturer's protocols (Sambrook et al., 1989 Molecular Cloning, A Laboratory Manual. 2nd Edition. Cold Spring Harbor Laboratory Press. Cold Spring Harbor, N.Y., Biometra T3 Thermocycler). The parameters for the reaction were: five minutes at 94° C. followed by five cycles of one minute at 94° C., one minute at 50° C., and 1.5 minutes at 72° C. This was followed by twenty-five cycles of one minute at 94° C., one minute at 65° C., and 1.5 minutes at 72° C.

The amplified fragments were extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al. 1989. Molecular Cloning, A Laboratory Manual. 2nd Edition. Cold Spring Harbor Laboratory Press. Cold Spring Harbor, N.Y.). Transformed cells were selected for on LB agar containing 100 μg/ml carbenicillin, 0.8 mg X-gal (5-bromo-4-chloro-3-indolyl-β-D-galactoside), and 0.8 mg IPTG (isopropylthio-β-D-galactoside) grown overnight at 37° C. White colonies were selected and used to inoculate 3 ml of liquid LB containing 100 μg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al., 1989 Molecular Cloning, A Laboratory Manual. 2nd Edition. Cold Spring Harbor Laboratory Press. Cold Spring Harbor, N.Y.).

TABLE 4

Scheme and primers used for cloning of full-length clones

| Gene Name | Cloning site | Cloning method | 5' RACE primer | Full Length primers |
|---|---|---|---|---|
| PpPP2A-1 | XmaI/SacI | PCR of original EST clone | | RC001:<br>5' ATCCCGGGACGACATGAGTGTGCCTCCGATATC 3'<br>(SEQ ID NO:36)<br>RC002:<br>5' CTGAGCTCAAGTCCCACTATAAGAAGTAGTCT 3'<br>(SEQ ID NO:37) |
| PpPP-1 | XmaI/HpaI | PCR of original EST clone | | RC381:<br>5' ATCCCGGGAGGAAGGGGACTGGACACAACGTGATG 3'<br>(SEQ ID NO:38)<br>RC382:<br>5' GCGTTAACGCACCATATGATGCTTTCCGGTCGTC 3'<br>(SEQ ID NO:39) |

Example 7

Engineering Stress-Tolerant *Arabidopsis plants* by Expressing PPSRP Genes

Binary Vector Construction: pBPSJH001

The pLMNC53 (Mankin, 2000, PhD thesis, University of North Carolina) vector was digested with HindIII (Roche) and blunt-end filled with Klenow enzyme and 0.1 mM dNTPs (Roche) according to manufacturer's instructions. This fragment was extracted from an agarose gel with a QIAquick Gel Extraction Kit (Qiagen) according to manufacturer's instructions. The purified fragment was then digested with EcoRI (Roche) and extracted from agarose gel with a QIAquick Gel Extraction Kit (Qiagen) according to manufacturer's instructions. The resulting 1.4 kilobase fragment, the gentamycin cassette, included the nos promoter, aacCI gene, and g7 terminator.

The vector pBlueScript was digested with EcoRI and SmaI (Roche) according to manufacturer's instructions. The resulting fragment was extracted from agarose gel with a QIAquick Gel Extraction Kit (Qiagen) according to manufacturer's instructions. The digested pBlueScript vector and the gentamycin cassette fragments were ligated with T4 DNA Ligase (Roche) according to manufacturer's instructions, joining the two respective EcoRI sites and joining the blunt-ended HindIII site with the SmaI site.

The recombinant vector (pGMBS) was transformed into Top10 cells (Invitrogen) using standard conditions. Transformed cells were selected for on LB agar containing 100 μg/ml carbenicillin, 0.8 mg X-gal (5-bromo-4-chloro-3-indolyl-β-D-galactoside), and 0.8 mg IPTG (isopropylthio-β-D-galactoside), grown overnight at 37° C. White colonies were selected and used to inoculate 3 ml of liquid LB containing 100 μg/ml ampicillin and grown overnight at 37° C. Plasmid DNA was extracted using the QIAprep Spin Miniprep Kit (Qiagen) following manufacturer's instructions. Analyses of subsequent clones and restriction mapping were performed according to standard molecular biology techniques (Sambrook et al. 1989, Molecular Cloning, A Laboratory Manual, 2nd Edition, Cold Spring Harbor Laboratory Press. Cold Spring Harbor, N.Y.).

Both the pGMBS vector and plbxSuperGUS vector were digested with XbaI and KpnI (Roche) according to manufacturer's instructions, excising the gentamycin cassette from pGMBS and producing the backbone from the plbxSuperGUS vector. The resulting fragments were extracted from agarose gel with a QIAquick Gel Extraction Kit (Qiagen) according to manufacturer's instructions. These two fragments were ligated with T4 DNA ligase (Roche) according to manufacturer's instructions.

The resulting recombinant vector (pBPSJH001) was transformed into Top10 cells (Invitrogen) using standard conditions. Transformed cells were selected for on LB agar containing 100 μg/ml carbenicillin, 0.8 mg X-gal (5-bromo-4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 μg/ml ampicillin and grown overnight at 37° C. Plasmid DNA was extracted using the QIAprep Spin Miniprep Kit (Qiagen) following manufacturer's instructions. Analyses of subsequent clones and restriction mapping were performed according to standard molecular biology techniques (Sambrook et al. 1989, Molecular Cloning, A Laboratory Manual, 2nd Edition, Cold Spring Harbor Laboratory Press, Cold Spring Harbor, N.Y.).

Subcloning of PpPP2A-1 and PpPP-1 Into the Binary Vector

The fragments containing the different *Physcomitrella patens* protein phosphatases were excised from the recombinant PCR2.1 TOPO vectors by double digestion with restriction enzymes (see Table 5) according to manufacturer's instructions. The subsequent fragment was excised from agarose gel with a QIAquick Gel Extraction Kit (Qiagen) according to manufacturer's instructions and ligated into the binary vector pBPSJH001, cleaved with appropriate enzymes (see Table 5) and dephosphorylated prior to ligation. The resulting recombinant vector contained the corresponding phosphatase in the sense orientation under the control of the constitutive super promoter.

TABLE 5

Listed are the names of the two constructs of the *Physcomitrella patens* phosphatases used for plant transformation

| Gene | Enzymes used to generate gene fragment | Enzymes used to restrict pBPSJH001 | Binary Vector Construct |
|---|---|---|---|
| PpPP2A-1 | XmaI/SacI | XmaI/SacI | pBPSSH004 |
| PpPP-1 | XmaI/HpaI | XmaI/Ecl136 | pBPSLVM018 |

*Agrobacterium* Transformation

The recombinant vectors were transformed into *Agrobacterium tumefaciens* C58C1 and PMP90 according to standard conditions (Hoefgen and Willmitzer, 1990).

Plant Transformation

*Arabidopsis thaliana* ecotype C24 were grown and transformed according to standard conditions (Bechtold 1993, Acad. Sci. Paris. 316:1194-1199; Bent et al. 1994, Science 265:1856-1860).

Screening of Transformed Plants

T1 seeds were sterilized according to standard protocols (Xiong et al. 1999, Plant Molecular Biology Reporter 17: 159-170). Seeds were plated on ½ Murashige and Skoog media (MS) (Sigma-Aldrich), 0.6% agar and supplemented with 1% sucrose, 150 μg/ml gentamycin (Sigma-Aldrich), and 2 μg/ml benomyl (Sigma-Aldrich). Seeds on plates were vernalized for four days at 4° C. The seeds were germinated in a climatic chamber at an air temperature of 22° C. and light intensity of 40 micromols$^{-1m2}$ (white light; Philips TL 65W/25 fluorescent tube) and 16 hours light and 8 hours dark day length cycle. Transformed seedlings were selected after 14 days and transferred to ½ MS media supplemented with 0.6% agar, 1% sucrose, and allowed to recover for five-seven days.

Drought Tolerance Screening

T1 seedlings were transferred to dry, sterile filter paper in a petri dish and allowed to desiccate for two hours at 80% RH (relative humidity) in a Sanyo Growth Cabinet MLR-350H, micromols$^{-1m2}$ (white light; Philips TL 65W/25 fluorescent tube). The RH was then decreased to 60%, and the seedlings were desiccated further for eight hours. Seedlings were then removed and placed on ½ MS 0.6% agar plates supplemented with 2 μg/ml benomyl (Sigma-Aldrich) and scored after five days. The transgenic plants were screened for their improved drought tolerance.

Under drought stress conditions, PpPP2A-1 over-expressing *Arabidopsis thaliana* plants showed a 62% (8 survivors from 13 stressed plants) survival rate to the stress screening, whereas the untransformed control showed less than a 6% survival rate. The transgenic lines survived the treatment while the wild-type plants were nearly dead or did not survive. It is noteworthy that the analyses of these transgenic lines were performed with T1 plants, and therefore, the results will be better when a homozygous, strong expresser is found.

Freezing Tolerance Screening

Seedlings were moved to petri dishes containing ½ MS 0.6% agar supplemented with 2% sucrose and 2 μg/ml benomyl. After four days, the seedlings were incubated at 4° C. for 1 hour and then covered with shaved ice. The seedlings were then placed in an Environmental Specialist ES2000 Environmental Chamber and incubated for 3.5 hours beginning at −1.0° C., and decreasing −1° C. each hour. The seedlings were then incubated at −5.0° C. for 24 hours and then allowed to thaw at 5° C. for 12 hours. The water was poured off and the seedlings were scored after 5 days.

The transgenic plants are screened for their improved cold tolerance, demonstrating that transgene expression (or repression in the case of PP-1) confers cold tolerance. It is noteworthy that the analyses of these transgenic lines were performed with T1 plants, and therefore, the results will be better when a homozygous, strong expresser is found.

Salt Tolerance Screening

Seedlings were transferred to filter paper soaked in ½ MS and placed on ½ MS 0.6% agar supplemented with 2 μg/ml benomyl the night before the salt tolerance screening. For the salt tolerance screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 M NaCl, in a petri dish. After 10 hours, the seedlings were moved to petri dishes containing ½ MS 0.6% agar supplemented with 2 μg/ml benomyl. The seedlings were scored after 5 days. The transgenic plants are then screened for their improved salt tolerance demonstrating that transgene expression (or repression in the case of PP-1) confers salt tolerance.

Example 8

Detection of the PP2A-1 Transgene in the Transgenic *Arabidopsis Lines*

PCR Based Assay

To check for the presence of the PP2A-1 transgene in transgenic *Arabidopsis* lines, PCR was performed on genomic DNA which contaminates the RNA samples taken as described in Example 9 below. Two and one half microliters of the RNA sample was used in a 50 μl PCR reaction using Tag DNA polymerase (Roche Molecular Biochemicals) according to the manufacturer's instructions.

Binary vector plasmid with each gene cloned in was used as positive control, and the wild-type C24 genomic DNA was used as negative control in the PCR reactions. 10 μl PCR reaction was analyzed on 0.8% agarose-ethidium bromide gel.

PP2A-1: The primers used in the reactions are:

```
5' CCGTTATCCGAGGTCGAGGTCAGAG 3'   (SEQ ID NO:40)

5' CCAGGTCCCGAATGTGGTCCAAGGA 3'   (SEQ ID NO:41)
```

The PCR program was as following: 35 cycles of 1 minute at 94° C., 30 seconds at 62° C. and 1 minute at 72° C., followed by 5 minutes at 72° C. A 0.45 kilobase fragment was produced from the positive control and the transgenic plants.

The transgenes were successfully amplified from the T1 transgenic lines, but not from the wild type C24. This result indicates that the T1 transgenic plants contain at least one copy of the transgenes. There was no indication of existence of either identical or very similar genes in the untransformed *Arabidopsis thaliana* control that could be amplified by this method from the wild-type plants.

Taqman Copy Number Assay

Genomic DNA for TaqMan copy number assays is isolated from leaf samples in 96-well deep-well plates containing a chrome-steel ball, the plates are placed into a minus 80° C. freezer for more than 30 minutes and/or lyophilized overnight. Frozen tissues contained in deep-well plates are ground. Genomic DNA is extracted using the Magnesil® Genomic DNA Extraction kit (Promega, Madison, Wis.) according to manufacturer's instruction.

PCR primers and probes are designed using Primer Express® software (Applied Biosystems, Foster City, Calif.). Primers and probes are designed for both an endogenous control gene as well as a region specific to the transgene present in the construct. Probes are labeled at their 5' end with one reporter fluorophore for the endogenous control and another reporter fluorophore for the transgenes, and both are labeled at the 3' end with a quencher.

Polymerase chain reactions are carried out as described by Ingham et. al. (BioTechniques 31:132-140, 2001) and Ingham (Methods in Molecular Biology 286: 273-289, 2004).

Example 9

Detection of the PP2A-1 Transgene mRNA in Transgenic *Arabidopsis* Lines

RT-PCR Based Assay

Transgene expression was detected using RT-PCR. Total RNA was isolated from stress-treated plants using a procedure adapted from Verwoerd et al. (1989 NAR 17:2362). Leaf samples (50-100 mg) were collected and ground to a fine powder in liquid nitrogen. Ground tissue was resuspended in 500 μl of a 80° C., 1:1 mixture, of phenol to extraction buffer (100 mM LiCl, 100 mM Tris pH8, 10 mM EDTA, 1% SDS), followed by brief vortexing to mix. After the addition of 250 μl of chloroform, each sample was vortexed briefly. Samples were then centrifuged for 5 minutes at 12,000×g. The upper aqueous phase was removed to a fresh eppendorf tube. RNA was precipitated by adding 1/10 volume 3 M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air-dried. RNA sample pellets were resuspended in 10 μl DEPC treated water. To remove contaminating DNA from the samples, each was treated with RNase-free DNase (Roche) according to the manufacturer's recommendations. cDNA was synthesized from total RNA using the Superscript First-Strand Synthesis System for RT-PCR (Gibco-BRL) following manufacturer's recommendations.

PCR amplification of a gene-specific fragment from the synthesized cDNA was performed using Taq DNA polymerase (Roche) and gene-specific primers (see Example 8 for primers) in the following reaction: 1×PCR buffer, 1.5 mM $MgCl_2$, 0.2 μM each primer, 0.2 μM dNTPs, 1 unit polymerase, 5 μl cDNA from synthesis reaction. Amplification was performed under the following conditions: Denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad).

Expression of the transgenes was detected in the T1 transgenic line. This result indicated that the transgenes are expressed in the transgenic lines and demonstrated that their gene product improved plant stress tolerance in the transgenic line. In agreement with the previous statement, no expression of identical or very similar endogenous genes could be detected by this method. These results are in agreement with the data from Example 8.

qRT-PCR Assay

Total RNA for qRT-PCR assays is isolated from leaf samples in wells of a 1.2 ml 96-well deep-well plates (Corning) containing a chrome-steel ball, the plates are placed into a minus 80° C. freezer for more than 30 minutes and/or lyophilized overnight. The frozen tissue within the deep-well plates is ground. Total RNA is extracted using the Magnesil® Genomic DNA Extraction kit (Promega, Madison, Wis.) according to manufacturer's instruction. The RNA is then DNase treated using the DNA-free kit (Ambion, Austin, Tex.) according to manufacturer's instructions.

PCR primers and probes are designed using Primer Express® software (Applied Biosystems, Foster City, Calif.). Primers and probes are designed for both an endogenous control gene as well as a region specific to the transgene present in the construct. Probes are labeled at their 5' end with one reporter fluorophore for the endogenous control and another reporter fluorophore for the transgenes, and both are labeled at the 3' end with a quencher.

Polymerase chain reactions are carried out in 96-well reaction plates (Applied Biosystems, Foster City, Calif.). The one-step SYBR Green I qRT-PCR mastermix (Eurogentec, San Diego, Calif.) is used according to manufacturer's instructions. Fold difference of expression is calculated utilizing the exported cycle threshold (Ct) values as described by Ingham et. al. (BioTechniques 31:132-140, 2001) and Ingham (Methods in Molecular Biology 286: 273-289, 2004).

Example 10

Engineering Stress-tolerant Soybean Plants by Expressing PPSRP Genes

The constructs pBPSSH004 and pBPSLVM018 are used to transform soybean as described below.

Seeds of soybean are surface sterilized with 70% ethanol for 4 minutes at room temperature with continuous shaking, followed by 20% (v/v) CLOROX supplemented with 0.05% (v/v) TWEEN for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate antibiotics followed by growth of the single colony in liquid LB medium to an optical density at 600 nm of 0.8. Then, the bacteria culture is pelleted at 7000 rpm for 7 minutes at room temperature, and resuspended in MS (Murashige and Skoog, 1962) medium supplemented with 100 μM acetosyringone. Bacteria cultures are incubated in this pre-induction medium for 2 hours at room temperature before use. The axis of soybean zygotic seed embryos at approximately 15% moisture content are imbibed for 2 hours at room temperature with the pre-induced *Agrobacterium* suspension culture. The embryos are removed from the imbibition culture and transferred to Petri dishes containing solid MS medium supplemented with 2% sucrose and incubated for 2 days, in the dark at room temperature.

Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the agrobacteria. The liquid medium is used to moisten the sterile filter paper. The embryos are incubated during 4 weeks at 25° C., under 150 $\mu mol\ m^{-2}sec^{-1}$ and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 150 $\mu mol\ m^{-2}sec^{-1}$ light intensity and 12 hours photoperiod for about 80 days.

The transgenic plants are then screened for their improved drought, salt and/or cold tolerance according to the screening method described in Example 7 demonstrating that transgene expression confers stress tolerance.

Example 11

Engineering Stress-tolerant Rapeseed/Canola Plants by Expressing PPSRP Genes Canola cotyledonary petioles of 4 day-old young seedlings are used as explants for tissue culture and transformed according to patent EP1566443. The commercial cultivar Westar (Agriculture Canada) is the standard variety used for transformation, but other varieties can be used.

*Agrobacterium tumefaciens* GV3101:pMP90RK containing a binary vector is used for canola transformation. The standard binary vector used for transformation is pSUN (patent WO02/00900), but many different binary vector systems have been described for plant transformation (e.g. An, G. in *Agrobacterium* Protocols, Methods in Molecular Biology, vol 44, pp 47-62, Gartland K M A and M R Davey eds. Humana Press, Totowa, N.J.). A plant gene expression cassette consists of at least two genes—a selection marker gene and a plant promoter regulating the transcription of the cDNA or genomic DNA of the trait gene. Various selection marker genes can be used including the *Arabidopsis* gene encoding a mutated acetohydroxy acid synthase (AHAS) enzyme (U.S. Pat. Nos. 57,673,666 and 6,225,105). Similarly, various promoters can be used to regulate the trait gene to provide constitutive, developmental, tissue, or environmental regulation of gene transcription. In this example, the 34S promoter (GenBank Accession numbers M59930 and X16673) is used to provide constitutive expression of the trait gene.

Canola seeds are surface-sterilized in 70% ethanol for 2 min, incubated for 15 min in 55° C. warm tap water and then in 1.5% sodium hypochlorite for 10 min, followed by three rinses with sterilized distilled water. Seeds are then placed on MS medium without hormones, containing Gamborg B5 vitamins, 3% sucrose, and 0.8% Oxoidagar. Seeds are germinated at 24° C. for 4 days in low light (<50 μMol/m2s) at 16 hr light. The cotyledon petiole explants with the cotyledon attached are excised from the in vitro seedlings, and inoculated with *Agrobacterium* by dipping the cut end of the petiole explant into the bacterial suspension. The explants are then cultured for 3 days on MS medium incl. vitamins containing 3.75 mg/l BAP, 3% sucrose, 0.5 g/l MES, pH 5.2, 0.5 mg/l GA3, 0.8% Oxoidagar at 24° C., 16 hr light. After three days of co-cultivation with *Agrobacterium*, the petiole explants are transferred to regeneration medium containing 3.75 mg/l BAP, 0.5 mg/l GA3, 0.5 g/l MES, pH 5.2, 300 mg/l timentin and selection agent until shoot regeneration. As soon as explants start to develop shoots, they are transferred to shoot elongation medium (A6, containing full strength MS medium including vitamins, 2% sucrose, 0.5% Oxoidagar, 100 mg/l myo-inositol, 40 mg/l adenine sulfate, 0.5 g/l MES, pH 5.8, 0.0025 mg/l BAP: 0.1 mg/l IBA, 300 mg/l timentin and selection agent).

Samples from both in vitro and greenhouse material of the primary transgenic plants (T0) are analyzed by qPCR using TaqMan probes to confirm the presence of T-DNA and to determine the number of T-DNA integrations.

Seed is produced from the primary transgenic plants by self-pollination. The second-generation plants are grown in greenhouse conditions and self-pollinated. The plants are analyzed by qPCR using TaqMan probes to confirm the presence of T-DNA and to determine the number of T-DNA integrations. Homozygous transgenic, heterozygous transgenic and azygous (null transgenic) plants are compared for their growth characteristics and yield.

Example 12

Engineering Stress-tolerant Corn Plants by Expressing PPSRP Genes

*Agrobacterium* cells harboring the genes and the maize ahas gene on the same plasmid are grown in YP medium supplemented with appropriate antibiotics for 1-3 days. A loop of *Agrobacterium* cells is collected and suspended in 2 ml M-LS-002 medium (LS-inf) and the tube containing *Agrobactium* cells is kept on a shaker for 1-3 hrs at 1,200 rpm.

Corncobs [genotype J553x(HIIIAxA188)] are harvested at 7-12 days after pollination. The cobs are sterilized in 20% CLOROX solution for 15 min followed by thorough rinse with sterile water. Immature embryos with size 0.8-2.0 mm are dissected into the tube containing *Agrobacterium* cells in LS-inf solution.

Agro-infection is carried out by keeping the tube horizontally in the laminar hood at room temperature for 30 min. Mixture of the agro infection is poured on to a plate containing the co-cultivation medium (M-LS-011). After the liquid agro-solution is piped out, the embryos are plated on the co-cultivation medium with schutellum side up and cultured in the dark at 22° C. for 2-4 days.

Embryos are transferred to M-MS-101 medium without selection. Seven to ten days later, embryos are transferred to M-LS401 medium containing 0.75 μM imazethapyr and grown for 4 weeks to select for transformed callus cells.

Plant regeneration is initiated by transferring resistant calli to M-LS-504 medium supplemented with 0.75 μM imazethapyr and grown under light at 26° C. for two to three weeks. Regenerated shoots are then transferred to rooting box with M-MS-607 medium (0.5 μM imazethapyr).

Plantlets with roots are transferred to potting mixture and grown in a growth chamber for a week, then transplanted to larger pots and maintained in greenhouse till maturity.

Example 13

Engineering Stress-Tolerant Wheat Plants by Expressing PPSRP Genes

The constructs pBPSSH004 and pBPSLVM018 are used to transform wheat as described below.

Transformation of wheat is performed with the method described by Ishida et al. (1996, Nature Biotech. 14745-50). Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are then screened for their improved stress tolerance according to the screening method described in Example 7 demonstrating that transgene expression confers stress tolerance.

Example 14

Monitoring Changes in mRNA Concentration of PpPP-1 in *Physcomitrella patens* Cultures Cold Treated DNA Microarray Slide Preparation PCR amplification was performed in 96 well plates from selected *Physcomitrella patens* ESTs cloned in the pBluescript vector. The PCR buffer set (Boehringer Mannheim) was employed for PCR reaction. Each PCR reaction mixture contains 10 μl of PCR Buffer without $MgCl_2$, 10 μl of $MgSO_4$, 3 μl of SK-Fwd primer (MWG-Biotech, Sequence: 5'-CGCCAAGCGCGCAATTAACCCTCACT-3' SEQ ID NO:42), 3 μl SK-Rev primer (MWG-Biotech, Sequence. 5'GCGTAATACGACTCACTAT AGGGCGA-3' SEQ ID NO:43), 2 μl dNTP, 1 μl Taq DNA polymerase (Roche), 72 μl water and 1 μl DNA template. After denaturing at 95° C. for three minutes, the PCR reactions were performed with 35 cycles of three consecutive steps including denaturing at 95° C. for 45 seconds, annealing at 63° C. for 45 seconds, and elongation at 72° C. for 60 seconds. The last elongation was 72° C. for 10 minutes. The PCR products were then purified with QIAquick PCR purification kit (Qiagen, Inc.), eluted with water and the DNA concentration measured at 260 nm in a spectrophotometer.

2 to 5 g of each PCR product were dried down and dissolved in 50 μl of DMSO. The PCR products were then formatted from 96 well plates to 384 well plates for printing. Microarray GenIII arrayer (Molecular Dynamics) was employed to print the PCR products to microarray slides (Molecular Dynamics) with the format recommended by the manufacturer. The printed spots were about 290 μm in diameter and were spaced about 320 μm from center to center. After printing, the slide was left in the dust free chamber for one hour to dry out. UV cross-link was performed with 600 μJ/mm. The cross-linked slides were ready for hybridization and were stored in dark and dry chambers.

Microarray Probe Synthesis

Total RNA was extracted from cold-treated *Physcomitrella patens* cultures (12 hours at 4° C. in the dark) following the RNA extraction method described in Ausubel et al. (Curr. Prot. in Mol. Biol. 1987, J. Wiley and Sons, New York). Oligotex mRNA midi kit (Qiagen Inc.) was applied to isolate mRNA from total RNA with an approach combining both batch and standard protocol recommended by the manufacturer. After binding the total RNA with Oligotex, the sample was centrifuged at 14,000 g to separate the Oligotex:mRNA with the liquid phase instead of running through a column. After four washes with OW2 buffer as described in batch protocol, the Oligotex:mRNA was resuspended in 400 μl OW2 and then collected by the column as the standard protocol. The mRNA was eluted following standard protocol.

Cy3 and Cy5 labeled cDNA probes were synthesized from mRNA with Superscript Choice System for cDNA synthesis (Gibco BRL). Both oligo-$(dT)_{25}$ primer (Genosys Biotechnologies) and Nonamer primer (Amersham Pharmacia Biotech) were mixed with mRNA to reach a total volume of 20 μl. The mixture was first heated at 70° C. for 10 minutes and then left at room temperature for 15 minutes before transferring to ice. Once the sample is on ice, add 8 μl First Strand Synthesis Buffer. 4 μl 0.1M DTT, 2 μl dNTP (Amersham Pharmacia Biotech), 2 μl Cy3- or Cy5-dCTP (Amersham Pharmacia Biotech), 2 μl RNase Inhibitor (Gibco BRL) and 2 μl SuperScript II Reverse Transcriptase. The first strand synthesis was performed at 42° C. for 8 hours and the mixture was then heated at 94° C. for three minutes after the reaction.

After the first strand synthesis, 4 μl of 2.5M sodium hydroxide was added to the reaction and the mixture was incubated at 37° C. for ten minutes. 20 μl of 2M MOPS (pH 5.0) and 500 μl of PB buffer (Qiagen Inc.) were then added to each reaction. The probe was then purified by the QIAquick PCR Purification Kit (Qiagen Inc.) with the protocol provided by the manufacturer.

cDNA Microarray Hybridization and Washes

The purified Cy3- and Cy5-labeled probes were mixed and vacuum died to give a final volume of 9 μl. 9 μl Microarray Hybridization Solution (Amersham Pharmacia Biotech) and 18 μl Formamide (Sigma) were then added to the cDNA probes to give a final volume of 36 μl. The mixture was applied to the printed microarray slide that was then covered with a clean dust-free cover slide with no air trapped. The hybridization was performed in a hybridization chamber at 42° C. for 16 to 20 hours. After the hybridization, the slides were washed two times with 0.5×SSC, 0.2% SDS at room temperature for 5 minutes and 15 minutes. Two times of stringent washes were performed with 0.25×SSC, 0.1% SDS at 55° C. for 10 and 30 minutes respectively. After the washes, the slides were briefly rinsed with Millipore water and dried under compressed nitrogen.

Scanning Microarray Data Analysis

The cDNA microarrays were scanned using the microarray GenIII Scanner (Molecular Dynamics) equipped with two laser channels. The scanned images were firstly viewed and adjusted in ImageQuant software (Molecular Dynamics) and then analyzed by ArrayVision software (Molecular Dynamics). The signal intensity for each spot was extracted by ArrayVision software (Molecular Dynamics) and transferred to Excel (Microsoft). The data obtained was normalized by dividing the difference of the intensity value and background and the difference of the control value and background. The ratio was then obtained by dividing the normalized data. The transcript level of PpPP-1 decreased 2 times as compared to the untreated control.

Example 15

Identification of PpPP2A-1 Orthologs

The *Brassica napus, Glycine max*, and *Oryza sativa* partial cDNAs (ESTs) for BnPP2A-1, BnPP2A-2, BnPP2A-3, GmPP2A-1, GmPP2A-2, GmPP2A-3, GmPP2A-4; GmPP2A-5, OsPP2A-1, OsPP2A-2, OsPP2A-3, OsPP2A-4, and OsPP2A-5 were identified in a privately licensed database by searching for ESTs with similarity to the *Physcomitrella patens* PP2A-1 nucleotide sequence, and the full-length cDNAs of the identified ESTs were sequenced. These particular clones were chosen for further analyses (see Table 6 below).

TABLE 6

| Gene name | Hyseq cloneID | Hyseq source | position for translation | vs. PpPP2A-1 identity/similarity | vs public identity/similarity |
|---|---|---|---|---|---|
| BnPP2A-1 | BN48706417 | canola | 150-1067 | 78%/86% | AAG52565: 96%/97% |
| BnPP2A-2 | BN51288093 | canola | 90-1046 | 42%/54% | AAC39460: 90%/95% |
| BnPP2A-3 | BN51387173 | canola | 155-1036 | 40%/54% | BAB09762: 92%/92% |
| OsPP2A-1 | OS41502678 | rice | 140-1081 | 88%/90% | AAD048068: 99%/99% |
| OsPP2A-2 | OS32806943 | rice | 173-1093 | 79%/86% | AAC72838: 96%/98% |
| OsPP2A-3 | OS35083313 | rice | 208-1155 | 42%/57% | AAA33545: 94%/98% |
| OsPP2A-4 | OS33003814 | rice | 58-978 | 88%/90% | AAD22116: 100%/100% |
| OsPP2A-5 | OS34738749 | rice | 104-1021 | 78%/87% | BAA92697: 78%/87% |
| GmPP2A-1 | GM50770660 | soybean | 97-1005 | 55%/67% | CAA87388: 55%/67% |
| GmPP2A-2 | GM48922444 | soybean | 28-975 | 41%/57% | BAA92244: 41%/57% |
| GmPP2A-3 | GM50131069 | soybean | 206-1144 | 88%/91% | BAA92699: 88%/91% |
| GmPP2A-4 | GM47171610 | soybean | 114-1082 | 43%/56% | CAA05491: 43%/56% |
| GmPP2A-5 | GM49671923 | soybean | 91-1008 | 78%/87% | BAA92697: 78%/87% |

Example 16

Greenhouse Screening of Corn Plants for Increased Growth/Yield and/or Increased Stress Tolerance High Throughput Drought Performance Screen Segregating transgenic corn seeds for a transformation event are planted in small pots. Each of these plants is uniquely labeled, sampled, and analyzed for transgene copy number. Transgene positive and negative plants are marked and paired with similar sizes for transplanting together to large pots. This provides a uniform and competitive environment for the transgene positive and negative plants. The large pots are watered to a certain percentage of the field water capacity of the soil depending the severity of water-stress desired. The soil water level is maintained by watering every other day. Plant growth and physiology traits such as height, stem diameter, leaf rolling, plant wilting, leaf extension rate, leaf water status, chlorophyll content and photosynthesis rate are measured during the growth period. After a period of growth, the above ground portion of the plants is harvested, and the fresh weight and dry weight of each plant are taken. A comparison of phenotype between the transgene positive and negative plants is then made.

Water Use Efficiency (WUE) Assay

Transgene positive and negative corn seedlings for a transformation event are transplanted into a pot with a given amount of soil and water. The pots are covered with caps that permit the seedlings to grow through but minimize water loss. Each pot is weighed periodically and water added to maintain the initial water content. At the end of the experiment, the fresh and dry weight of each plant are measured, the water consumed by each plant is calculated and WUE of each plant is computed. Plant growth and physiology traits such as WUE, height, stem diameter, leaf rolling, plant wilting, leaf extension rate, leaf water status, chlorophyll content and photosynthesis rate are measured during the experiment. A comparison of phenotype between the transgene positive and negative plants is then made.

Desiccation Assay

Segregating transgenic corn seeds for a transformation event are planted in small pots. These pots are kept in an area in the greenhouse that has uniform environmental conditions, and cultivated optimally. Each of these plants is uniquely labeled, sampled, and analyzed for transgene copy number. The plants are allowed to grow under theses conditions until they reach a predefined growth stage. Water is then withheld. Plant growth and physiology traits such as height, stem diameter, leaf rolling, plant wilting, leaf extension rate, leaf water status, chlorophyll content and photosynthesis rate are measured as stress intensity increases. A comparison of the phenotype between transgene positive and negative plants is then made.

Cycling Drought Assay

Segregating transgenic corn seeds for a transformation event are planted in small pots. These pots are kept in an area in the greenhouse that has uniform environmental conditions, and cultivated optimally. Each of these plants is uniquely labeled, sampled, and analyzed for transgene copy number. The plants are allowed to grow under theses conditions until they reach a predefined growth stage. Plants are then repeatedly watered to saturation at a fixed interval of time. This water/drought cycle is repeated for the duration of the experiment. Plant growth and physiology traits such as height, stem diameter, leaf rolling, leaf extension rate, leaf water status, chlorophyll content and photosynthesis rate are measured during the growth period. At the end of the experiment; the plants are harvested for above-ground fresh and dry weight. A comparison of the phenotype between transgene positive and negative plants is then made.

Example 17

Field Screening of Corn Plants for Increased Growth/Yield and/or Increased Tolerance Segregating Corn Screening Under Rain-free Conditions Managed-drought stress at a single location or multiple locations is used. Crop water availability is controlled by drip tape or overhead irrigation at a location that has less than 10 cm rainfall and minimum temperatures greater than 5° C. expected during an average 5-month season, or a location with expected in-season precipitation intercepted by an automated "rain-out shelter" which retracts to provide open field conditions when not required. Standard agronomic practices in the area are followed for soil preparation, planting, fertilization and pest control. Each plot is sown with seed segregating for the presence of a single transgenic insertion event. A Taqman transgene copy number assay is used on leaf samples to differentiate the transgenics from null-segregant control plants. Plants that have been genotyped in this manner are also scored for a range of phenotypes related to drought-tolerance, growth, and yield. These phenotypes include plant height, grain weight per plant, grain number per plant, ear number per plant, above ground dry-weight, leaf conductance to water vapor, leaf CO2 uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plants are used as the replicate unit per event.

Non-Segregating Corn Screening Under Rain-Free Conditions

Managed-drought stress at a single location or multiple locations is used. Crop water availability is controlled by drip tape or overhead irrigation at a location, which has less than 10 cm rainfall and minimum temperatures greater than 5° C. expected during an average 5-month season, or a location with expected in-season precipitation intercepted by an automated "rain-out shelter" which retracts to provide open field conditions when not required. Standard agronomic practices in the area are followed for soil preparation, planting, fertilization, and pest control. Trial layout is designed to pair a plot containing a non-segregating transgenic event with an adjacent plot of null segregant controls. Null segregants are progeny (or lines derived from the progeny) of a transgenic plant that does not contain the transgene due to Mendelian segregation. Additional replicated paired plots for a particular event are distributed around the trial. A range of phenotypes related to drought-tolerance, growth and yield are scored in the paired plots and estimated at the plot level. When the measurement technique could only be applied to individual plants, these are selected at random each time from within the plot. These phenotypes include plant height, grain weight per plant, grain number per plant, ear number per plant, above ground dry-weight, leaf conductance to water vapor, leaf CO2 uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plots are used as the replicate unit per event.

Multi-Location Corn Drought-Tolerance and Yield Screening

Five to twenty locations encompassing major corn growing regions are selected. These are widely distributed to provide a range of expected crop water availabilities based on average temperature, humidity, precipitation, and soil type. Crop water availability is not modified beyond standard agronomic practices. Trial layout is designed to pair a plot containing a non-segregating transgenic event with an adjacent plot of null-segregant controls. A range of phenotypes related to drought-tolerance, growth and yield are scored in the paired plots and estimated at the plot level. When the measurement technique could only be applied to individual plants, these are selected at random each time from within the plot. These phenotypes included plant height, grain weight per plant, grain number per plant, ear number per plant, above ground dry-weight, leaf conductance to water vapor, leaf CO2 uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plots are used as the replicate unit per event.

We claim:

1. An isolated nucleic acid selected from the group consisting of:

a) a polynucleotide comprising nucleotides 1 to 1014 of SEQ ID NO:5; and b) a polynucleotide encoding a polypeptide comprising amino acids 1 to 303 of SEQ ID NO:6.

2. The nucleic acid of claim 1, comprising nucleotides 1 to 1014 of SEQ ID NO:5.

3. The nucleic acid of claim 1, encoding a polypeptide comprising amino acids 1 to 303 of SEQ ID NO:6.

4. A vector comprising an isolated polynucleotide selected from the group consisting of:

a) a polynucleotide comprising nucleotides 1 to 1014 of SEQ ID NO:5; and b) a polynucleotide encoding a polypeptide comprising amino acids 1 to 303 of SEQ ID NO:6.

5. A transgenic plant cell comprising an isolated polynucleotide selected from the group consisting of:

a) a polynucleotide comprising nucleotides 1 to 1014 of SEQ ID NO:5; and b) a polynucleotide encoding a polypeptide comprising amino acids 1 to 303 of SEQ ID NO:6.

6. A transgenic plant comprising an isolated polynucleotide selected from the group consisting of:

a) a polynucleotide comprising nucleotides 1 to 1014 of SEQ ID NO:5; and b) a polynueleotide encoding a polypeptide comprising amino acids 1 to 303 of SEQ ID NO:6.

7. The transgenic plant of claim 6, further described as a monocot.

8. The transgenic plant of claim 6, further described as a dicot.

9. The transgenic plant of claim 6, wherein the plant is selected from the group consisting of maize, wheat, rye, oat, triticale, rice, barley, soybean, peanut, cotton, rapeseed, eanola, manihot, pepper, sunflower, tagetes, solanaceous plants, potato, tobacco, eggplant, tomato, Vicia species, pea, alfalfa, coffee, cacao, tea, Salix species, oil paint, coconut, perennial grass and a forage crop plant.

10. A plant seed which is true breeding for a transgene comprising an isolated polynucleotide selected from the group consisting of:

a) a polynucleotide comprising nucleotides 1 to 1014 of SEQ ID NO:5; and b) a polynucleotide encoding a polypeptide comprising amino acids 1 to 303 of SEQ ID NO:6.

11. The vector of claim 4, wherein the polynucleotide comprises nucleotides 1 to 1014 of SEQ ID NO:5.

12. The vector of claim 4, wherein the polynucleotide encodes the polypeptide comprising amino acids 1 to 303 of SEQ ID NO:6.

13. The transgenic plant of claim 6, wherein the polynucleotide comprises nucleotides 1 to 1014 of SEQ ID NO:5.

14. The transgenic plant of claim 6, wherein the polynucleotide encodes the polypeptide comprising amino acids 1 to 303 of SEQ ID NO:6.

15. The seed of claim 6, wherein the polynucleotide comprises nucleotides 1 to 1014 of SEQ ID NO:5.

16. The seed of claim 6, wherein the polynucleotide encodes the polypeptide comprising amino acids 1 to 303 of SEQ ID NO:6.

* * * * *

SEQUENCE LISTING

```
<160> NUMBER OF SEQ ID NOS: 46

<210> SEQ ID NO 1
<211> LENGTH: 708
<212> TYPE: DNA
<213> ORGANISM: Physcomitrella patens

<400> SEQUENCE: 1

gaagtcttcc atacgtggca tttccgtact ttcgaagaca ctcgtcatag aaaccataca     60

cttgggtgat ctgccgactc tcatgattgc cacgcagaat ggtaatacga tcaggatatc    120

gtacttttaa agccactagc agtgtagcag tttcaactga ataataacca cgatccacat    180

aatctcccat aaataagtaa ttggtgtctg gacacattcc tccaattcgg aagagttcag    240

caagatcatg aaactggcca tgaatatcac cacaaattgt gactggacac ttcactggct    300

gaacattatt ttcccgcatc aatatctcct tcgccttctc acatagtcct ctgacctcga    360

cctcggataa cggtttgcat tgtatgagct gagcaatctg tgtgtccagc tgcccattag    420

aggatatcgg aggcacactc atgtcgtccc tcctgttgcg cttccccttc tccacgctat    480

cgccctaccc tccgtttccg ctgatctccg cctcaaaaac caactccgac actctcgaaa    540

cgcaatctgc aacaccgaca acaaaaagaa aatcacgtga cgaaagaaag ggtgagaagc    600

aacagggcga aaaagaaaat cacggacgaa agaaagggtg agatgcaaca gggcgagagg    660

gggaacgcaa gaggaacgac agaggagcga cctacggtga gctggtgc                708


<210> SEQ ID NO 2
<211> LENGTH: 1279
<212> TYPE: DNA
<213> ORGANISM: Physcomitrella patens

<400> SEQUENCE: 2

cttgttctag ggttgcgatt gcgtttcgag agtgtcggag ttggtttttg aggcggagat     60

cagcggaaac ggagggtagg gcgatagcgt ggagaagggg aagcgcaaca ggagggacga    120

catgagtgtg cctccgatat cctctaatgg gcagctggac acacagattg ctcagctcat    180

acaatgcaaa ccgttatccg aggtcgaggt cagaggacta tgtgagaagg cgaaggagat    240

attgatgcgg gaaaataatg ttcagccagt gaagtgtcca gtcacaattt gtggtgatat    300

tcatggccag tttcatgatc ttgctgaact cttccgaatt ggaggaatgt gtccagacac    360

caattactta tttatgggag attatgtgga tcgtggttat tattcagttg aaactgctac    420

actgctagtg gctttaaaag tacgatatcc tgatcgtatt accattctgc gtggcaatca    480

tgagagtcgg cagatcaccc aagtgtatgg tttctatgac gagtgtcttc gaaagtacgg    540

aaatgccaac gtatggaaga tcttcactga cctgtttgat tattttcctt taacagcact    600

cgtagagtcg gagatttttt gtttacatgg agggctttcg ccaagcatcg attccttgga    660

ccacattcgg gacctggatc gagttcaaga ggttcctcat gaaggtccga tgtgtgatct    720
```

-continued

```
actttggtct gaccccgatg accgttgtgg ttggggcatt tctccccgtg gtgctggcta    780

cacatttggc caggatatat ctgagcagtt caatcacaac aacaatctga agttggtcgc    840

aagggcacat caattagtta tggagggcta caattgggga catgaacaca aggtggtcac    900

tattttcagc gcacctaatt attgctatcg ctgtggaaac atggcttcta tattggaagt    960

ggatgacaat atgggccaca ctttcattca gtttgaacca gccccgagac gaggtgaacc   1020

agatgtgaca aggcgcacgc cagactactt cttatagtgg gactttctga tagtagtttt   1080

taaagtatgc tttgagctat tttggatcgt ctgtagtcca tgcattcaat gatgtagatt   1140

ttcctcaggt tagcatggtg ttaccaagcg atagcagcct gaatgctgtc ataaccgcca   1200

caccatcata tgatatgtat ttcattgagc gggcatgcta ctctgcgctt gagatgtaag   1260

cgagtctcta tttggagtg                                                1279


<210> SEQ ID NO 3
<211> LENGTH: 311
<212> TYPE: PRT
<213> ORGANISM: Physcomitrella patens

<400> SEQUENCE: 3

Met Ser Val Pro Pro Ile Ser Ser Asn Gly Gln Leu Asp Thr Gln Ile
1               5                   10                  15

Ala Gln Leu Ile Gln Cys Lys Pro Leu Ser Glu Val Glu Val Arg Gly
            20                  25                  30

Leu Cys Glu Lys Ala Lys Glu Ile Leu Met Arg Glu Asn Asn Val Gln
        35                  40                  45

Pro Val Lys Cys Pro Val Thr Ile Cys Gly Asp Ile His Gly Gln Phe
    50                  55                  60

His Asp Leu Ala Glu Leu Phe Arg Ile Gly Gly Met Cys Pro Asp Thr
65                  70                  75                  80

Asn Tyr Leu Phe Met Gly Asp Tyr Val Asp Arg Gly Tyr Tyr Ser Val
                85                  90                  95

Glu Thr Ala Thr Leu Leu Val Ala Leu Lys Val Arg Tyr Pro Asp Arg
            100                 105                 110

Ile Thr Ile Leu Arg Gly Asn His Glu Ser Arg Gln Ile Thr Gln Val
        115                 120                 125

Tyr Gly Phe Tyr Asp Glu Cys Leu Arg Lys Tyr Gly Asn Ala Asn Val
    130                 135                 140

Trp Lys Ile Phe Thr Asp Leu Phe Asp Tyr Phe Pro Leu Thr Ala Leu
145                 150                 155                 160

Val Glu Ser Glu Ile Phe Cys Leu His Gly Gly Leu Ser Pro Ser Ile
                165                 170                 175

Asp Ser Leu Asp His Ile Arg Asp Leu Asp Arg Val Gln Glu Val Pro
            180                 185                 190

His Glu Gly Pro Met Cys Asp Leu Leu Trp Ser Asp Pro Asp Asp Arg
        195                 200                 205

Cys Gly Trp Gly Ile Ser Pro Arg Gly Ala Gly Tyr Thr Phe Gly Gln
    210                 215                 220

Asp Ile Ser Glu Gln Phe Asn His Asn Asn Asn Leu Lys Leu Val Ala
225                 230                 235                 240

Arg Ala His Gln Leu Val Met Glu Gly Tyr Asn Trp Gly His Glu His
                245                 250                 255

Lys Val Val Thr Ile Phe Ser Ala Pro Asn Tyr Cys Tyr Arg Cys Gly
            260                 265                 270
```

-continued

```
Asn Met Ala Ser Ile Leu Glu Val Asp Asp Asn Met Gly His Thr Phe
        275                 280                 285

Ile Gln Phe Glu Pro Ala Pro Arg Arg Gly Glu Pro Asp Val Thr Arg
    290                 295                 300

Arg Thr Pro Asp Tyr Phe Leu
305                 310
```

<210> SEQ ID NO 4
<211> LENGTH: 502
<212> TYPE: DNA
<213> ORGANISM: Physcomitrella patens

<400> SEQUENCE: 4

```
ggcacgaggt tttagctgcg cgcggaagaa gcagcgtgcg cggcggtggt tgtttggttt     60

ttgtttcctg tgttgctgtt agctgcgcaa aggaagggga ctggacacaa cgtgatggac    120

ttagatcagt ggcttgagaa agtgaagagc ggcaactacc tcttggaaga cgagctcaag    180

caactatgtg aatatgtgaa agaaatattg gtggaggaat ccaatgttca gcctgtcaac    240

agtcccgtta ctgtttgtgg cgatatccat ggccagtttc atgacttgat gaagcttttt    300

cagactggag gacacgtccc cagcacaaac tacatcttca tgggtgattt tgtggatcga    360

ggttacaaca gtttggaagt atttacaata cttttgctgc tgaaagcaag ataccctgct    420

catatgacgt tgttgagggg taaccatgag agtagacaga taactcaggt atatggattt    480

tatgacgaat gccagcggaa gt                                             502
```

<210> SEQ ID NO 5
<211> LENGTH: 1014
<212> TYPE: DNA
<213> ORGANISM: Physcomitrella patens

<400> SEQUENCE: 5

```
gcccttatcc cgggaggaag gggactggac acaacgtgat ggacttagat cagtggcttg     60

agaaagtgaa gagcggcaac tacctcttgg aagacgagct caagcaacta tgtgaatatg    120

tgaaagaaat attggtggag gaatccaatg ttcagcctgt caacagtccc gttactgttt    180

gtggcgatat ccatggccag tttcatgact tgatgaagct tttcagact ggaggacacg    240

tccccagcac aaactacatc ttcatgggtg attttgtgga tcgaggttac aacagtttgg    300

aagtatttac aatacttttg ctgctgaaag caagataccc tgctcatatg acgttgttga    360

ggggtaacca tgagagtaga cagataactc aggtatatgg attttatgac gaatgccagc    420

ggaagtatgg aaacccaaat gcttggcggt actgcactga tgtttttgac taccttacac    480

tctcagccat aatagatgga agggtgttgt gtgttcatgg aggtctgtct ccagacattc    540

ggacaattga tcagattagg gtgatagaga ggcagtgtga gattcctcat gaagggccat    600

tctgtgactt gatgtggagt gatcctgagg atatcgaaac ttgggctgtt agcccacgag    660

gtgctgggtg gctttttggt gcacgcgtta cctctgagtt caatcacata aacggattgg    720

agcttgtatg ccgtgcgcat caattagttc aagagggatt gaagtacatg tttcctgaca    780

aaggacttgt cacggtgtgg tccgctccaa actattgcta cagatgtgga aatgttgctt    840

caatcttaag cttcaacgaa aatatggaga gagatgtgaa attttttact gagaccgagg    900

agaaccaggc tatgatggca cctcgagcag gagttcctta cttcttgtag agatatttgt    960

cgcagatacc acatgacgac cggaaagcat catatggtgc gttaacgcaa gggc         1014
```

-continued

<210> SEQ ID NO 6
<211> LENGTH: 303
<212> TYPE: PRT
<213> ORGANISM: Physcomitrella patens

<400> SEQUENCE: 6

```
Met Asp Leu Asp Gln Trp Leu Glu Lys Val Lys Ser Gly Asn Tyr Leu
  1               5                  10                  15

Leu Glu Asp Glu Leu Lys Gln Leu Cys Glu Tyr Val Lys Glu Ile Leu
             20                  25                  30

Val Glu Glu Ser Asn Val Gln Pro Val Asn Ser Pro Val Thr Val Cys
         35                  40                  45

Gly Asp Ile His Gly Gln Phe His Asp Leu Met Lys Leu Phe Gln Thr
     50                  55                  60

Gly Gly His Val Pro Ser Thr Asn Tyr Ile Phe Met Gly Asp Phe Val
 65                  70                  75                  80

Asp Arg Gly Tyr Asn Ser Leu Glu Val Phe Thr Ile Leu Leu Leu Leu
                 85                  90                  95

Lys Ala Arg Tyr Pro Ala His Met Thr Leu Leu Arg Gly Asn His Glu
            100                 105                 110

Ser Arg Gln Ile Thr Gln Val Tyr Gly Phe Tyr Asp Glu Cys Gln Arg
        115                 120                 125

Lys Tyr Gly Asn Pro Asn Ala Trp Arg Tyr Cys Thr Asp Val Phe Asp
    130                 135                 140

Tyr Leu Thr Leu Ser Ala Ile Ile Asp Gly Arg Val Leu Cys Val His
145                 150                 155                 160

Gly Gly Leu Ser Pro Asp Ile Arg Thr Ile Asp Gln Ile Arg Val Ile
                165                 170                 175

Glu Arg Gln Cys Glu Ile Pro His Glu Gly Pro Phe Cys Asp Leu Met
            180                 185                 190

Trp Ser Asp Pro Glu Asp Ile Glu Thr Trp Ala Val Ser Pro Arg Gly
        195                 200                 205

Ala Gly Trp Leu Phe Gly Ala Arg Val Thr Ser Glu Phe Asn His Ile
    210                 215                 220

Asn Gly Leu Glu Leu Val Cys Arg Ala His Gln Leu Val Gln Glu Gly
225                 230                 235                 240

Leu Lys Tyr Met Phe Pro Asp Lys Gly Leu Val Thr Val Trp Ser Ala
                245                 250                 255

Pro Asn Tyr Cys Tyr Arg Cys Gly Asn Val Ala Ser Ile Leu Ser Phe
            260                 265                 270

Asn Glu Asn Met Glu Arg Asp Val Lys Phe Phe Thr Glu Thr Glu Glu
        275                 280                 285

Asn Gln Ala Met Met Ala Pro Arg Ala Gly Val Pro Tyr Phe Leu
    290                 295                 300
```

<210> SEQ ID NO 7
<211> LENGTH: 1243
<212> TYPE: DNA
<213> ORGANISM: Brassica napus

<400> SEQUENCE: 7

```
ttgaaattga aattcgcatt tttgctatgg ggaactgagt gatggtagat aattcgaatc      60

caaatccgca tccggatcca atactatccg aatccggatt ttgagttttt ggtcagatcg     120

gggatcggat ctgagggaag gagaagacga tgccggagac gggagacatc gatcgtcaga     180

tcgagcagct gatggagtgt aaagcgttgt ccgaggcgga ggtgaagacg ctgtgcgagc     240
```

-continued

```
aagcgagggc gattctggtg gaggagtgga atgttcagcc ggttaagtgt ccggtcaccg    300

tctgcggcga catccacggc cagttttacg atctgattga gctttttaag atcggtggtt    360

cttcgcctga caccaattat ctcttcatgg gcgattacgt agatcgaggg tattattctg    420

tggagacagt ctcgctcttg gtagcactca aagttcgcta cagagatagg cttaccatct    480

taagagggaa tcacgaaagc cgccaaatta ctcaagtgta tggattttat gatgagtgct    540

tgagaaaata tggaaatgct aatgtctgga aacacttcac tgaccttttt gattatcttc    600

ctcttacagc tctcatcgag agtcaggttt tctgtttaca tggagggctc tcaccttctt    660

tagatacact tgacaacatc cgttctctag atcgaatcca agaggttcca catgaaggac    720

ctatgtgtga tctgttatgg tccgatccag atgatcgatg cggttgggga atatctcctc    780

gtggcgcagg ctacacgttc ggacaagata tcgctactca gtttaaccac accaatggac    840

tcagtctgat ctcaagagca caccaacttg tcatggaagg ttataattgg tgccaagaaa    900

agaacgttgt gactgtgttt agcgccccaa actattgcta ccgatgcggc aacatggctg    960

ctattctaga gatagacgag aacatggacc agaacttcct tcagttcgat ccagccccac   1020

gtcaagtaga acccgaaact acacgcaaaa ctccagatta ctttttgtaa gtacccaaaa   1080

agaaaaaaac atccttaacc ttgttctgta atttcatttc ctgttcgtta aactcgtagt   1140

tgtctttttg gtttttagtt aagaatgtgt aacctttttaa ctgatacaaa gcgttacaaa  1200

agattctggt ccatatgaat aaggcaattg ttgttgagag cta                      1243


<210> SEQ ID NO 8
<211> LENGTH: 306
<212> TYPE: PRT
<213> ORGANISM: Brassica napus

<400> SEQUENCE: 8

Met Pro Glu Thr Gly Asp Ile Asp Arg Gln Ile Glu Gln Leu Met Glu
1               5                   10                  15

Cys Lys Ala Leu Ser Glu Ala Glu Val Lys Thr Leu Cys Glu Gln Ala
            20                  25                  30

Arg Ala Ile Leu Val Glu Glu Trp Asn Val Gln Pro Val Lys Cys Pro
        35                  40                  45

Val Thr Val Cys Gly Asp Ile His Gly Gln Phe Tyr Asp Leu Ile Glu
    50                  55                  60

Leu Phe Lys Ile Gly Gly Ser Ser Pro Asp Thr Asn Tyr Leu Phe Met
65                  70                  75                  80

Gly Asp Tyr Val Asp Arg Gly Tyr Tyr Ser Val Glu Thr Val Ser Leu
                85                  90                  95

Leu Val Ala Leu Lys Val Arg Tyr Arg Asp Arg Leu Thr Ile Leu Arg
            100                 105                 110

Gly Asn His Glu Ser Arg Gln Ile Thr Gln Val Tyr Gly Phe Tyr Asp
        115                 120                 125

Glu Cys Leu Arg Lys Tyr Gly Asn Ala Asn Val Trp Lys His Phe Thr
    130                 135                 140

Asp Leu Phe Asp Tyr Leu Pro Leu Thr Ala Leu Ile Glu Ser Gln Val
145                 150                 155                 160

Phe Cys Leu His Gly Gly Leu Ser Pro Ser Leu Asp Thr Leu Asp Asn
                165                 170                 175

Ile Arg Ser Leu Asp Arg Ile Gln Glu Val Pro His Glu Gly Pro Met
            180                 185                 190
```

-continued

```
Cys Asp Leu Leu Trp Ser Asp Pro Asp Asp Arg Cys Gly Trp Gly Ile
        195                 200                 205

Ser Pro Arg Gly Ala Gly Tyr Thr Phe Gly Gln Asp Ile Ala Thr Gln
    210                 215                 220

Phe Asn His Thr Asn Gly Leu Ser Leu Ile Ser Arg Ala His Gln Leu
225                 230                 235                 240

Val Met Glu Gly Tyr Asn Trp Cys Gln Glu Lys Asn Val Val Thr Val
                245                 250                 255

Phe Ser Ala Pro Asn Tyr Cys Tyr Arg Cys Gly Asn Met Ala Ala Ile
            260                 265                 270

Leu Glu Ile Asp Glu Asn Met Asp Gln Asn Phe Leu Gln Phe Asp Pro
        275                 280                 285

Ala Pro Arg Gln Val Glu Pro Glu Thr Thr Arg Lys Thr Pro Asp Tyr
    290                 295                 300

Phe Leu
305


<210> SEQ ID NO 9
<211> LENGTH: 1259
<212> TYPE: DNA
<213> ORGANISM: Brassica napus

<400> SEQUENCE: 9

attttattca cctacttaac tctctccgtc gtcggatttg tattcgtttc cgagaaaggg     60

ggtttaaggt ttttaggctt gtcggtacga tggacgagaa tttgctggac gatataatac    120

ggcggctgtt ggagactaac aacgggaagc aggtgaagct actcgaggct gagatacgcc    180

agctctgctc tgcttccaaa gaggtttttc tcagccagcc taatctcctc gagctcgagg    240

ctcctatcaa gatttgcggt gatgttcatg gtcagtttcc agacctcttg cggttgtttg    300

agtacggcgg ctaccctcca gctgcaaatt acttgttcct cggagactac gttgatcgtg    360

gtaagcggag catagagacc atatgccttc tccttgccta caagctcaaa tacaagctca    420

acttctttct cctcagaggc aatcacgaat gcgcttctat caaccgtgtt tacggcttct    480

acgatgagtg caagagaaga tacaacgtgc gcctgtggaa gagtttcacc gactgtttca    540

actgcctccc cgttgctgct ctcatcgacg acaagatcct ctgtatgcac ggtggacttt    600

ctcctgatct caagaccttg gatgatatca ggcggattcc tcgtcctgtt gatgttcctg    660

atcagggcgt cctttgtgat ttgttatggg ctgatcctga caaagaaatc caaggctggg    720

gggagaatga cagaggtgtg tcttatacat ttggtcccga caaagtggct gagttccttc    780

agactcatga ccttgatctt gtttgccgag ctcatcaggt tgtagaagat ggatatgagt    840

tctttgcaaa gagacaactg gtgacaatat tctctgcacc caactactgt ggtgagtttg    900

acaatgctgg cgcaatgatg agtgttgatg atagtttgac atgttctttc caaatcctca    960

agtcaactga gaagaaagga agatttggat acaacaacaa cgttcatagg ccaggaaccc   1020

cacctcataa ggggggaaaa ggtggttgag atgggggaat caagagaaga gtgaagccga   1080

agggttcgaa ctttatggtc aatgtaatgt aggtgatttg aggcaatacc gtttgttgtt   1140

ttgtttgatt gatgcaaaga ttttggtttt gttagattgt tttgtaactg atacggcatt   1200

tttcaactta agaaagttgg gtttataaaa aaaaaaaaaa aaaaaaaaaa aaaaaaaaa    1259


<210> SEQ ID NO 10
<211> LENGTH: 319
<212> TYPE: PRT
<213> ORGANISM: Brassica napus
```

<400> SEQUENCE: 10

Met Asp Glu Asn Leu Leu Asp Asp Ile Ile Arg Arg Leu Leu Glu Thr
1 5 10 15

Asn Asn Gly Lys Gln Val Lys Leu Leu Glu Ala Glu Ile Arg Gln Leu
20 25 30

Cys Ser Ala Ser Lys Glu Val Phe Leu Ser Gln Pro Asn Leu Leu Glu
35 40 45

Leu Glu Ala Pro Ile Lys Ile Cys Gly Asp Val His Gly Gln Phe Pro
50 55 60

Asp Leu Leu Arg Leu Phe Glu Tyr Gly Gly Tyr Pro Pro Ala Ala Asn
65 70 75 80

Tyr Leu Phe Leu Gly Asp Tyr Val Asp Arg Gly Lys Arg Ser Ile Glu
85 90 95

Thr Ile Cys Leu Leu Leu Ala Tyr Lys Leu Lys Tyr Lys Leu Asn Phe
100 105 110

Phe Leu Leu Arg Gly Asn His Glu Cys Ala Ser Ile Asn Arg Val Tyr
115 120 125

Gly Phe Tyr Asp Glu Cys Lys Arg Arg Tyr Asn Val Arg Leu Trp Lys
130 135 140

Ser Phe Thr Asp Cys Phe Asn Cys Leu Pro Val Ala Ala Leu Ile Asp
145 150 155 160

Asp Lys Ile Leu Cys Met His Gly Gly Leu Ser Pro Asp Leu Lys Thr
165 170 175

Leu Asp Asp Ile Arg Arg Ile Pro Arg Pro Val Asp Val Pro Asp Gln
180 185 190

Gly Val Leu Cys Asp Leu Leu Trp Ala Asp Pro Asp Lys Glu Ile Gln
195 200 205

Gly Trp Gly Glu Asn Asp Arg Gly Val Ser Tyr Thr Phe Gly Pro Asp
210 215 220

Lys Val Ala Glu Phe Leu Gln Thr His Asp Leu Asp Leu Val Cys Arg
225 230 235 240

Ala His Gln Val Val Glu Asp Gly Tyr Glu Phe Phe Ala Lys Arg Gln
245 250 255

Leu Val Thr Ile Phe Ser Ala Pro Asn Tyr Cys Gly Glu Phe Asp Asn
260 265 270

Ala Gly Ala Met Met Ser Val Asp Asp Ser Leu Thr Cys Ser Phe Gln
275 280 285

Ile Leu Lys Ser Thr Glu Lys Lys Gly Arg Phe Gly Tyr Asn Asn Asn
290 295 300

Val His Arg Pro Gly Thr Pro Pro His Lys Gly Gly Lys Gly Gly
305 310 315

<210> SEQ ID NO 11
<211> LENGTH: 1331
<212> TYPE: DNA
<213> ORGANISM: Brassica napus

<400> SEQUENCE: 11
ggcgaaaact tttttggtct gaagatcgag aaaagatttc gaaaatcaaa tttgggttcc 60
tgggcaatcg atttatgtcc gaaagattga agcttttgta agataaaaag atcgattggt 120
gttgttaagt ttcgatcgcg tgggggtctt tgtaatgacg cagcaagggc agggaagcat 180
ggaccctgcc gttctcgacg acatcattcg tcgtttgttg gattacagaa accctaagcc 240

-continued

```
tggaaccaaa caggtcatgc tcaacgagtc tgagatccga cagctttgca gcgtgtctag    300

agagattttc cttcagcagc ctaacctcct tgagctcgag gctccaatta agatctgtgg    360

tgatattcat ggacagtact cagatctact gaggctattt gagtacggag gcttacctcc    420

tgcagctaac tatctattcc taggagatta cgtggatcgc gggaagcaga gcctagaaac    480

aatctgcctt ctccttgcct acaagatcaa ataccctgag aacttcttcc tcctaagagg    540

caaccacgaa tgcgcttcca tcaaccgaat ctacggattc tacgatgaac gtaaacgcag    600

gttcagtgtc agactctgga aagtgtttac agattctttc aactgcctcc ctgtagctgc    660

tgtaatagac gataagatat tgtgtatgca cggtggcctt tctcctgatt tgaccagcgt    720

ggaacagatt aagaacatta agcgacctac cgatgttccg gactccggtt tgttatgtga    780

tctgctttgg tctgatccga gcaaagatgt gaaaggctgg gggatgaatg accgtggagt    840

ttcttacacg tttgggcctg ataaagttgc tgagtttttg ataaagaatg atatggatct    900

catctgtcgt gctcaccagg ttgtagagga tggttatgag ttctttgcgg atagacagct    960

tgttactata ttttcagctc ctaattactg tggtgaattc gataatgctg gtgctatgat   1020

gagtgttgat gagagttaat gtgctctttt caaattctta agcctgcgga tcggaggcct   1080

cggttcttat gagttagagc ctcactggaa agaagacgaa attggcgaga tgaaaacggg   1140

agagagagag agagacattt gaaactcccg gagactttgt cctgaggcct ttgcaagaag   1200

gcaggaaaaa aaaacacagt gttacatgtt atatcatata atcttatttg aacttttgta   1260

atttcttttc tcaaaacttt tatgttatta aaaaaaaaaa aaaaaaaaaa aaaaaaaaaa   1320

aaaaaaaaaa a                                                        1331
```

<210> SEQ ID NO 12
<211> LENGTH: 294
<212> TYPE: PRT
<213> ORGANISM: Brassica napus

<400> SEQUENCE: 12

```
Met Thr Gln Gln Gly Gln Gly Ser Met Asp Pro Ala Val Leu Asp Asp
  1               5                  10                  15

Ile Ile Arg Arg Leu Leu Asp Tyr Arg Asn Pro Lys Pro Gly Thr Lys
             20                  25                  30

Gln Val Met Leu Asn Glu Ser Glu Ile Arg Gln Leu Cys Ser Val Ser
         35                  40                  45

Arg Glu Ile Phe Leu Gln Gln Pro Asn Leu Leu Glu Leu Glu Ala Pro
     50                  55                  60

Ile Lys Ile Cys Gly Asp Ile His Gly Gln Tyr Ser Asp Leu Leu Arg
 65                  70                  75                  80

Leu Phe Glu Tyr Gly Gly Leu Pro Pro Ala Ala Asn Tyr Leu Phe Leu
                 85                  90                  95

Gly Asp Tyr Val Asp Arg Gly Lys Gln Ser Leu Glu Thr Ile Cys Leu
            100                 105                 110

Leu Leu Ala Tyr Lys Ile Lys Tyr Pro Glu Asn Phe Phe Leu Leu Arg
        115                 120                 125

Gly Asn His Glu Cys Ala Ser Ile Asn Arg Ile Tyr Gly Phe Tyr Asp
    130                 135                 140

Glu Arg Lys Arg Arg Phe Ser Val Arg Leu Trp Lys Val Phe Thr Asp
145                 150                 155                 160

Ser Phe Asn Cys Leu Pro Val Ala Ala Val Ile Asp Asp Lys Ile Leu
                165                 170                 175
```

-continued

```
Cys Met His Gly Gly Leu Ser Pro Asp Leu Thr Ser Val Glu Gln Ile
            180                 185                 190

Lys Asn Ile Lys Arg Pro Thr Asp Val Pro Asp Ser Gly Leu Leu Cys
        195                 200                 205

Asp Leu Leu Trp Ser Asp Pro Ser Lys Asp Val Lys Gly Trp Gly Met
    210                 215                 220

Asn Asp Arg Gly Val Ser Tyr Thr Phe Gly Pro Asp Lys Val Ala Glu
225                 230                 235                 240

Phe Leu Ile Lys Asn Asp Met Asp Leu Ile Cys Arg Ala His Gln Val
                245                 250                 255

Val Glu Asp Gly Tyr Glu Phe Phe Ala Asp Arg Gln Leu Val Thr Ile
            260                 265                 270

Phe Ser Ala Pro Asn Tyr Cys Gly Glu Phe Asp Asn Ala Gly Ala Met
        275                 280                 285

Met Ser Val Asp Glu Ser
    290
```

<210> SEQ ID NO 13
<211> LENGTH: 1184
<212> TYPE: DNA
<213> ORGANISM: Glycine max

<400> SEQUENCE: 13

```
cctaacccat cgttcgcacg gagccgtggt ggttctggct ctgtcctttt ttcctttctc      60

tcgttaccag aaccagaaga accatttgtg gccaacatgg atttggacca gtggatctcc     120

aaggtcaaag agggccagca tcttcttgaa gacgagcttc aacttctctg cgaatatgta     180

aaagagatcc ttatcgagga gtccaatgtg cagcctgtca atagtccagt gactgtttgt     240

ggtgatattc atggtcaatt ccatgatcta atgaaacttt tccagactgg gggtcatgtg     300

cctgagacaa attatatttt tatgggagac tttgttgatc gaggttacaa tagtcttgaa     360

gtttttacca tccttttact tctaaaagct agatacccag ctaatattac tcttttacgt     420

ggaaatcatg aaagtagaca attaacccag gtctatggat tttatgatga atgccagagg     480

aagtatggca atgccaatgc ttggcggtat tgtacagatg tgtttgacta tttaacactt     540

tctgcaatta ttgatggaac tgtgctttgt gttcatgggg gcctttctcc tgacattcga     600

acaattgatc agataagggt cattgaccgg aactgtgaaa ttcctcatga gggtcctttc     660

tgtgatctaa tgtggagtga tcctgaagat attgaaacat gggcagtcag tccccgtgga     720

gcaggttggc tttttggatc cagggtcact tcggagttca atcacataaa taaccttgat     780

cttgtttgtc gagcgcacca actcgttcag gaaggcctta agtatatgtt ccaagataaa     840

ggccttgtaa ctgtatggtc tgcacctaat tactgttacc gatgtggaaa tgtagcttct     900

attctgagtt tcaatgaaaa tatggaaaga gaagttaaat ttttcaccga aacagaggag     960

aacaatcaga tgagagggcc caggacaggc gttccatatt tcttataagt tggtgcaaat    1020

tttgttttga atttattgta aaattagaca ctcatgtatt tatgctttgc cttttaaagg    1080

tggattttat tggtcacaag attaccaatc aaactatatc ttagctctgg gtcgcacaga    1140

taattttatg tttaaatttt tattgaaaaa aaaaaaaaaa aaaa                     1184
```

<210> SEQ ID NO 14
<211> LENGTH: 303
<212> TYPE: PRT
<213> ORGANISM: Glycine max

<400> SEQUENCE: 14

-continued

```
Met Asp Leu Asp Gln Trp Ile Ser Lys Val Lys Glu Gly Gln His Leu
  1               5                  10                  15

Leu Glu Asp Glu Leu Gln Leu Leu Cys Glu Tyr Val Lys Glu Ile Leu
             20                  25                  30

Ile Glu Glu Ser Asn Val Gln Pro Val Asn Ser Pro Val Thr Val Cys
         35                  40                  45

Gly Asp Ile His Gly Gln Phe His Asp Leu Met Lys Leu Phe Gln Thr
     50                  55                  60

Gly Gly His Val Pro Glu Thr Asn Tyr Ile Phe Met Gly Asp Phe Val
 65                  70                  75                  80

Asp Arg Gly Tyr Asn Ser Leu Glu Val Phe Thr Ile Leu Leu Leu Leu
                 85                  90                  95

Lys Ala Arg Tyr Pro Ala Asn Ile Thr Leu Leu Arg Gly Asn His Glu
            100                 105                 110

Ser Arg Gln Leu Thr Gln Val Tyr Gly Phe Tyr Asp Glu Cys Gln Arg
        115                 120                 125

Lys Tyr Gly Asn Ala Asn Ala Trp Arg Tyr Cys Thr Asp Val Phe Asp
    130                 135                 140

Tyr Leu Thr Leu Ser Ala Ile Ile Asp Gly Thr Val Leu Cys Val His
145                 150                 155                 160

Gly Gly Leu Ser Pro Asp Ile Arg Thr Ile Asp Gln Ile Arg Val Ile
                165                 170                 175

Asp Arg Asn Cys Glu Ile Pro His Glu Gly Pro Phe Cys Asp Leu Met
            180                 185                 190

Trp Ser Asp Pro Glu Asp Ile Glu Thr Trp Ala Val Ser Pro Arg Gly
        195                 200                 205

Ala Gly Trp Leu Phe Gly Ser Arg Val Thr Ser Glu Phe Asn His Ile
    210                 215                 220

Asn Asn Leu Asp Leu Val Cys Arg Ala His Gln Leu Val Gln Glu Gly
225                 230                 235                 240

Leu Lys Tyr Met Phe Gln Asp Lys Gly Leu Val Thr Val Trp Ser Ala
                245                 250                 255

Pro Asn Tyr Cys Tyr Arg Cys Gly Asn Val Ala Ser Ile Leu Ser Phe
            260                 265                 270

Asn Glu Asn Met Glu Arg Glu Val Lys Phe Phe Thr Glu Thr Glu Glu
        275                 280                 285

Asn Asn Gln Met Arg Gly Pro Arg Thr Gly Val Pro Tyr Phe Leu
    290                 295                 300
```

<210> SEQ ID NO 15
<211> LENGTH: 1417
<212> TYPE: DNA
<213> ORGANISM: Glycine max

<400> SEQUENCE: 15

```
aagaagaaga ggttttgatc ggatgcgatg agcacacagg ggcaagtgat tattgatgag      60

gcggttctgg atgacataat ccggcgctta acggaggtcc gactggcccg acccggcaag     120

caggttcagc tctccgagtc tgagatcaag caactctgcg tcgcttccag agacatcttc     180

attaaccagc ccaatttgct tgaactcgaa gcccccatca agatttgtgg tgacattcat     240

gggcagtaca gtgatttgtt aaggctattt gagtatgggg gtttgcctcc tactgcgaat     300

tatctctttt tgggggaata cgtggaccgt gggaagcaga gcttagaaac catatgtctt     360

ttgcttgcgt ataaaatcaa atatccagaa aactttttcc tgttaagggg gaatcatgag     420
```

-continued

```
tgtgcttcca ttaataggat ttatgggttt tatgatgaat gtaagcgaag gtttaacgtg    480

aggctttgga aagcctttac cgactgtttt aacttccttc ctgtggcagc ccttatagat    540

gataaaatat tgtgcatgca tggtggtctt tcccctgaac tcacaaactt ggatgaaatc    600

aggaatctac ctcgtcctac tgcgattccc gacaccggct tgctttgtga tttgctttgg    660

tctgatcctg gtagggatgt gaagggttgg ggtatgaatg acagaggagt gtcctacacc    720

tttggccctg ataaggtcgc tgagttcttg acaaagcatg acttggacct catttgtcgt    780

gctcatcagg ttgtagagga tgggtatgaa ttctttgctg ataggcaact tgttacgata    840

ttttcagctc caaactattg tggtgaattt gacaatgctg gtgcgatgat gagtgtggac    900

gaaaacttga tgtgctcatt tcagattctt aagcctgcag agaaaaaatc aaagtttgtg    960

atgtcaaaca agatgtgatg gttggcacat cactgtcaag taattaacca agatgtattc   1020

gtggagctaa attaaatcct gaagatttag attgcatggt cttaagttct atctattctg   1080

aggtgatgat gatgaacaaa caagtttact gctataacat ccagtcaggc agtgagcatg   1140

aggtactaca agagatatta agcactgttg gatggccata aaagcaaagg cttttatctt   1200

tttttttctt ttcttgtttt ataattattc tgcaacacaa tatgtacata tatgtgttgt   1260

agatgctctg gaaatgacct tctttgctct gaaaggtcct cttagactat cgatttacac   1320

tgatagagca gtttgtgttg atgattgtgg ccaattttat ccagttagta aaggtgcaat   1380

tgatggattt tatggtttaa aaaaaaaaaa aaaaaaa                            1417
```

<210> SEQ ID NO 16
<211> LENGTH: 316
<212> TYPE: PRT
<213> ORGANISM: Glycine max

<400> SEQUENCE: 16

```
Met Ser Thr Gln Gly Gln Val Ile Ile Asp Glu Ala Val Leu Asp Asp
  1               5                  10                  15

Ile Ile Arg Arg Leu Thr Glu Val Arg Leu Ala Arg Pro Gly Lys Gln
             20                  25                  30

Val Gln Leu Ser Glu Ser Glu Ile Lys Gln Leu Cys Val Ala Ser Arg
         35                  40                  45

Asp Ile Phe Ile Asn Gln Pro Asn Leu Leu Glu Leu Glu Ala Pro Ile
     50                  55                  60

Lys Ile Cys Gly Asp Ile His Gly Gln Tyr Ser Asp Leu Leu Arg Leu
 65                  70                  75                  80

Phe Glu Tyr Gly Gly Leu Pro Pro Thr Ala Asn Tyr Leu Phe Leu Gly
                 85                  90                  95

Glu Tyr Val Asp Arg Gly Lys Gln Ser Leu Glu Thr Ile Cys Leu Leu
            100                 105                 110

Leu Ala Tyr Lys Ile Lys Tyr Pro Glu Asn Phe Phe Leu Leu Arg Gly
        115                 120                 125

Asn His Glu Cys Ala Ser Ile Asn Arg Ile Tyr Gly Phe Tyr Asp Glu
    130                 135                 140

Cys Lys Arg Arg Phe Asn Val Arg Leu Trp Lys Ala Phe Thr Asp Cys
145                 150                 155                 160

Phe Asn Phe Leu Pro Val Ala Ala Leu Ile Asp Asp Lys Ile Leu Cys
                165                 170                 175

Met His Gly Gly Leu Ser Pro Glu Leu Thr Asn Leu Asp Glu Ile Arg
            180                 185                 190
```

-continued

```
Asn Leu Pro Arg Pro Thr Ala Ile Pro Asp Thr Gly Leu Leu Cys Asp
        195                 200                 205

Leu Leu Trp Ser Asp Pro Gly Arg Asp Val Lys Gly Trp Gly Met Asn
    210                 215                 220

Asp Arg Gly Val Ser Tyr Thr Phe Gly Pro Asp Lys Val Ala Glu Phe
225                 230                 235                 240

Leu Thr Lys His Asp Leu Asp Leu Ile Cys Arg Ala His Gln Val Val
                245                 250                 255

Glu Asp Gly Tyr Glu Phe Phe Ala Asp Arg Gln Leu Val Thr Ile Phe
            260                 265                 270

Ser Ala Pro Asn Tyr Cys Gly Glu Phe Asp Asn Ala Gly Ala Met Met
        275                 280                 285

Ser Val Asp Glu Asn Leu Met Cys Ser Phe Gln Ile Leu Lys Pro Ala
    290                 295                 300

Glu Lys Lys Ser Lys Phe Val Met Ser Asn Lys Met
305                 310                 315


<210> SEQ ID NO 17
<211> LENGTH: 1587
<212> TYPE: DNA
<213> ORGANISM: Glycine max

<400> SEQUENCE: 17

tctttccctc cacaagaaaa aaaaatcaga aaaaggaaat gagagattgt tggacaccgt     60

gcaaatcaag cactttgctt gttatttcac gcgccctctc tccattttga cctccctttc    120

ctcttcgttc cccactcact gcaacggcgc cggagatccg tcgctctcct cctcctcctc    180

ctcctcctcc tcctcctccg ccgcgatggg cgccaattcc atgctctccg agtcctctca    240

cgatctcgac gaccagatct cccagctcat gcagtgcaag ccactctccg agcaacaggt    300

cagaggttta tgtgagaagg ctaaggagat tttaatggat gaaagtaatg ttcagcctgt    360

taaaagccct gtgacaattt gtggcgatat tcatgggcaa tttcatgatc ttgctgaact    420

gtttcgaatt ggagggaagt gtccagatac taactacttg tttatgggtg attatgtgga    480

ccggggttat tattcagttg agactgtatc gctccttgtg gcactgaaag ttcggtatcc    540

ccagcgaatt actattctta gaggaaacca tgaaagccgt cagattactc aagtatatgg    600

attttatgat gaatgcctta gaaagtatgg taatgctaat gtttggaaga cctttacaga    660

cctttttgat ttttttccat tgactgcatt ggttgaatct gaaatattct gtttgcatgg    720

tggactgtca ccttcaattg agacccttga taacataagg aactttgatc gtgttcaaga    780

ggttcctcat gaaggcccca tgtgtgatct attgtggtct gacccagatg acagatgtgg    840

ctggggaatt tctcctcgtg gtgctggata tacttttggc caggatatat ctgaacaatt    900

caatcacact aacagcctta aattgattgc tagagctcat cagcttgtta tggatggatt    960

taactgggct catgaacaaa aggtggttac catttttagt gcacctaact actgttaccg   1020

atgtgggaac atggcttcca tattggaggt tgatgattgc aagggtcaca cattcatcca   1080

gtttgaacct gctcctagga gaggagaacc tgatgtcact cgtagaacgc ctgattactt   1140

cttataatgt agctgttgaa tgtcatactg ttatatcatg gttacctcta ctgcactaat   1200

ttcaggtagt tgcgcatcct catatcacga gattgctgta aacatttaaa tccatggata   1260

tacacgttcc gtgcttttgg gggttgtcca aagactgctt tgatgtataa taggcaggta   1320

acattccact gattacactc gaggaattgc tggacacctt gtctggagaa gtcgccaaga   1380

tgatgtcata atacgtattg ttccagcaaa atgtggatat tttttgtttg ttttttcgtg   1440
```

-continued

```
tttatttttt gtatcttatg ttcagtaact cccttttatg gctttacaag ctatatgact   1500

ggattttgtt ggtcgtggat gtttttgtcg tgttctatca tttttcagtt aaagttgcat   1560

gatatagtga aaaaaaaaaa aaaaaaa                                       1587


<210> SEQ ID NO 18
<211> LENGTH: 313
<212> TYPE: PRT
<213> ORGANISM: Glycine max

<400> SEQUENCE: 18

Met Gly Ala Asn Ser Met Leu Ser Glu Ser Ser His Asp Leu Asp Asp
  1               5                  10                  15

Gln Ile Ser Gln Leu Met Gln Cys Lys Pro Leu Ser Glu Gln Gln Val
             20                  25                  30

Arg Gly Leu Cys Glu Lys Ala Lys Glu Ile Leu Met Asp Glu Ser Asn
         35                  40                  45

Val Gln Pro Val Lys Ser Pro Val Thr Ile Cys Gly Asp Ile His Gly
     50                  55                  60

Gln Phe His Asp Leu Ala Glu Leu Phe Arg Ile Gly Gly Lys Cys Pro
 65                  70                  75                  80

Asp Thr Asn Tyr Leu Phe Met Gly Asp Tyr Val Asp Arg Gly Tyr Tyr
                 85                  90                  95

Ser Val Glu Thr Val Ser Leu Leu Val Ala Leu Lys Val Arg Tyr Pro
            100                 105                 110

Gln Arg Ile Thr Ile Leu Arg Gly Asn His Glu Ser Arg Gln Ile Thr
        115                 120                 125

Gln Val Tyr Gly Phe Tyr Asp Glu Cys Leu Arg Lys Tyr Gly Asn Ala
    130                 135                 140

Asn Val Trp Lys Thr Phe Thr Asp Leu Phe Asp Phe Phe Pro Leu Thr
145                 150                 155                 160

Ala Leu Val Glu Ser Glu Ile Phe Cys Leu His Gly Gly Leu Ser Pro
                165                 170                 175

Ser Ile Glu Thr Leu Asp Asn Ile Arg Asn Phe Asp Arg Val Gln Glu
            180                 185                 190

Val Pro His Glu Gly Pro Met Cys Asp Leu Leu Trp Ser Asp Pro Asp
        195                 200                 205

Asp Arg Cys Gly Trp Gly Ile Ser Pro Arg Gly Ala Gly Tyr Thr Phe
    210                 215                 220

Gly Gln Asp Ile Ser Glu Gln Phe Asn His Thr Asn Ser Leu Lys Leu
225                 230                 235                 240

Ile Ala Arg Ala His Gln Leu Val Met Asp Gly Phe Asn Trp Ala His
                245                 250                 255

Glu Gln Lys Val Val Thr Ile Phe Ser Ala Pro Asn Tyr Cys Tyr Arg
            260                 265                 270

Cys Gly Asn Met Ala Ser Ile Leu Glu Val Asp Asp Cys Lys Gly His
        275                 280                 285

Thr Phe Ile Gln Phe Glu Pro Ala Pro Arg Arg Gly Glu Pro Asp Val
    290                 295                 300

Thr Arg Arg Thr Pro Asp Tyr Phe Leu
305                 310


<210> SEQ ID NO 19
<211> LENGTH: 1480
<212> TYPE: DNA
```

-continued

<213> ORGANISM: Glycine max

<400> SEQUENCE: 19

```
gctcactctt ccaactacta ctgttgttct tcttcgtcgt cttggccttc gcatcttcac     60
aatcacatcc aatagagaca cgttgacttt gctggaagaa gaagaagaag agaatggaac    120
aatcgctttt ggatgacata atcaatcgcc tcctcgaagt tcctacccta ccggctaagc    180
aggttcagct atccgagtcc gagatccgtc aactctgcgt agtttccaga gaaattttct    240
tgcaacaacc taatttattg gagctcgaag cacctattaa gatttgtggt gatgtacatg    300
ggcaatattc tgatctttta aggctttttg agtacggtgg attacctcct gaagccaact    360
atttgttttt gggggattat gttgatcgag ggaagcagag tttagaaaca atttgcctcc    420
tccttgctta taaaataaaa tatcctgaga actttttctt gttaagggga aaccatgaat    480
gtgcttctat aaaccggata tatggatttt atgatgagtg caagagaagg ttcaatgtaa    540
ggttatggaa gacatttaca gactgcttca attgcctgcc tgtggcagcc cttgtcgatg    600
aaaagatttt gtgtatgcat gggggacttt ctcccgactt aaataatttg gaccaaatta    660
gaaatttaca gcggcccaca gatgttcctg atacaggttt gctttgtgat ctgctttggt    720
ctgacccgag caaagatgtt caaggatggg gaatgaatga cagaggagtt tcatacacat    780
ttggtgctga taaggtctca caatttcttc agaaacatga tcttgatctt gtttgtcgtg    840
ctcatcaggt tgtggaagat ggatacgagt tctttgctaa tcgacaactt gtaacaatat    900
tttcagcacc taattattgt ggggagtttg acaatgctgg tgctatgatg agtgttgatg    960
agacgctaat gtgctctttc caaatattaa agccagctga taaaaaagca aagctcaatt   1020
ttggaagtac aaccactgct aagcctggaa actctccagc aggtgtaaag gttggaagat   1080
attagtcctt cctggatgcg aaagtgtgaa attaaatttg gctaaaagat tgctactact   1140
acggatcagc ttgggcttga actcctaatg gttgcaagaa ggggaaaatc aagttccatt   1200
tcgcctacta tgatattttg gaattgtaaa atcaaagaga acaccattat gaagtttgta   1260
aaccattgtt tattattggt acaaatttgc atttcaagat ggagagccat aatctccttg   1320
tcttccttgt acactaataa ctggtatatt ttcttaactg taagcttcac aagcgtagat   1380
ggatacatcc gaatctgttg ctgagaacca tttaaaaatg cttatacgat ttggcatata   1440
tggatggcag ttgaggctgg tgaaaaaaaa aaaaaaaaaa                         1480
```

<210> SEQ ID NO 20
<211> LENGTH: 323
<212> TYPE: PRT
<213> ORGANISM: Glycine max

<400> SEQUENCE: 20

```
Met Glu Gln Ser Leu Leu Asp Asp Ile Ile Asn Arg Leu Leu Glu Val
  1               5                  10                  15

Pro Thr Leu Pro Ala Lys Gln Val Gln Leu Ser Glu Ser Glu Ile Arg
             20                  25                  30

Gln Leu Cys Val Val Ser Arg Glu Ile Phe Leu Gln Gln Pro Asn Leu
         35                  40                  45

Leu Glu Leu Glu Ala Pro Ile Lys Ile Cys Gly Asp Val His Gly Gln
     50                  55                  60

Tyr Ser Asp Leu Leu Arg Leu Phe Glu Tyr Gly Gly Leu Pro Pro Glu
 65                  70                  75                  80

Ala Asn Tyr Leu Phe Leu Gly Asp Tyr Val Asp Arg Gly Lys Gln Ser
                 85                  90                  95
```

```
Leu Glu Thr Ile Cys Leu Leu Leu Ala Tyr Lys Ile Lys Tyr Pro Glu
            100                 105                 110

Asn Phe Phe Leu Leu Arg Gly Asn His Glu Cys Ala Ser Ile Asn Arg
        115                 120                 125

Ile Tyr Gly Phe Tyr Asp Glu Cys Lys Arg Arg Phe Asn Val Arg Leu
    130                 135                 140

Trp Lys Thr Phe Thr Asp Cys Phe Asn Cys Leu Pro Val Ala Ala Leu
145                 150                 155                 160

Val Asp Glu Lys Ile Leu Cys Met His Gly Gly Leu Ser Pro Asp Leu
                165                 170                 175

Asn Asn Leu Asp Gln Ile Arg Asn Leu Gln Arg Pro Thr Asp Val Pro
            180                 185                 190

Asp Thr Gly Leu Leu Cys Asp Leu Leu Trp Ser Asp Pro Ser Lys Asp
        195                 200                 205

Val Gln Gly Trp Gly Met Asn Asp Arg Gly Val Ser Tyr Thr Phe Gly
    210                 215                 220

Ala Asp Lys Val Ser Gln Phe Leu Gln Lys His Asp Leu Asp Leu Val
225                 230                 235                 240

Cys Arg Ala His Gln Val Val Glu Asp Gly Tyr Glu Phe Phe Ala Asn
                245                 250                 255

Arg Gln Leu Val Thr Ile Phe Ser Ala Pro Asn Tyr Cys Gly Glu Phe
            260                 265                 270

Asp Asn Ala Gly Ala Met Met Ser Val Asp Glu Thr Leu Met Cys Ser
        275                 280                 285

Phe Gln Ile Leu Lys Pro Ala Asp Lys Lys Ala Lys Leu Asn Phe Gly
    290                 295                 300

Ser Thr Thr Thr Ala Lys Pro Gly Asn Ser Pro Ala Gly Val Lys Val
305                 310                 315                 320

Gly Arg Tyr


<210> SEQ ID NO 21
<211> LENGTH: 1386
<212> TYPE: DNA
<213> ORGANISM: Glycine max

<400> SEQUENCE: 21

accgtcccgg tcgcgccaac cgccgcaacc cgaagaaacc gaatcgatct gagagaaggt      60

gcgatctcgg aggtgggagc caaacgaaac gatgccgtct cacgcggatc tggagcgaca     120

gatcgagcag ctgatggact gcaagcctct gtcggagtcg gaggtgaagg cgctgtgcga     180

tcaagcgagg acgattcttg tggaggagtg gaacgtgcaa ccggttaagt gccccgtcac     240

cgtctgcggc gatattcacg gccagttcta cgatctcatc gagctgtttc ggattggagg     300

gaacgctccc gataccaatt atctcttcat gggtgattat gtagatcgtg gatactattc     360

agtggagact gttacacttt tggtggcttt gaaagtccgt tatagagata gaatcacaat     420

tctcagggga aatcatgaaa gccgtcaaat tactcaagtg tatggcttct atgatgaatg     480

cttgagaaaa tatggaaatg cgaatgtctg gaaatacttt acagacttgt ttgattattt     540

gcctctgact gccctcattg agagtcagat tttctgcttg catggaggtc tctcaccttc     600

tttggataca ctggataaca tcagagcatt ggatcgtatt caagaggttc cacatgaagg     660

accaatgtgt gatctcttgt ggtctgaccc tgatgatcgc tgtggatggg gaatatctcc     720

acgtggtgca ggatacacat ttgggcagga tatagctgct cagtttaatc ataccaatgg     780
```

-continued

```
cctctccctg atatcgagag cacatcagct tgttatggaa ggattcaatt ggtgccagga    840

caagaatgtg gtgactgtat ttagtgctcc aaattactgt tatcgatgtg ggaatatggc    900

tgccatacta gaaataggag agaatatgga tcagaatttt cttcagtttg atccagctcc    960

caggcaaatt gagcctgaca ccacacgcaa gactccagat tattttttgt aacttcattt   1020

atctgcctgt ttgtagttac tgctttctgc cattactgta gatgtgtctt taaggaaagg   1080

agttttactg tgtaagtgga gggtggtcat caacataatt ctttcttttg gagtttacct   1140

gttgctgctg ccgctgcctt atctgtacaa gaaaccaata gaactgacac atgacaccaa   1200

ttggggttgt tgtatatttt tgggaggaag cagcataaca tggtatatct tttctgtaat   1260

ccttttttctt ttctttaaat taaatctcaa gttaaagagc agatttttga gtcctgacaa  1320

tgatgtcctt ttgagacttt tgatgatgcc aaatgaaatt gcaggttttc aaaaaaaaaa   1380

aaaaaa                                                              1386
```

```
<210> SEQ ID NO 22
<211> LENGTH: 306
<212> TYPE: PRT
<213> ORGANISM: Glycine max

<400> SEQUENCE: 22

Met Pro Ser His Ala Asp Leu Glu Arg Gln Ile Glu Gln Leu Met Asp
  1               5                  10                  15

Cys Lys Pro Leu Ser Glu Ser Glu Val Lys Ala Leu Cys Asp Gln Ala
             20                  25                  30

Arg Thr Ile Leu Val Glu Glu Trp Asn Val Gln Pro Val Lys Cys Pro
         35                  40                  45

Val Thr Val Cys Gly Asp Ile His Gly Gln Phe Tyr Asp Leu Ile Glu
     50                  55                  60

Leu Phe Arg Ile Gly Gly Asn Ala Pro Asp Thr Asn Tyr Leu Phe Met
 65                  70                  75                  80

Gly Asp Tyr Val Asp Arg Gly Tyr Tyr Ser Val Glu Thr Val Thr Leu
                 85                  90                  95

Leu Val Ala Leu Lys Val Arg Tyr Arg Asp Arg Ile Thr Ile Leu Arg
            100                 105                 110

Gly Asn His Glu Ser Arg Gln Ile Thr Gln Val Tyr Gly Phe Tyr Asp
        115                 120                 125

Glu Cys Leu Arg Lys Tyr Gly Asn Ala Asn Val Trp Lys Tyr Phe Thr
    130                 135                 140

Asp Leu Phe Asp Tyr Leu Pro Leu Thr Ala Leu Ile Glu Ser Gln Ile
145                 150                 155                 160

Phe Cys Leu His Gly Gly Leu Ser Pro Ser Leu Asp Thr Leu Asp Asn
                165                 170                 175

Ile Arg Ala Leu Asp Arg Ile Gln Glu Val Pro His Glu Gly Pro Met
            180                 185                 190

Cys Asp Leu Leu Trp Ser Asp Pro Asp Asp Arg Cys Gly Trp Gly Ile
        195                 200                 205

Ser Pro Arg Gly Ala Gly Tyr Thr Phe Gly Gln Asp Ile Ala Ala Gln
    210                 215                 220

Phe Asn His Thr Asn Gly Leu Ser Leu Ile Ser Arg Ala His Gln Leu
225                 230                 235                 240

Val Met Glu Gly Phe Asn Trp Cys Gln Asp Lys Asn Val Val Thr Val
                245                 250                 255

Phe Ser Ala Pro Asn Tyr Cys Tyr Arg Cys Gly Asn Met Ala Ala Ile
```

-continued

```
            260                 265                 270

Leu Glu Ile Gly Glu Asn Met Asp Gln Asn Phe Leu Gln Phe Asp Pro
        275                 280                 285

Ala Pro Arg Gln Ile Glu Pro Asp Thr Thr Arg Lys Thr Pro Asp Tyr
    290                 295                 300

Phe Leu
305


<210> SEQ ID NO 23
<211> LENGTH: 1487
<212> TYPE: DNA
<213> ORGANISM: Oryza sativa

<400> SEQUENCE: 23

gcgcccccca accgcatctc aatctctctc ctctctctct ctctccagct cgcctccccc      60

tcgccggcga cgagctctcc cccggctagg gttagaccag gtgcccctct tgtctgcggc     120

ggaggaggtg ggaggaagga tggaggagtc cgtgggctcg cgcggcggcg gcggcggcgg     180

cctggacgcc cagatcgagc agctcatgga gtgccgcccg ctctccgagc ccgaggtcaa     240

gacgttgtgc gagaaggcga aggagatatt gatggaagaa agcaacgttc agccagttaa     300

gagcccagtc acaatttgtg gtgatatcca tgggcaattc catgatctag tagagctctt     360

tcggattggt gggaagtgtc cagatacaaa ttatttgttt atgggagatt atgtagatcg     420

tggctactat tctgttgaga ctgttacact tttggttgca ctgaaggtgc gctacccaca     480

gcggattaca atccttcgtg gaaaccatga gagtcggcag atcacacagg tgtatggatt     540

ctacgacgaa tgcctacgaa agtatggaag tgcaaatgtc tggaagatct tcaccgatct     600

ttttgactat tttccattga cagcattggt tgaatcagag attttctgcc tccatggtgg     660

tttatcgcca tcaatcgaca atcttgatag tgttcgcagc ttagatcgtg ttcaagaggt     720

ccctcatgag ggaccaatgt gtgatcttct atggtctgac ccggatgatc gatgcggttg     780

gggcatatct cctcgtggtg ctggctacac ttttggccag gacatatcgg agcagtttaa     840

ccataccaat aatctcaaac ttgtagcccg ggctcatcaa ttagttatgg aaggatataa     900

ctgggcgcac gaacaaaagg tcgtgaccat attcagtgca cctaattatt gttatcgctg     960

tggcaacatg gcatccatcc tggaggttga tgactgcagg aatcacacat ttattcagtt    1020

tgaaccagct cctaggagag gtgaaccaga tgtgacacgg agaacacctg attatttcct    1080

ttaaattatc tgttgtaatt tgtattgttt tgtttctttt gtttctctaa gaccgcaata    1140

gtgagtgctg gtcagtaaaa ttttgttgga tccctttggt aactaaactg gccagcgata    1200

gcatgagaat gccgatgccc aaaaaaaatg tgaaacttat gcccctcatt gatcattgtg    1260

agaatggtgc tgtcatccag gatgcaacgc attgcatacg attcagtctc ttacccaccc    1320

ttcccaagcc atgtttaggt ggcattgtgt tgacagatat caaaattcca ttttggtata    1380

agctgcttga gttatgtatt ggctggtttt gtaactgatg tgcttggacc ttctatcatt    1440

aatgacagac aagctgatct ctcggttgcg aaaaaaaaaa aaaaaaa                  1487


<210> SEQ ID NO 24
<211> LENGTH: 314
<212> TYPE: PRT
<213> ORGANISM: Oryza sativa

<400> SEQUENCE: 24

Met Glu Glu Ser Val Gly Ser Arg Gly Gly Gly Gly Gly Gly Leu Asp
  1               5                  10                  15
```

-continued

```
Ala Gln Ile Glu Gln Leu Met Glu Cys Arg Pro Leu Ser Glu Pro Glu
                20                  25                  30

Val Lys Thr Leu Cys Glu Lys Ala Lys Glu Ile Leu Met Glu Glu Ser
            35                  40                  45

Asn Val Gln Pro Val Lys Ser Pro Val Thr Ile Cys Gly Asp Ile His
    50                  55                  60

Gly Gln Phe His Asp Leu Val Glu Leu Phe Arg Ile Gly Gly Lys Cys
65                  70                  75                  80

Pro Asp Thr Asn Tyr Leu Phe Met Gly Asp Tyr Val Asp Arg Gly Tyr
                85                  90                  95

Tyr Ser Val Glu Thr Val Thr Leu Leu Val Ala Leu Lys Val Arg Tyr
            100                 105                 110

Pro Gln Arg Ile Thr Ile Leu Arg Gly Asn His Glu Ser Arg Gln Ile
        115                 120                 125

Thr Gln Val Tyr Gly Phe Tyr Asp Glu Cys Leu Arg Lys Tyr Gly Ser
    130                 135                 140

Ala Asn Val Trp Lys Ile Phe Thr Asp Leu Phe Asp Tyr Phe Pro Leu
145                 150                 155                 160

Thr Ala Leu Val Glu Ser Glu Ile Phe Cys Leu His Gly Gly Leu Ser
                165                 170                 175

Pro Ser Ile Asp Asn Leu Asp Ser Val Arg Ser Leu Asp Arg Val Gln
            180                 185                 190

Glu Val Pro His Glu Gly Pro Met Cys Asp Leu Leu Trp Ser Asp Pro
        195                 200                 205

Asp Asp Arg Cys Gly Trp Gly Ile Ser Pro Arg Gly Ala Gly Tyr Thr
    210                 215                 220

Phe Gly Gln Asp Ile Ser Glu Gln Phe Asn His Thr Asn Asn Leu Lys
225                 230                 235                 240

Leu Val Ala Arg Ala His Gln Leu Val Met Glu Gly Tyr Asn Trp Ala
                245                 250                 255

His Glu Gln Lys Val Val Thr Ile Phe Ser Ala Pro Asn Tyr Cys Tyr
            260                 265                 270

Arg Cys Gly Asn Met Ala Ser Ile Leu Glu Val Asp Asp Cys Arg Asn
        275                 280                 285

His Thr Phe Ile Gln Phe Glu Pro Ala Pro Arg Arg Gly Glu Pro Asp
    290                 295                 300

Val Thr Arg Arg Thr Pro Asp Tyr Phe Leu
305                 310
```

```
<210> SEQ ID NO 25
<211> LENGTH: 1298
<212> TYPE: DNA
<213> ORGANISM: Oryza sativa

<400> SEQUENCE: 25

gaggcttgag ctccacctcc acctcctcca cctccaaccc ccgatccccc gcaaacccta      60

gccctctccc ccaccctcct cgccggcggc gagcggcggc ggcgcgcggc gggacccgga     120

gcccccagta gcgcctcctc cgtcctcccc tccctgaggt gcgggggaga ggatgccgtc     180

gtcgcacggg gatctggacc ggcagatcgc gcagctgcgg gagtgcaagc acctggcgga     240

gggggaggtg agggcgctgt gcgagcaggc gaaggccatc ctcatggagg agtggaacgt     300

gcagccggtg cggtgccccg tcacggtctg cggcgacatc cacggccagt tctacgacct     360

catcgagctc ttccgcatcg gcggcgaggc gcccgacacc aactacctct tcatgggcga     420
```

-continued

```
ctacgtcgac cgtggctact actcagtgga gactgtttcg ttgttggtgg ctttgaaagt    480

acgctacaga gatcgaatta caatattgag aggaaatcat gagagcagac aaatcactca    540

agtgtacggc ttctacgatg aatgcttgag aaagtatgga aatgcaaatg tatggaaata    600

ctttacagac ttgtttgatt atttgcctct cacagctctt atagaaaacc aggtgttctg    660

ccttcacggt ggtctctctc catcattgga tactttagat aacatccgtg ctcttgatcg    720

tatacaagag gttcctcatg aaggacccat gtgtgatctt ttgtggtctg acccagatga    780

cagatgcggg tggggaattt caccgagagg agcaggttat acatttgggc aagatatcgc    840

tcaacagttt aaccatacaa atggtctatc tctcatctca agggcacatc aacttgtaat    900

ggaaggattt aattggtgtc aggacaagaa tgttgtgacg gtcttcagtg caccaaacta    960

ctgttatcgc tgtggtaaca tggctgcaat tcttgagatt ggcgaaaaca tggatcagaa   1020

cttcctccaa tttgatccag ctcctcggca aattgaacca gacacaacac gcaagactcc   1080

cgactacttt ttgtaatttg tggtgttgac aattttaact cacctgtgtt gatgctcctc   1140

tcctccgcgg tgtcggggtc tgtagatctt ctgtccttag atacgggttc cacgagcccg   1200

gctgtatgtc tctcaattct tttgtttgga gattttgttg ctgcttctca acctttatac   1260

aagacgttaa aagttacatg cactggattt ttttctcc                           1298


<210> SEQ ID NO 26
<211> LENGTH: 307
<212> TYPE: PRT
<213> ORGANISM: Oryza sativa

<400> SEQUENCE: 26

Met Pro Ser Ser His Gly Asp Leu Asp Arg Gln Ile Ala Gln Leu Arg
1               5                   10                  15

Glu Cys Lys His Leu Ala Glu Gly Glu Val Arg Ala Leu Cys Glu Gln
            20                  25                  30

Ala Lys Ala Ile Leu Met Glu Glu Trp Asn Val Gln Pro Val Arg Cys
        35                  40                  45

Pro Val Thr Val Cys Gly Asp Ile His Gly Gln Phe Tyr Asp Leu Ile
    50                  55                  60

Glu Leu Phe Arg Ile Gly Gly Glu Ala Pro Asp Thr Asn Tyr Leu Phe
65                  70                  75                  80

Met Gly Asp Tyr Val Asp Arg Gly Tyr Tyr Ser Val Glu Thr Val Ser
                85                  90                  95

Leu Leu Val Ala Leu Lys Val Arg Tyr Arg Asp Arg Ile Thr Ile Leu
            100                 105                 110

Arg Gly Asn His Glu Ser Arg Gln Ile Thr Gln Val Tyr Gly Phe Tyr
        115                 120                 125

Asp Glu Cys Leu Arg Lys Tyr Gly Asn Ala Asn Val Trp Lys Tyr Phe
    130                 135                 140

Thr Asp Leu Phe Asp Tyr Leu Pro Leu Thr Ala Leu Ile Glu Asn Gln
145                 150                 155                 160

Val Phe Cys Leu His Gly Gly Leu Ser Pro Ser Leu Asp Thr Leu Asp
                165                 170                 175

Asn Ile Arg Ala Leu Asp Arg Ile Gln Glu Val Pro His Glu Gly Pro
            180                 185                 190

Met Cys Asp Leu Leu Trp Ser Asp Pro Asp Asp Arg Cys Gly Trp Gly
        195                 200                 205

Ile Ser Pro Arg Gly Ala Gly Tyr Thr Phe Gly Gln Asp Ile Ala Gln
```

-continued

```
    210                 215                 220

Gln Phe Asn His Thr Asn Gly Leu Ser Leu Ile Ser Arg Ala His Gln
225                 230                 235                 240

Leu Val Met Glu Gly Phe Asn Trp Cys Gln Asp Lys Asn Val Val Thr
                245                 250                 255

Val Phe Ser Ala Pro Asn Tyr Cys Tyr Arg Cys Gly Asn Met Ala Ala
            260                 265                 270

Ile Leu Glu Ile Gly Glu Asn Met Asp Gln Asn Phe Leu Gln Phe Asp
        275                 280                 285

Pro Ala Pro Arg Gln Ile Glu Pro Asp Thr Thr Arg Lys Thr Pro Asp
    290                 295                 300

Tyr Phe Leu
305


<210> SEQ ID NO 27
<211> LENGTH: 1497
<212> TYPE: DNA
<213> ORGANISM: Oryza sativa

<400> SEQUENCE: 27

ccaatgccaa gaacaagaaa tcagagagcc caagcaaaaa atccaatccg aatcccctcc     60

aaaaacccac caaacaatct cctccatctc caagaacaag aacaagagag catcctagaa    120

cattagggga taaaggagga ggagaagaag accaagaaaa gtttcgagag gagagggagg    180

agagttcaag aacttggaga gaaggggatg gatccggtgt tgctggacga catcatccgg    240

aggcttatcg aggtgaagaa tctgaagccg gggaagaacg cgcagctttc ggagtcggag    300

attaagcagc tctgcgcaac ctccaaggag atcttcctga atcagcccaa cctgctcgag    360

ctcgaggccc ccatcaaaat ctgcggtgat gttcatggac agtattctga tctcctgagg    420

ctgtttgatt atggtgggta tccacctcag tccaactatc tcttcttggg cgattatgtg    480

gaccggggaa agcaaagcct tgagacgata tgccttcttt tggcttataa gatcaagtac    540

cctgaaaact tcttcctact cagaggcaac catgaatgtg catcggtcaa ccgcatctat    600

ggattttatg acgagtgcaa gcgcagattc agtgtaaaac tctggaagac ttttactgac    660

tgttttaact gcttaccagt ggcagcattg atagatgaaa agattctttg tatgcacgga    720

ggtctttctc cagagttgaa taagctggat caaatactca acctcaaccg ccccacggat    780

gtgcctgata ctgggttact ttgtgatctc ctttggtccg atccatccaa tgacgcacaa    840

gggtgggcta tgaatgatcg aggtgtctca tatacattcg ggccagacaa agtgtctgaa    900

tttcttgaga agcatgattt agacctcatc tgtcgagccc atcaggttgt cgaagatggg    960

tacgagttct ttgctaaccg ccaacttgta acaatattct cggcccctaa ttactgtgga   1020

gaatttgata atgctggtgc catgatgagt gtagatgata cactgatgtg ctcttttcaa   1080

atactaaaac cagcgaggaa aatgttgggt ggttccacga attccaaatc cggcttcaag   1140

tcactgagag ggtggtgacg atgagcaaag ctgtgatctg atctgctggc gcatgtcttc   1200

tacagcggct gcgactaacc ggcattttcg cctacagctc gggtccataa acagcgaagc   1260

agatagaaat gtgtacaact ttccagccga tggaactgta catcatcgtt catgttggat   1320

taacacttgt tgtaatgtat tattggtttt accatgcgga tctcttatca tatgagagga   1380

tgtgaatgaa aactgttctc ccgtcctccc ccctaaattc agaaaagttc agacagaagg   1440

actccaataa aaatagctag aatcgaatgc ttttgaacca aaaaaaaaaa aaaaaaa      1497
```

-continued

<210> SEQ ID NO 28
<211> LENGTH: 316
<212> TYPE: PRT
<213> ORGANISM: Oryza sativa

<400> SEQUENCE: 28

```
Met Asp Pro Val Leu Leu Asp Asp Ile Ile Arg Arg Leu Ile Glu Val
  1               5                  10                  15

Lys Asn Leu Lys Pro Gly Lys Asn Ala Gln Leu Ser Glu Ser Glu Ile
             20                  25                  30

Lys Gln Leu Cys Ala Thr Ser Lys Glu Ile Phe Leu Asn Gln Pro Asn
         35                  40                  45

Leu Leu Glu Leu Glu Ala Pro Ile Lys Ile Cys Gly Asp Val His Gly
     50                  55                  60

Gln Tyr Ser Asp Leu Leu Arg Leu Phe Asp Tyr Gly Gly Tyr Pro Pro
 65                  70                  75                  80

Gln Ser Asn Tyr Leu Phe Leu Gly Asp Tyr Val Asp Arg Gly Lys Gln
                 85                  90                  95

Ser Leu Glu Thr Ile Cys Leu Leu Leu Ala Tyr Lys Ile Lys Tyr Pro
            100                 105                 110

Glu Asn Phe Phe Leu Leu Arg Gly Asn His Glu Cys Ala Ser Val Asn
        115                 120                 125

Arg Ile Tyr Gly Phe Tyr Asp Glu Cys Lys Arg Arg Phe Ser Val Lys
    130                 135                 140

Leu Trp Lys Thr Phe Thr Asp Cys Phe Asn Cys Leu Pro Val Ala Ala
145                 150                 155                 160

Leu Ile Asp Glu Lys Ile Leu Cys Met His Gly Gly Leu Ser Pro Glu
                165                 170                 175

Leu Asn Lys Leu Asp Gln Ile Leu Asn Leu Asn Arg Pro Thr Asp Val
            180                 185                 190

Pro Asp Thr Gly Leu Leu Cys Asp Leu Leu Trp Ser Asp Pro Ser Asn
        195                 200                 205

Asp Ala Gln Gly Trp Ala Met Asn Asp Arg Gly Val Ser Tyr Thr Phe
    210                 215                 220

Gly Pro Asp Lys Val Ser Glu Phe Leu Glu Lys His Asp Leu Asp Leu
225                 230                 235                 240

Ile Cys Arg Ala His Gln Val Val Glu Asp Gly Tyr Glu Phe Phe Ala
                245                 250                 255

Asn Arg Gln Leu Val Thr Ile Phe Ser Ala Pro Asn Tyr Cys Gly Glu
            260                 265                 270

Phe Asp Asn Ala Gly Ala Met Met Ser Val Asp Asp Thr Leu Met Cys
        275                 280                 285

Ser Phe Gln Ile Leu Lys Pro Ala Arg Lys Met Leu Gly Gly Ser Thr
    290                 295                 300

Asn Ser Lys Ser Gly Phe Lys Ser Leu Arg Gly Trp
305                 310                 315
```

<210> SEQ ID NO 29
<211> LENGTH: 1354
<212> TYPE: DNA
<213> ORGANISM: Oryza sativa

<400> SEQUENCE: 29

```
gccgcgccga gatctagggt tgggcgcgcg cgacgccccc cccccgcggc gaggaggatg      60

agcagccccc atggcggcct cgacgaccag atcgagcgcc tcatgcagtg caagcccctc     120
```

-continued

```
cccgagcccg aggtcagagc actttgcgag aaggcaaaag agatattgat ggaggagagc    180

aacgttcaac ctgtaaagag tcctgttaca atatgtggtg atattcatgg gcagtttcat    240

gaccttgcag aactgttccg aatcggtgga aagtgcccag atacaaacta cttgtttatg    300

ggagattacg tggatcgtgg ttattattct gttgaaactg tcacgctttt ggtggcttta    360

aaggttcgtt atcctcagcg aattactatt ctcagaggaa accacgaaag tcgacagatc    420

actcaagttt atggattcta tgacgagtgc ttaaggaagt acgggaatgc aaatgtgtgg    480

aaaactttta cagatctctt cgattacttc cccttgacag cattggttga gtcagaaata    540

ttttgcctgc atggtggatt atcgccatcc attgagacac ttgataacat acgtaacttc    600

gatcgtgtcc aagaagttcc ccatgaaggg cccatgtgtg atcttctgtg gtctgatcca    660

gacgatcgat gtggttgggg tatttctcct cgaggtgctg gatacacctt cgggcaggat    720

atatcagagc agttcaacca taccaataat ttaagactta ttgctagagc tcaccagttg    780

gtcatggagg gattcaattg ggctcatgag caaaaagttg ttaccatatt tagtgcacct    840

aattattgct atcgctgtgg gaacatggca tcaatcttgg aagttgatga ttgcagggag    900

catacattca tccagtttga gccagcccca agaaggggag agccagatgt aactcgtaga    960

acacctgact atttcctgtg atgtaaaagt ggtggactgt ctctgcagca aatgtttgat   1020

agctagctgg gaggattcat cgtgttctca cttatctcta attggctgat gcttggcttg   1080

ggggctgcag tggtgactcg aagcatcaag tagcaaattt gtattatgaa aggaaaacta   1140

ttctctttgt attcattttg ttcgcctttc ttccccacaa atttcaccta attttctttt   1200

ttctttttc atgatccttg tagagatgaa caatgtagtt gtatggctcc ctgttgagcc   1260

ggtaggtctt tctgagtaca tcttgatttg ccgtacataa ttgcttgaaa aacaagtatt   1320

agaattcttt gtgaccaaaa aaaaaaaaaa aaaa                               1354
```

<210> SEQ ID NO 30
<211> LENGTH: 307
<212> TYPE: PRT
<213> ORGANISM: Oryza sativa

<400> SEQUENCE: 30

```
Met Ser Ser Pro His Gly Gly Leu Asp Asp Gln Ile Glu Arg Leu Met
  1               5                  10                  15

Gln Cys Lys Pro Leu Pro Glu Pro Glu Val Arg Ala Leu Cys Glu Lys
             20                  25                  30

Ala Lys Glu Ile Leu Met Glu Glu Ser Asn Val Gln Pro Val Lys Ser
         35                  40                  45

Pro Val Thr Ile Cys Gly Asp Ile His Gly Gln Phe His Asp Leu Ala
     50                  55                  60

Glu Leu Phe Arg Ile Gly Gly Lys Cys Pro Asp Thr Asn Tyr Leu Phe
 65                  70                  75                  80

Met Gly Asp Tyr Val Asp Arg Gly Tyr Tyr Ser Val Glu Thr Val Thr
                 85                  90                  95

Leu Leu Val Ala Leu Lys Val Arg Tyr Pro Gln Arg Ile Thr Ile Leu
            100                 105                 110

Arg Gly Asn His Glu Ser Arg Gln Ile Thr Gln Val Tyr Gly Phe Tyr
        115                 120                 125

Asp Glu Cys Leu Arg Lys Tyr Gly Asn Ala Asn Val Trp Lys Thr Phe
    130                 135                 140

Thr Asp Leu Phe Asp Tyr Phe Pro Leu Thr Ala Leu Val Glu Ser Glu
145                 150                 155                 160
```

-continued

```
Ile Phe Cys Leu His Gly Gly Leu Ser Pro Ser Ile Glu Thr Leu Asp
                165                 170                 175

Asn Ile Arg Asn Phe Asp Arg Val Gln Glu Val Pro His Glu Gly Pro
            180                 185                 190

Met Cys Asp Leu Leu Trp Ser Asp Pro Asp Asp Arg Cys Gly Trp Gly
        195                 200                 205

Ile Ser Pro Arg Gly Ala Gly Tyr Thr Phe Gly Gln Asp Ile Ser Glu
    210                 215                 220

Gln Phe Asn His Thr Asn Asn Leu Arg Leu Ile Ala Arg Ala His Gln
225                 230                 235                 240

Leu Val Met Glu Gly Phe Asn Trp Ala His Glu Gln Lys Val Val Thr
                245                 250                 255

Ile Phe Ser Ala Pro Asn Tyr Cys Tyr Arg Cys Gly Asn Met Ala Ser
            260                 265                 270

Ile Leu Glu Val Asp Asp Cys Arg Glu His Thr Phe Ile Gln Phe Glu
        275                 280                 285

Pro Ala Pro Arg Arg Gly Glu Pro Asp Val Thr Arg Arg Thr Pro Asp
    290                 295                 300

Tyr Phe Leu
305
```

<210> SEQ ID NO 31
<211> LENGTH: 1330
<212> TYPE: DNA
<213> ORGANISM: Oryza sativa

<400> SEQUENCE: 31

```
gccgtcaccg tcgcgccaac tgccgcaaac cgaataaacc gaatcgatct gagagaagaa     60

gaagaagaag acgcgatctc ggaggtggga gcgaaacgaa acgatgccgt ctcacgcgga    120

tctggaacga cagatcgagc agctgatgga gtgcaagcct ctgtcggagt cggaggtgaa    180

ggcgctgtgt gatcaagcga gggcgattct cgtggaggaa tggaacgtgc aaccggtgaa    240

gtgccccgtc accgtctgcg gcgatattca cggccagttt tacgatctca tcgagctgtt    300

tcggattgga gggaacgcac ccgataccaa ttatctcttc atgggtgatt atgtagatcg    360

tggatactat tcagtggaga ctgttacact tttggtggct ttgaaagtcc gttacagaga    420

tagaatcaca attctcaggg gaaatcatga aagtcgtcaa attactcaag tgtatggctt    480

ctatgatgaa tgcttgagaa aatatggaaa tgccaatgtc tggaaatact ttacagactt    540

gtttgattat ttacctctga ctgccctcat tgagagtcag attttctgct tgcatggagg    600

tctctcacct tctttggata cactggataa catcagagca ttggatcgta tacaagaggt    660

tccacatgaa ggaccaatgt gtgatctctt gtggtctgac cctgatgatc gctgtggatg    720

ggaatatct ccacgtggtg caggatacac atttggacag gatatagctg ctcagtttaa    780

tcataccaat ggtctctccc tgatatcgag agctcatcag cttgttatgg aaggattcaa    840

ttggtgccag gacaaaaatg tggtgactgt atttagtgca ccaaattact gttaccgatg    900

tgggaatatg gctgctatac tagaaatagg agagaatatg gatcagaatt tccttcagtt    960

tgatccagcg cccaggcaaa ttgagcctga caccacacgc aagactccag attattttt    1020

ataatttcat ttatctgcct gtttgtagtt actgctctct gccattactg tagatgtgtc   1080

tttaaggaaa ggagttttgc tgtttaagtg gagggtggtc atcaacataa ttctttcttt   1140

tggagtttac ctcctgctgc tgccgctgcc gctgccttat ttgtacaaga aaccaataga   1200
```

-continued

```
actgacacaa gccaccaatt ggggttgtat atttttggga ggaagcggta ataacatggt   1260

atatcttgtt ctgtaatcct ttttctttaa attgaatctc aagttagaga gcaaaaaaaa   1320

aaaaaaaaaa                                                          1330


<210> SEQ ID NO 32
<211> LENGTH: 306
<212> TYPE: PRT
<213> ORGANISM: Oryza sativa

<400> SEQUENCE: 32

Met Pro Ser His Ala Asp Leu Glu Arg Gln Ile Glu Gln Leu Met Glu
  1               5                  10                  15

Cys Lys Pro Leu Ser Glu Ser Glu Val Lys Ala Leu Cys Asp Gln Ala
             20                  25                  30

Arg Ala Ile Leu Val Glu Glu Trp Asn Val Gln Pro Val Lys Cys Pro
         35                  40                  45

Val Thr Val Cys Gly Asp Ile His Gly Gln Phe Tyr Asp Leu Ile Glu
     50                  55                  60

Leu Phe Arg Ile Gly Gly Asn Ala Pro Asp Thr Asn Tyr Leu Phe Met
 65                  70                  75                  80

Gly Asp Tyr Val Asp Arg Gly Tyr Tyr Ser Val Glu Thr Val Thr Leu
                 85                  90                  95

Leu Val Ala Leu Lys Val Arg Tyr Arg Asp Arg Ile Thr Ile Leu Arg
            100                 105                 110

Gly Asn His Glu Ser Arg Gln Ile Thr Gln Val Tyr Gly Phe Tyr Asp
        115                 120                 125

Glu Cys Leu Arg Lys Tyr Gly Asn Ala Asn Val Trp Lys Tyr Phe Thr
    130                 135                 140

Asp Leu Phe Asp Tyr Leu Pro Leu Thr Ala Leu Ile Glu Ser Gln Ile
145                 150                 155                 160

Phe Cys Leu His Gly Gly Leu Ser Pro Ser Leu Asp Thr Leu Asp Asn
                165                 170                 175

Ile Arg Ala Leu Asp Arg Ile Gln Glu Val Pro His Glu Gly Pro Met
            180                 185                 190

Cys Asp Leu Leu Trp Ser Asp Pro Asp Asp Arg Cys Gly Trp Gly Ile
        195                 200                 205

Ser Pro Arg Gly Ala Gly Tyr Thr Phe Gly Gln Asp Ile Ala Ala Gln
    210                 215                 220

Phe Asn His Thr Asn Gly Leu Ser Leu Ile Ser Arg Ala His Gln Leu
225                 230                 235                 240

Val Met Glu Gly Phe Asn Trp Cys Gln Asp Lys Asn Val Val Thr Val
                245                 250                 255

Phe Ser Ala Pro Asn Tyr Cys Tyr Arg Cys Gly Asn Met Ala Ala Ile
            260                 265                 270

Leu Glu Ile Gly Glu Asn Met Asp Gln Asn Phe Leu Gln Phe Asp Pro
        275                 280                 285

Ala Pro Arg Gln Ile Glu Pro Asp Thr Thr Arg Lys Thr Pro Asp Tyr
    290                 295                 300

Phe Leu
305


<210> SEQ ID NO 33
<211> LENGTH: 18
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 33

caggaaacag ctatgacc                                                 18


<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

ctaaagggaa caaaagctg                                                19


<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

tgtaaaacga cggccagt                                                 18


<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

atcccgggac gacatgagtg tgcctccgat atc                                33


<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

ctgagctcaa gtcccactat aagaagtagt ct                                 32


<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

atcccgggag gaaggggact ggacacaacg tgatg                              35


<210> SEQ ID NO 39
<211> LENGTH: 34
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 39
gcgttaacgc accatatgat gctttccggt cgtc 34

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ccgttatccg aggtcgaggt cagag 25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ccaggtcccg aatgtggtcc aagga 25

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgccaagcgc gcaattaacc ctcact 26

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcgtaatacg actcactata gggcga 26

<210> SEQ ID NO 44
<211> LENGTH: 299
<212> TYPE: PRT
<213> ORGANISM: Artificial Sequence
<220> FEATURE:
<223> OTHER INFORMATION: Description of Artificial Sequence: Consensus
      protein sequence

<400> SEQUENCE: 44

Met Ser His Gly Leu Asp Gln Ile Glu Gln Leu Met Glu Cys Lys Pro
1 5 10 15

Leu Ser Glu Glu Val Lys Ala Leu Cys Glu Lys Ala Lys Glu Ile Leu
20 25 30

Met Glu Glu Asn Val Gln Pro Val Lys Cys Pro Val Thr Ile Cys Gly
35 40 45

-continued

```
Asp Ile His Gly Gln Phe His Asp Leu Ile Glu Leu Phe Arg Ile Gly
     50                  55                  60

Gly Cys Pro Asp Thr Asn Tyr Leu Phe Met Gly Asp Tyr Val Asp Arg
 65                  70                  75                  80

Gly Tyr Tyr Ser Val Glu Thr Val Thr Leu Leu Val Ala Leu Lys Val
                 85                  90                  95

Arg Tyr Pro Asp Arg Ile Thr Ile Leu Arg Gly Asn His Glu Ser Arg
            100                 105                 110

Gln Ile Thr Gln Val Tyr Gly Phe Tyr Asp Glu Cys Leu Arg Lys Tyr
        115                 120                 125

Gly Asn Ala Asn Val Trp Lys Phe Thr Asp Leu Phe Asp Tyr Leu Pro
    130                 135                 140

Leu Thr Ala Leu Ile Glu Ser Glu Ile Phe Cys Leu His Gly Gly Leu
145                 150                 155                 160

Ser Pro Ser Ile Asp Thr Leu Asp Asn Ile Arg Ala Leu Asp Arg Val
                165                 170                 175

Gln Glu Val Pro His Glu Gly Pro Met Cys Asp Leu Leu Trp Ser Asp
            180                 185                 190

Pro Asp Asp Arg Cys Gly Trp Gly Ile Ser Pro Arg Gly Ala Gly Tyr
        195                 200                 205

Thr Phe Gly Gln Asp Ile Ser Glu Gln Phe Asn His Thr Asn Asn Leu
    210                 215                 220

Lys Leu Ile Ala Arg Ala His Gln Leu Val Met Glu Gly Phe Asn Trp
225                 230                 235                 240

Ala His Glu Lys Lys Val Val Thr Ile Phe Ser Ala Pro Asn Tyr Cys
                245                 250                 255

Tyr Arg Cys Gly Asn Met Ala Ala Ile Leu Glu Val Asp Asp Asn Met
            260                 265                 270

Asp His Thr Phe Ile Gln Phe Glu Pro Ala Pro Arg Arg Gly Glu Pro
        275                 280                 285

Asp Val Thr Arg Lys Thr Pro Asp Tyr Phe Leu
    290                 295
```

<210> SEQ ID NO 45
<211> LENGTH: 255
<212> TYPE: PRT
<213> ORGANISM: Artificial Sequence
<220> FEATURE:
<223> OTHER INFORMATION: Description of Artificial Sequence: Consensus protein sequence

<400> SEQUENCE: 45

```
Met Asp Ile Asp Arg Ile Leu Lys Leu Ser Glu Ser Glu Ile Arg Leu
  1               5                  10                  15

Cys Glu Ala Arg Glu Ile Leu Leu Glu Asn Val Gln Pro Val Ala Pro
             20                  25                  30

Val Thr Ile Cys Gly Asp Ile His Gly Gln Phe His Asp Leu Leu Arg
         35                  40                  45

Leu Phe Gly Gly Pro Asp Thr Asn Tyr Leu Phe Met Gly Asp Tyr Val
     50                  55                  60

Asp Arg Gly Tyr Ser Leu Glu Thr Ile Thr Leu Leu Leu Ala Leu Lys
 65                  70                  75                  80

Val Arg Tyr Pro Asp Asn Ile Thr Leu Leu Arg Gly Asn His Glu Ser
                 85                  90                  95

Arg Gln Ile Thr Gln Val Tyr Gly Phe Tyr Asp Glu Cys Arg Lys Tyr
            100                 105                 110
```

-continued

```
Gly Asn Ala Asn Leu Trp Lys Phe Thr Asp Leu Phe Asp Tyr Leu Pro
        115                 120                 125

Leu Thr Ala Leu Ile Asp Ile Leu Cys Leu His Gly Gly Leu Ser Pro
    130                 135                 140

Asp Leu Thr Leu Asp Asn Ile Arg Leu Asp Arg Glu Val Pro His Glu
145                 150                 155                 160

Gly Pro Leu Cys Asp Leu Leu Trp Ser Asp Pro Asp Asp Val Gly Trp
                165                 170                 175

Gly Ile Ser Pro Arg Gly Ala Gly Tyr Thr Phe Gly Asp Ile Ala Gln
            180                 185                 190

Phe Asn His Asn Leu Asp Leu Ile Cys Arg Ala His Gln Leu Val Asp
        195                 200                 205

Gly Tyr Phe Asp Arg Gln Leu Val Thr Ile Phe Ser Ala Pro Asn Tyr
    210                 215                 220

Cys Tyr Arg Cys Gly Asn Met Ala Ala Ile Leu Ser Val Asp Glu Asn
225                 230                 235                 240

Met Ser Phe Phe Pro Ala Arg Lys Thr Arg Lys Thr Tyr Phe Leu
                245                 250                 255


<210> SEQ ID NO 46
<211> LENGTH: 283
<212> TYPE: PRT
<213> ORGANISM: Artificial Sequence
<220> FEATURE:
<223> OTHER INFORMATION: Description of Artificial Sequence: Consensus
      protein sequence

<400> SEQUENCE: 46

Gly Leu Asp Asp Gln Ile Gln Leu Met Glu Cys Lys Leu Ser Glu Ser
  1               5                  10                  15

Glu Val Arg Leu Cys Glu Ala Lys Glu Ile Leu Met Glu Glu Asn Val
             20                  25                  30

Gln Pro Val Lys Ala Pro Val Thr Ile Cys Gly Asp Ile His Gly Gln
         35                  40                  45

Phe His Asp Leu Leu Glu Leu Phe Arg Ile Gly Gly Pro Asp Thr Asn
     50                  55                  60

Tyr Leu Phe Met Gly Asp Tyr Val Asp Arg Gly Tyr Tyr Ser Val Glu
 65                  70                  75                  80

Thr Val Thr Leu Leu Val Ala Leu Lys Val Arg Tyr Pro Asp Arg Ile
                 85                  90                  95

Thr Ile Leu Arg Gly Asn His Glu Ser Arg Gln Ile Thr Gln Val Tyr
            100                 105                 110

Gly Phe Tyr Asp Glu Cys Leu Arg Lys Tyr Gly Asn Ala Asn Val Trp
        115                 120                 125

Lys Phe Thr Asp Leu Phe Asp Tyr Leu Pro Leu Thr Ala Leu Ile Glu
    130                 135                 140

Ser Ile Phe Cys Leu His Gly Gly Leu Ser Pro Ser Leu Asp Thr Leu
145                 150                 155                 160

Asp Asn Ile Arg Leu Asp Arg Ile Gln Glu Val Pro His Glu Gly Pro
                165                 170                 175

Met Cys Asp Leu Leu Trp Ser Asp Pro Asp Asp Arg Cys Gly Trp Gly
            180                 185                 190

Ile Ser Pro Arg Gly Ala Gly Tyr Thr Phe Gly Gln Asp Ile Ala Ala
        195                 200                 205

Gln Phe Asn His Thr Asn Leu Leu Ile Ala Arg Ala His Gln Leu Val
```

-continued

```
    210                 215                 220

Met Glu Gly Tyr Asn Trp Asp Arg Gln Val Val Thr Ile Phe Ser Ala
225                 230                 235                 240

Pro Asn Tyr Cys Tyr Arg Cys Gly Asn Met Ala Ala Ile Leu Glu Val
                245                 250                 255

Asp Glu Asn Met Ser Phe Ile Gln Phe Asp Pro Ala Pro Arg Arg Glu
            260                 265                 270

Pro Asp Thr Arg Lys Thr Pro Asp Tyr Phe Leu
        275                 280
```